United States Patent
Chiu et al.

(10) Patent No.: US 11,648,560 B2
(45) Date of Patent: May 16, 2023

(54) PARTICLE SEPARATION SYSTEMS AND METHODS

(71) Applicants: UNIVERSITY OF WASHINGTON, Seattle, WA (US); MICAREO INC., Taipei (TW)

(72) Inventors: Daniel T. Chiu, Seattle, WA (US); Mengxia Zhao, Seattle, WA (US); Eleanor S. Shah, Seattle, WA (US); Perry G. Schiro, Burlingame, CA (US); Hui Min Yu, New Taipei (TW); Wei-Feng Fang, Taoyuan (TW); Jui-Lin Chen, Taipei (TW)

(73) Assignees: University of Washington, Seattle, WA (US); Micareo Inc., Taipei (TW)

( * ) Notice: Subject to any disclaimer, the term of this patent is extended or adjusted under 35 U.S.C. 154(b) by 413 days.

(21) Appl. No.: 16/639,083

(22) PCT Filed: Aug. 15, 2018

(86) PCT No.: PCT/US2018/000225
§ 371 (c)(1),
(2) Date: Feb. 13, 2020

(87) PCT Pub. No.: WO2019/035952
PCT Pub. Date: Feb. 21, 2019

(65) Prior Publication Data
US 2020/0206740 A1   Jul. 2, 2020

Related U.S. Application Data

(60) Provisional application No. 62/545,925, filed on Aug. 15, 2017.

(51) Int. Cl.
*B01L 3/00*        (2006.01)
*G01N 15/14*       (2006.01)
(Continued)

(52) U.S. Cl.
CPC ... *B01L 3/502761* (2013.01); *B01L 3/502715* (2013.01); *B01L 3/502738* (2013.01);
(Continued)

(58) Field of Classification Search
CPC ......... B01L 2200/0663; B01L 2300/06; B01L 2300/0681; B01L 2300/0864;
(Continued)

(56) References Cited

U.S. PATENT DOCUMENTS

2008/0318324 A1   12/2008   Chiu et al.
2009/0325215 A1   12/2009   Okano et al.
(Continued)

FOREIGN PATENT DOCUMENTS

CN   101583722 A   11/2009
CN   102460154 A    5/2012
(Continued)

OTHER PUBLICATIONS

Extended European Search Report dated Apr. 22, 2021, for corresponding European Patent Application No. 18845709.7, 7 pages.
(Continued)

*Primary Examiner* — Dean Kwak
(74) *Attorney, Agent, or Firm* — Christensen O'Connor Johnson Kindness PLLC

(57) ABSTRACT

Provided herein, among other aspects, are methods and apparatuses for analyzing particles in a sample. In some aspects, the particles can be analytes, cells, nucleic acids, or proteins and can be contacted with a tag, partitioned into aliquots, detected by a ranking device, and isolated. The methods and apparatuses provided herein may include a microfluidic chip. In some aspects, the methods and apparatuses may be used to quantify rare particles in a sample, such as cancer cells and other rare cells for disease diagnosis, prognosis, or treatment.

17 Claims, 34 Drawing Sheets

(51) Int. Cl.
*G01N 33/49* (2006.01)
*G01N 15/10* (2006.01)

(52) U.S. Cl.
CPC ..... *G01N 15/1434* (2013.01); *G01N 15/1459* (2013.01); *G01N 33/4915* (2013.01); *B01L 2200/0663* (2013.01); *B01L 2300/06* (2013.01); *B01L 2300/0681* (2013.01); *B01L 2300/0864* (2013.01); *B01L 2400/06* (2013.01); *B01L 2400/084* (2013.01); *G01N 15/1484* (2013.01); *G01N 2015/1006* (2013.01); *G01N 2015/149* (2013.01); *G01N 2015/1486* (2013.01)

(58) Field of Classification Search
CPC ........ B01L 2300/0867; B01L 2400/06; B01L 2400/084; B01L 2400/086; B01L 3/502715; B01L 3/50273; B01L 3/502738; B01L 3/502761; G01N 15/1434; G01N 15/1459; G01N 15/1484; G01N 2015/1006; G01N 2015/1415; G01N 2015/1486; G01N 2015/149; G01N 33/4915

See application file for complete search history.

(56) References Cited

U.S. PATENT DOCUMENTS

| | | | |
|---|---|---|---|
| 2012/0129190 A1 | 5/2012 | Chiu et al. | |
| 2013/0217110 A1 | 8/2013 | Ootani et al. | |
| 2016/0091489 A1 | 3/2016 | Fan et al. | |
| 2016/0146823 A1* | 5/2016 | Chiu | G01N 15/1456 506/9 |

FOREIGN PATENT DOCUMENTS

| | | |
|---|---|---|
| CN | 103889556 A | 6/2014 |
| CN | 105008895 A | 10/2015 |
| CN | 105242004 A | 1/2016 |
| CN | 105518464 A | 4/2016 |
| JP | 01-182736 A | 7/1989 |
| JP | 2016-527494 A | 9/2016 |
| TW | 201516412 A | 5/2015 |
| WO | 2012/094325 A2 | 7/2012 |

OTHER PUBLICATIONS

Gossett, D.R. et al., "Hydrodynamic stretching of single cells for large population mechanical phenotyping," Proceedings of the National Academy of Sciences USA, 109(20):7630-7635, May 15, 2012.

Sajeesh, P. and Sen, A.K., "Particle separation and sorting in microfluidic devices: a review," Microfluid Nanofluid, 17:1-52, 2014.

Notice of Reasons for Refusals (JP) dated Jan. 31, 2022, issued in corresponding Japanese Application No. 2020-531424, filed Aug. 15, 2018, 4 pages.

International Search Report and Written Opinion dated Nov. 5, 2018, for International Patent Application No. PCT/US2018/000225. (8 pages).

Taiwan Office Action of the Intellectual Property Office dated Apr. 21, 2022, issued in corresponding Taiwanese Application No. 107128510, filed Aug. 15, 2018, 7 pages.

International Preliminary Report on Patentability, dated Feb. 18, 2020, for International Patent Application No. PCT/US2018/000225. (6 pages).

First Chinese Office Action dated Jun. 22, 2022, issued in corresponding Chinese Application No. 201880064073.3, filed on Aug. 15, 2018, and its English translation thereof, 36 pages.

* cited by examiner

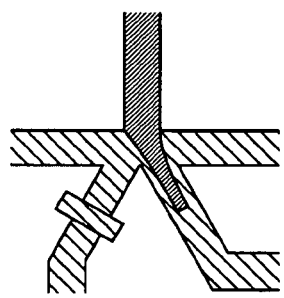
FIG. 3A
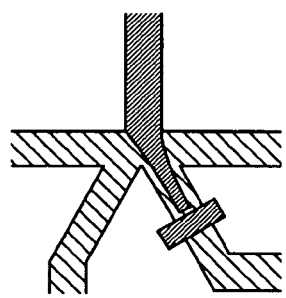
FIG. 3B
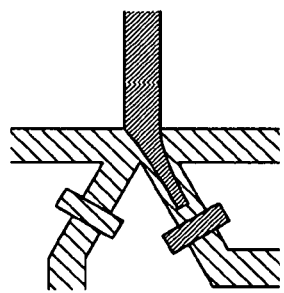
FIG. 3C
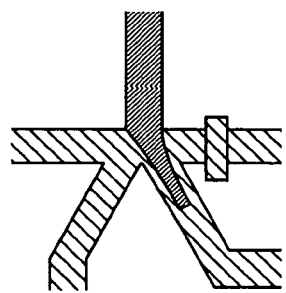
FIG. 3D
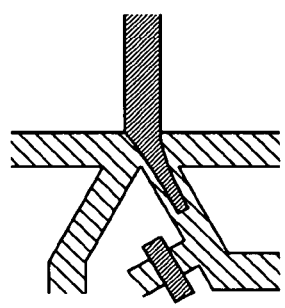
FIG. 3E
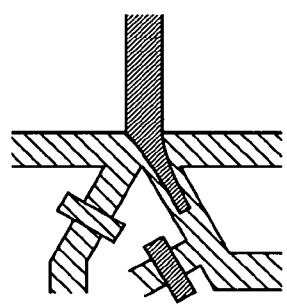
FIG. 3F
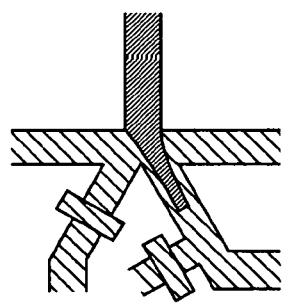
FIG. 3G
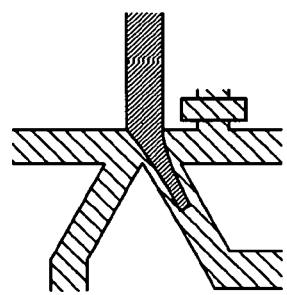
FIG. 3H
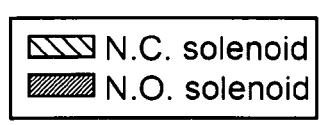

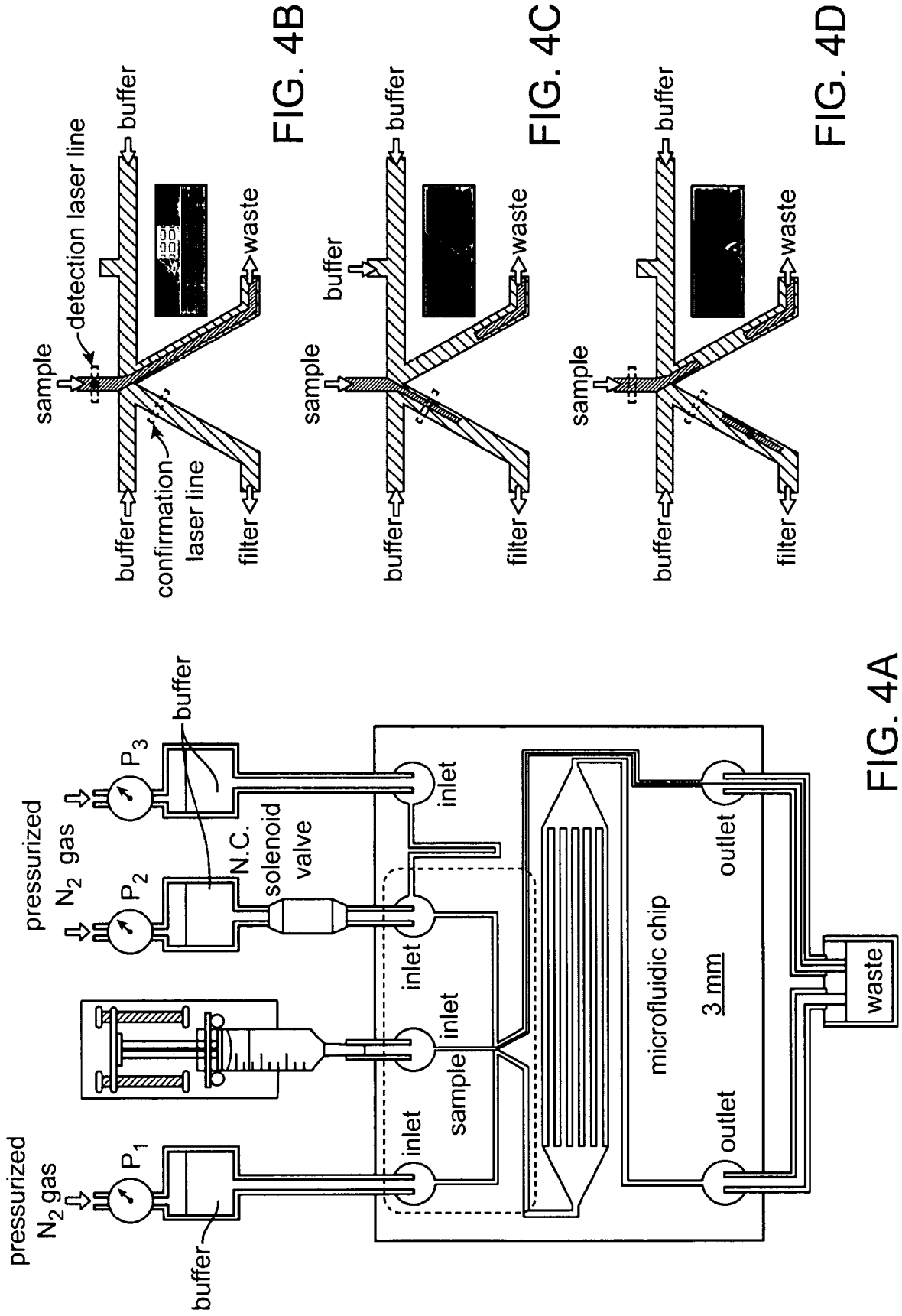

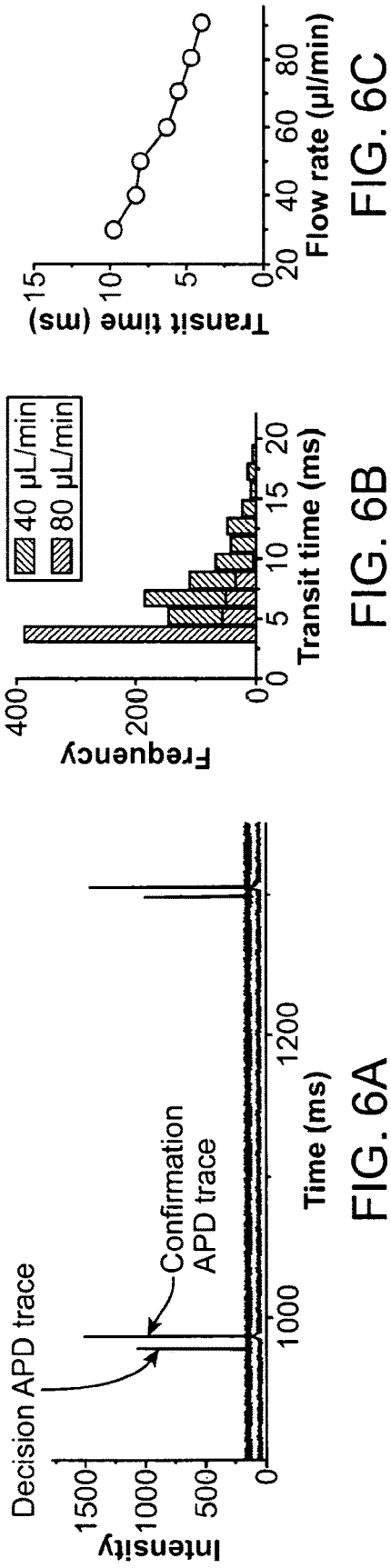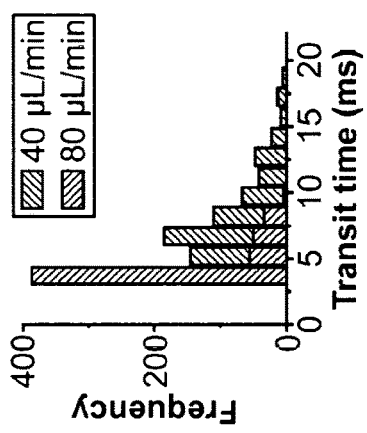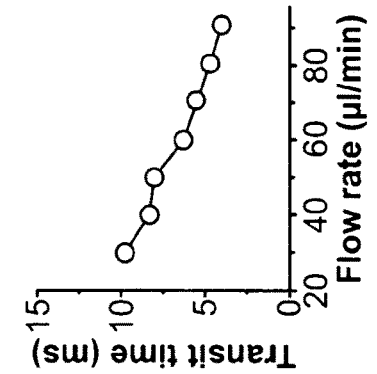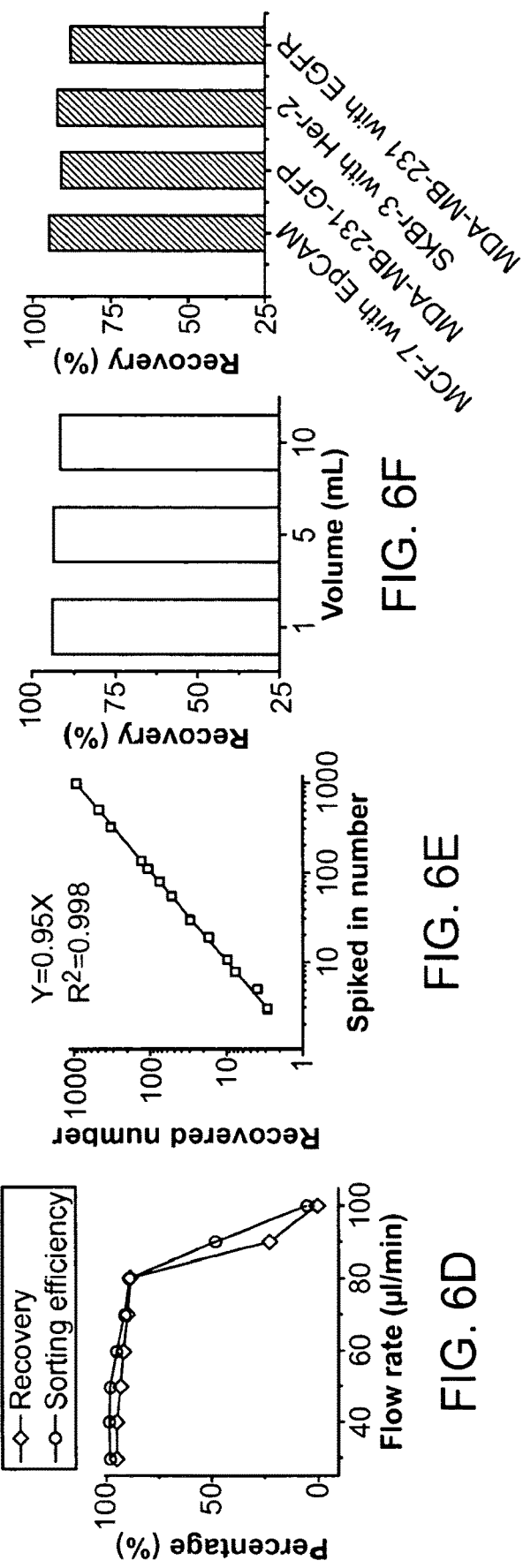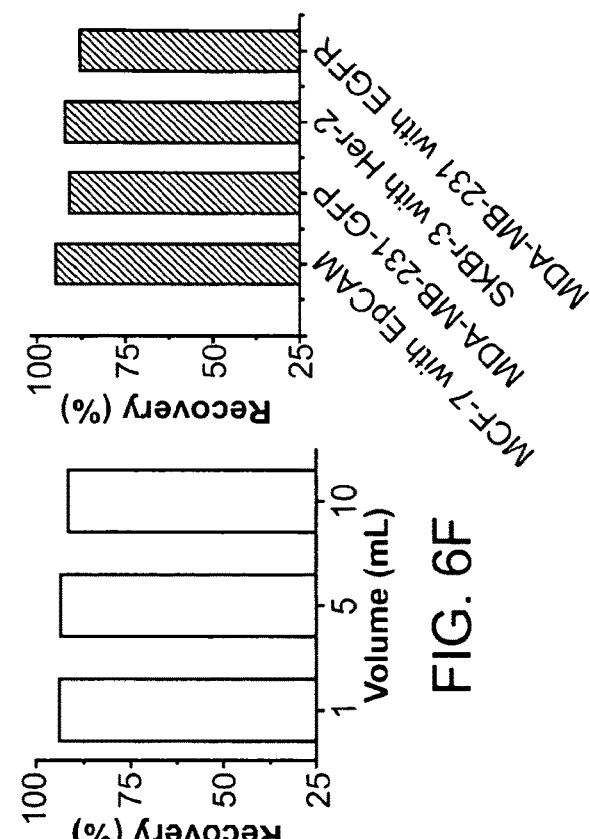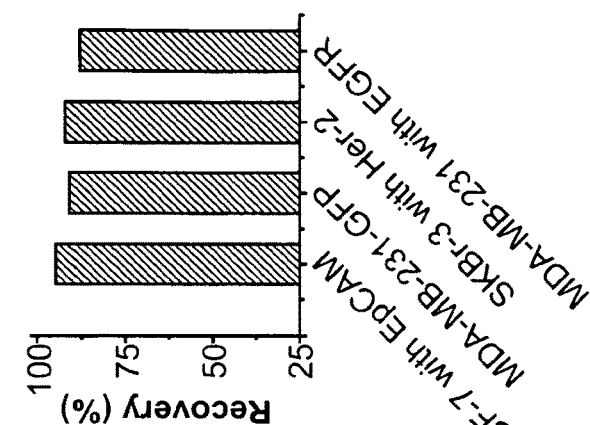

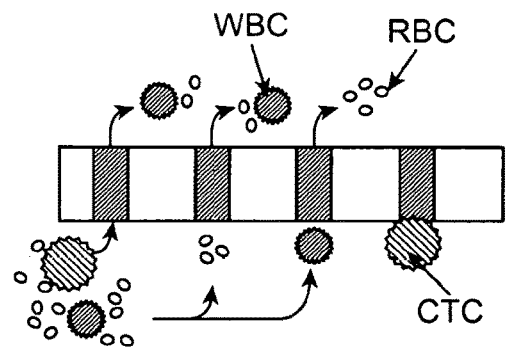
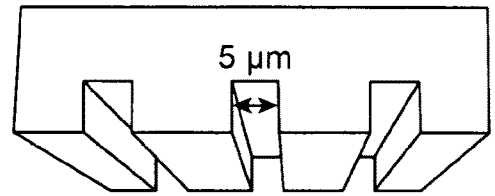
FIG. 7A  FIG. 7B
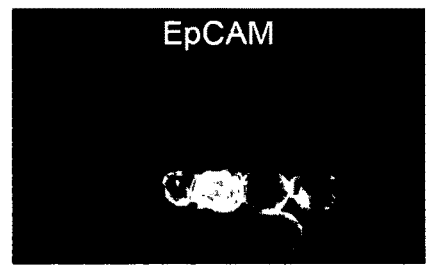
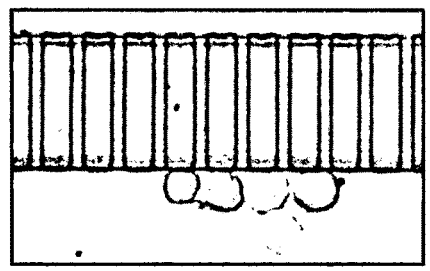
FIG. 7C
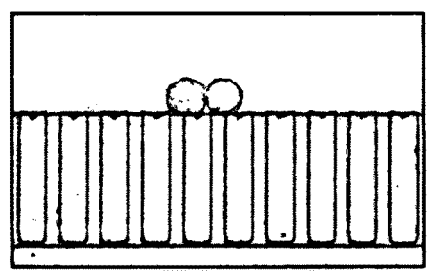
FIG. 7D
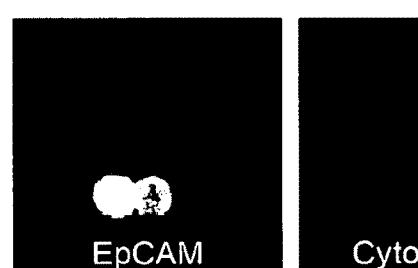
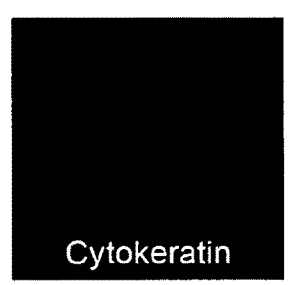
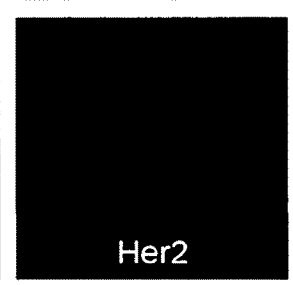
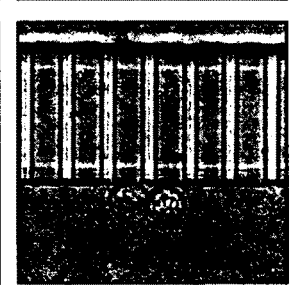
FIG. 7E

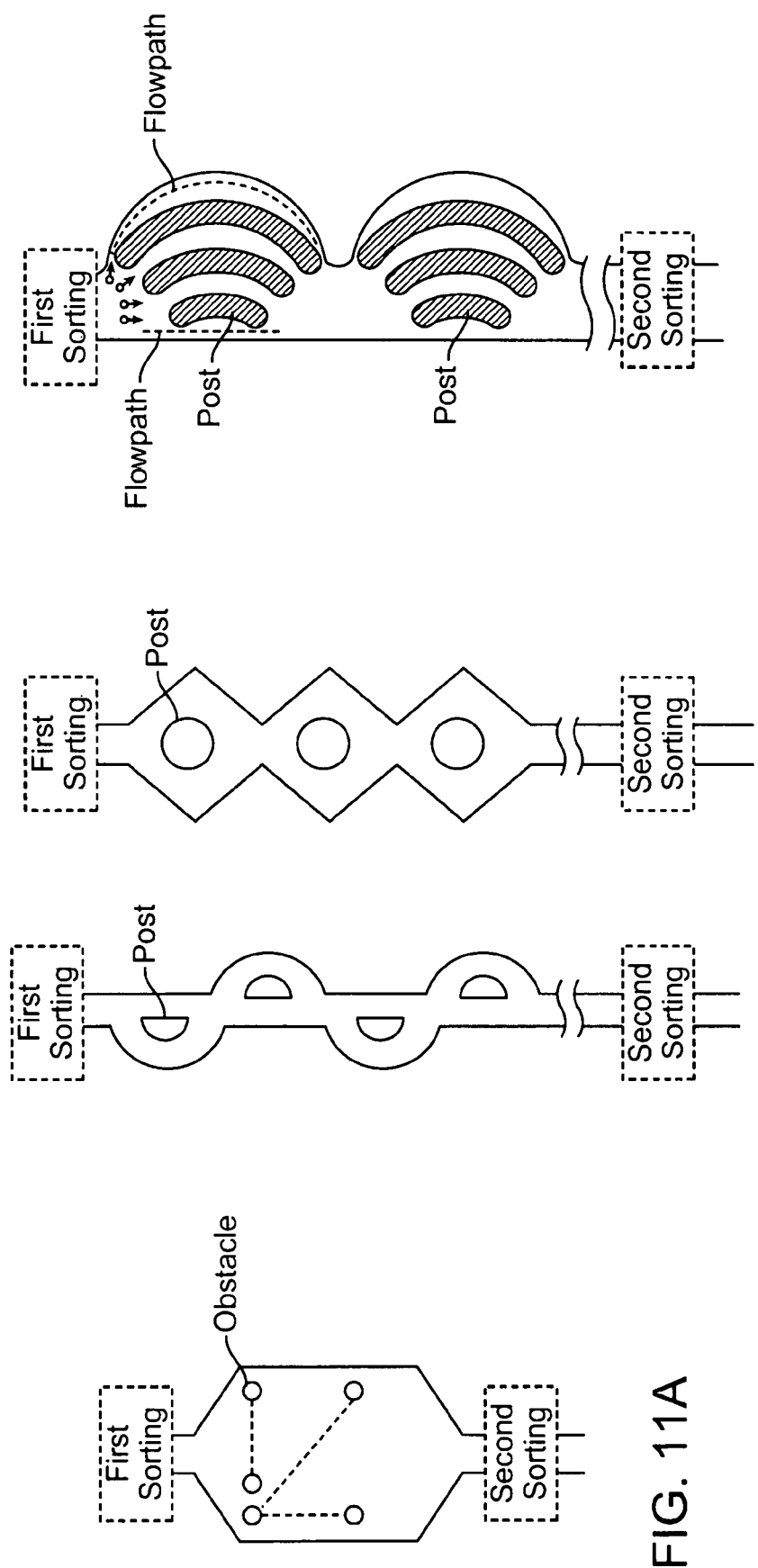

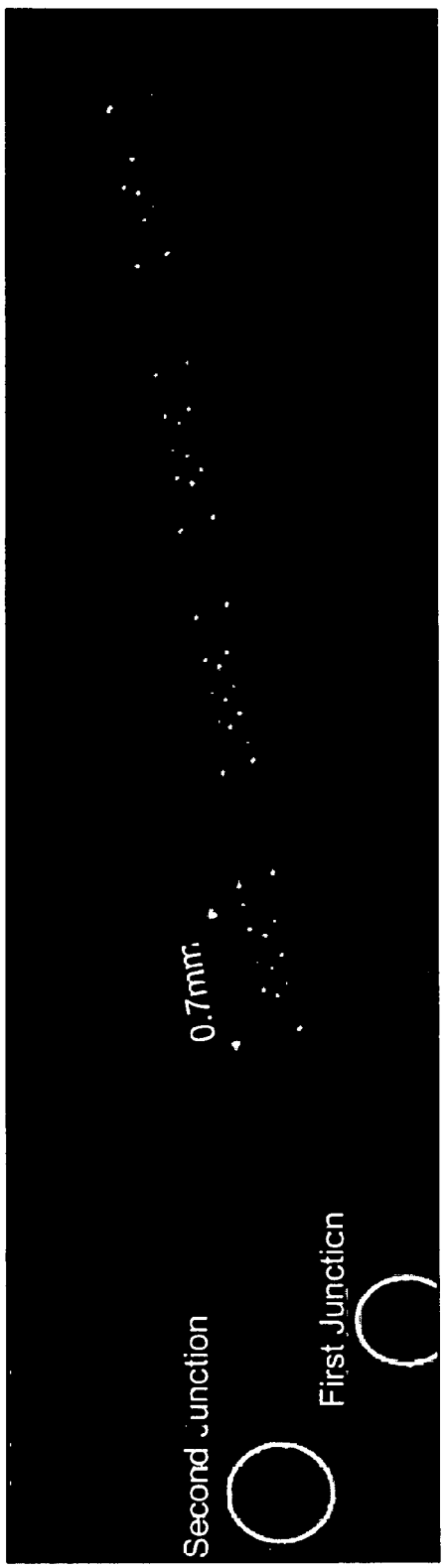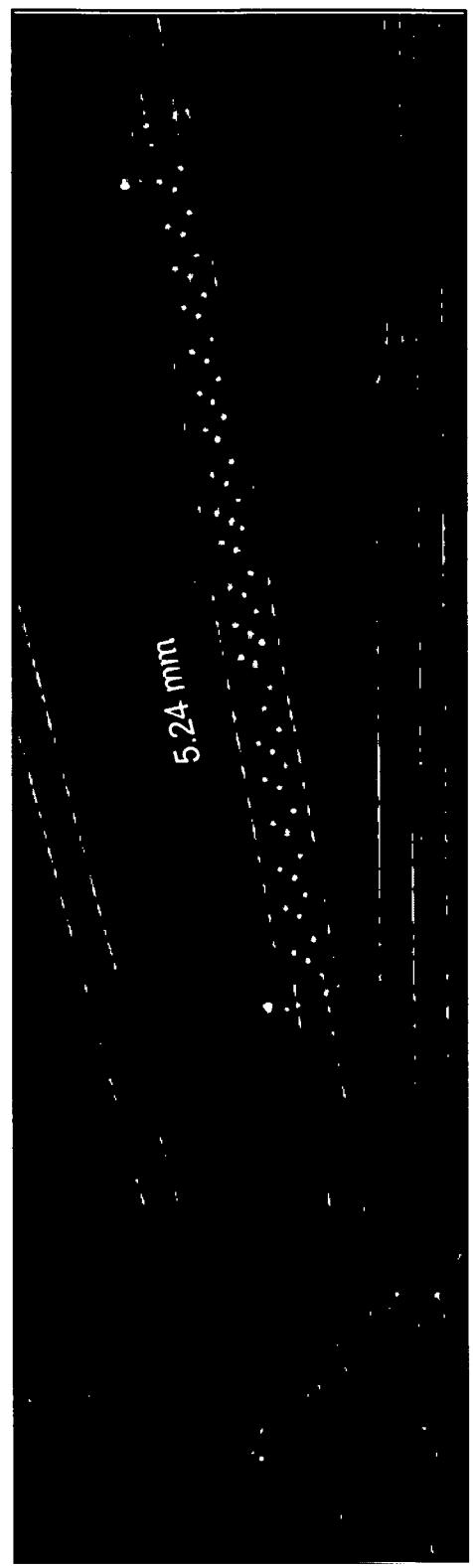
FIG. 21A
FIG. 21B

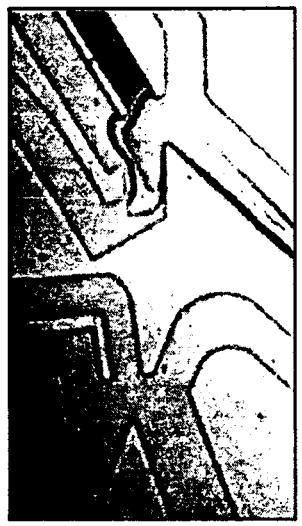
FIG. 27A
FIG. 27B

PARTICLE SEPARATION SYSTEMS AND METHODS

CROSS REFERENCE

This application is a national stage entry of International Patent Application No. PCT/US2018/000225, filed Aug. 15, 2018, which claims the benefit of U.S. Provisional Patent Application No. 62/545,925, filed Aug. 15, 2017, the entire contents of which are herein incorporated by reference.

BACKGROUND

Circulating tumor cells (CTCs) are shed into the bloodstream from the primary tumor and are an important aspect of cancer metastasis. CTCs have been detected in many different types of cancer, such as breast, lung, prostate and pancreatic cancers. The number of CTCs directly correlates with the clinical outcome in metastatic patients, providing valuable prognostic information that can be helpful to manage clinical care.

SUMMARY

Described herein are methods, apparatuses, systems and devices for isolating and analyzing particles (such as cells) from fluid samples (such as blood).

In various aspects, a method for collecting a particle in a fluid sample comprises the operations of: i) detecting a first presence of the particle in a first aliquot of the sample; ii) upon detecting the presence of the particle in the first aliquot, directing the flow of the first aliquot to a first volume to form a first isolated sample; iii) dispersing the first isolated sample to form a dispersed sample; and iv) subjecting the dispersed sample to a separation procedure.

In various aspects, the separation procedure is an active separation procedure. In some cases, the separation procedure is a passive separation procedure.

In some aspects, detecting the first presence of the particle comprises: i) interrogating the particle in the first aliquot with a source of first electromagnetic radiation; and ii) detecting a first interaction of the first electromagnetic radiation with the particle in the first aliquot. In some cases, the first electromagnetic radiation comprises light, and in some cases, the light has a wavelength in a range selected from the group consisting of: 100 nm to 400 nm, 400 nm to 700 nm, 700 nm to 1,000 nm, 1 m to 10 µm, 10 µm to 100 µm, and 100 m to 1,000 µm.

In some cases, the first interaction is selected from the group consisting of: optical reflection, optical transmission, elastic optical scattering, inelastic optical scattering, Rayleigh scattering, Raman scattering, surface-enhanced Raman scattering, Mie scattering, Brillouin scattering, fluorescence, autofluorescence, laser-induced fluorescence, luminescence, bioluminescence, and chemiluminescence.

In some cases, detecting the first presence of the particle in the first aliquot is performed during continuous flow of the fluid sample.

In various aspects, the particle is a rare particle. In some cases, the rare particle is a cell, and, in some cases, the cell is a rare cell. In some cases, the rare cell is a cancerous cell, and, in some cases, the cancerous cell is a circulating tumor cell. In some cases, the rare cell is an immune cell. In some cases, the rare cell is a white blood cell.

In some cases, dispersing the first isolated sample comprises flow stretching of the first isolated sample, and, in some cases, the flow stretching is imparted by parabolic flow of the first isolated sample through a flow path. In some cases, the flow stretching is imparted by herringbone mixing of the first isolated sample. In some cases, the flow stretching is imparted by flow of the first isolated sample through a plurality of flow paths.

In some aspects, dispersing the first isolated sample comprises cell stretching of the first isolated sample. In some cases, the cell stretching is imparted by a barrier, and, in some cases, the barrier alters the velocity of a cell based on a physical attribute of the cell. In some cases, the physical attribute of the cell is selected from the group consisting of: cell volume, cell shape, and cell deformability. In some case, the barrier comprises a filter structure, a constriction of the channel, or a weir structure.

In some aspects, dispersing the first isolated sample comprises flow stretching and flow sorting.

In some cases, the separation procedure comprises: i) interrogating the particle with a source of second electromagnetic radiation; and ii) detecting a second interaction of the second electromagnetic radiation. In some cases, the second electromagnetic radiation comprises light, and in some cases, the light has a wavelength in a range selected from the group consisting of: 100 nm to 400 nm, 400 nm to 700 nm, 700 nm to 1,000 nm, 1 µm to 10 µm, 10 µm to 100 µm, and 100 µm to 1,000 µm.

In various aspects, the second interaction is selected from the group consisting of: optical reflection, optical transmission, elastic optical scattering, inelastic optical scattering, Rayleigh scattering, Raman scattering, surface-enhanced Raman scattering, Mie scattering, Brillouin scattering, fluorescence, autofluorescence, laser-induced fluorescence, luminescence, bioluminescence, and chemiluminescence.

In some aspects, detecting the second presence of the particle is performed during continuous flow of the fluid sample.

In some cases, the method further comprises collecting the particle in a structure, and in various cases, the structure is selected from the group consisting of: a vial, a well plate, and a filtration volume.

In some aspects, the methods described herein further comprise capturing the particle with a filter element. In some cases, the methods further comprise releasing the particle from the filter element, and, in some cases, the releasing comprises releasing the particle to a volume selected from the group consisting of: a vial a well plate, and an additional filtration volume.

In some aspects, the methods comprise contacting the filter element with one or more beads, and in some aspects, the releasing comprises contacting the filter element with one or more beads.

In various aspects, the methods described herein comprise operating a valve to concentrate the collected particle or purifying the particle using a passive fluidic structure. In some cases, the methods comprise dispersing the particle using one or more barrier, one or more weir stretcher, one or more microslit, or one or more microfilter.

In various aspects, the apparatuses for collecting a particle in a fluid sample comprise an input channel, a detector configured to detect the particle in the input channel, a directional flow channel in fluid communication with the input channel; a valve configured to modulate fluid flow in the directional flow channel; an output channel in fluid communication with the input channel; a dispersion stage in fluid communication with the output channel; and a computer comprising a processor and a non-transitory memory with executable instructions stored thereon, which when executed by the processor cause the apparatus to: operate the detector to detect a first presence of the particle in a first aliquot of the sample; operate the valve to direct the flow of the first aliquot to a first volume to form a first isolated sample upon detecting the presence of the particle in the first aliquot; direct the first isolated sample to the dispersion stage to form a dispersed sample; and perform a separation procedure on the dispersed sample.

In some cases, the separation procedure performed by the apparatus is an active separation procedure or a passive separation procedure. In some cases, detecting the first presence of the particle comprises: interrogating the particle in the first aliquot with a source of first electromagnetic radiation; and detecting a first interaction of the first electromagnetic radiation with the particle in the first aliquot. In some cases, the first electromagnetic radiation comprise light having a wavelength in a range selected from the group consisting of 100 nm to 400 nm, 400 nm to 700 nm, 700 nm to 1,000 nm, 1 µm to 10 µm, 10 µm to 100 µm, and 100 µm to 1,000 µm. In some cases, the first interaction is selected from the group consisting of: optical reflection, optical transmission, elastic optical scattering, inelastic optical scattering, Rayleigh scattering, Raman scattering, surface-enhanced Raman scattering, Mie scattering, Brillouin scattering, fluorescence, autofluorescence, laser-induced fluorescence, bioluminescence, and chemiluminescence. In some cases, the processor causes the detecting of the first presence of the particle in the first aliquot at the same time the processor causes the continuous flow of the fluid sample in the system.

In various aspects, dispersing the first isolated sample using an apparatus described herein comprises flow stretching of the first collected sample. In some aspects, the flow stretching is imparted by parabolic flow of the first collected sample through a flow path; and in some cases, the apparatus is further configured impart a parabolic flow of the collected sample through a flow path. In some aspects, the flow stretching is imparted by flow of the first isolated sample through a plurality of flow paths. In some aspects, dispersing the first isolated sample comprises flow stretching and cell stretching.

In some cases, apparatuses described herein comprise a herringbone stretcher configured to impart flow stretching on the first collected sample. In some cases, an apparatus described herein comprises a barrier configured to impart cell stretching on the first isolated sample. In some cases, the barrier is configured to alter the velocity of a cell based on a physical attribute of the cell, and, in some aspects, the physical attribute of the cell is selected from the group consisting of: cell volume, cell shape, and cell deformability. In some cases, the barrier comprises a filter structure or a constriction of the channel.

In various aspects, apparatuses described herein are configured to perform a separation procedure comprising: interrogating the particle with a source of second electromagnetic radiation; and detecting a second interaction of the second electromagnetic radiation with the particle. In some cases, the second electromagnetic radiation comprises light having a wavelength in a range selected from the group consisting of: 100 nm to 400 nm, 400 nm to 700 nm, 700 nm to 1,000 nm, 1 µm to 10 µm, 10 µm to 100 µm, and 100 µm to 1,000 µm. In some aspects, the second interaction is selected from the group consisting of: optical reflection, optical transmission, elastic optical scattering, inelastic optical scattering, Rayleigh scattering, Raman scattering, surface-enhanced Raman scattering, Mie scattering, Brillouin scattering, fluorescence, autofluorescence, laser-induced fluorescence, luminescence, bioluminescence, and chemiluminescence. In some aspects, the separation procedure comprises fluorescence activated aliquot sorting, eDAR, flow cytometry, fluorescence activated cell sorting (FACS), magnetic particle separation, or magnetic-activated cell sorting (MACS).

In various aspects, a processor of an apparatus described herein is configured to cause the detecting the second presence of the particle to be performed during continuous flow of the fluid sample. In some aspects, the processor is further configured to cause the particle to be collected in a volume connected to the outlet channel, the volume selected from the group consisting of: a vial, a well plate, and a filtration volume. In some aspects, the processor is further configured to cause the particle to be captured with a filter element. In some cases, the processor is further configured to cause the particle to be released from the filter element. In some cases, the processor is further configured to cause the particle to be released from the filter element and collected in a volume selected from the group consisting of: a vial, a well plate, and an additional filtration volume.

In various aspects, the processor is configured to direct one or more beads into contact with the filter element. In some aspects, the processor is configured to release the particle from the filter element by causing the filter element to be contacted with one or more beads. In some cases, the processor is further configured to concentrate the collected particle by operating a second valve.

In various aspects, the apparatuses are configured to concentrate the particle, the structure being selected from the group consisting of one or more barrier, one or more filter element, one or more weir stretcher, one or more microslit, and one or more microfilter.

In some cases, the apparatuses described herein further comprise a passive fluidic structure configured to purify the particle.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIGS. 3A-3H illustrate exemplary hydrodynamic sorting schemes, in accordance with some embodiments of the present disclosure.

FIGS. 4A-4D show the microfluidic chip and hydrodynamic switching scheme of ensemble eDAR according to an aspect of the present disclosure.

FIGS. 6A-6G show the characterization and analytical performances of eDAR according to an aspect of the present disclosure.

FIGS. 7A-7E shows microslits and multicolor fluorescence imaging of captured CTCs according to an aspect of the present disclosure.

FIGS. 11A-11D show top views of an exemplary first sorting stage connected to a second sorting stage with a channel containing obstacles or multiple flow paths of varying designs, in accordance with some embodiments of the present disclosure.

FIG. 21A shows a top view of an exemplary weir stretcher.

FIG. 21B shows a top view of an exemplary long weir stretcher.

FIGS. 27A-27B shows image frames depicting sorting in a sequential sorting fluidics apparatus.

DETAILED DESCRIPTION OF THE DISCLOSURE

Figure 1B:
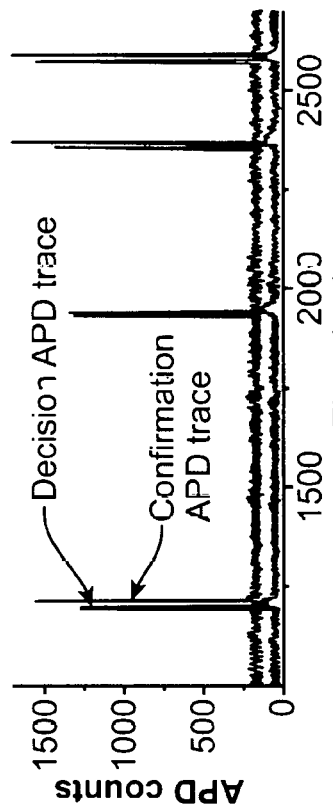
FIG. 1B shows a detection trace in accordance with some embodiments of the present disclosure.
Figure 1C:
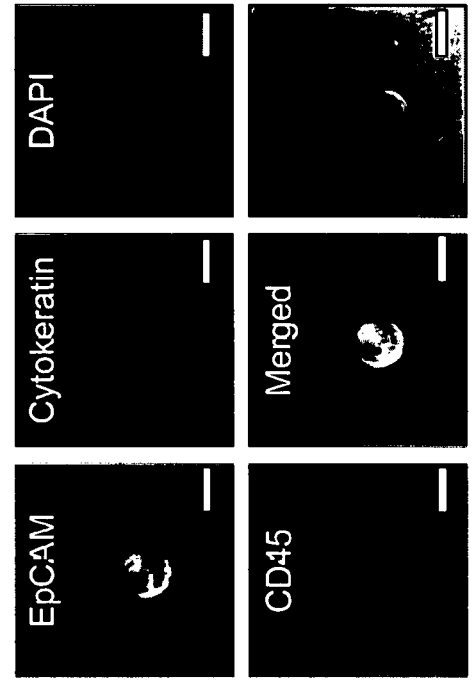
FIG. 1C shows fluorescence and bright-field imaging data in accordance with some embodiments of the present disclosure.

This disclosure provides methods, systems and devices for detecting, separating and analyzing particles (e.g., cells) in a fluid sample (e.g., blood), often with the use of a microfluidic apparatus. The particles can be rare particles (e.g., rare cells). Many of the microfluidic apparatuses and methods provided herein can be used to perform Ensemble Decision Aliquot Ranking (eDAR) on a fluid sample, which permits analysis of the fluid sample after the fluid sample is divided into aliquots. The microfluidic apparatuses and methods provided herein can be used to enhance the purity of particles in a fluid sample by employing eDAR followed by a dispersion operation and a separation operation.

The dispersion operation may be performed by a variety of microfluidic apparatuses and methods described herein. For instance, the dispersion operation may be performed using a flow stretching operation. The flow stretching may be imparted by parabolic flow of an aliquot or fluid volume containing a particle through a microfluidic channel following an initial eDAR operation, as described herein. The flow stretching may be imparted by flow of an aliquot or fluid volume containing a particle through a microfluidic channel comprising one or more herringbone structures following an initial eDAR operation, as described herein. The flow stretching may be imparted by flow of an aliquot or fluid volume containing a particle through multiple flow paths following an initial eDAR operation, as described herein. In some cases, the dispersion operation may be performed using a cell stretching operation. The cell stretching may be imparted by flow of an aliquot or fluid volume containing a particle through a barrier or a filter structure or weir structure or a channel with a constriction, which all serve to alter a velocity of the particle based on its volume, shape, or deformability. For example, a filter structure used to perform a cell stretching operation may comprise a plurality of apertures sized to preferentially affect the velocity of (e.g., to attenuate) one or more cell type. In some cases, one or more aperture of a filter structure used to perform a cell stretching operation can have a height, length, width or cross-section sized (e.g., relative to a dimension or property of a target cell, such as the target cell's diameter or deformability) to require cells of the one or more cell type to deform to pass through an aperture of the filter structure). In some instances, the dispersion operation may be performed using a combination of a flow stretching operation and a cell stretching operation.

Following the dispersion operation, a separation operation may be performed. The separation operation may be a passive separation operation or an active separation operation. The separation operation may be a second eDAR operation. The separation operation may be a flow cytometry (e.g. fluorescence activated cell sorting) operation. The separation operation may be a magnetic separation operation.

The microfluidic apparatuses and methods described herein may provide significantly enhanced separation of target particles from non-target particles in a fluid sample, as compared to isolation of the target particles using eDAR alone. In some cases, final collected particle purities may be enhanced by a factor of 5 times, 10 times, 20 times, 30 times, or more than 30 times compared to the purity attainable by eDAR alone.

The methods, systems, apparatuses and devices described in the present disclosure can be used in a wide variety of applications in biology and pathology for the separation, concentration, and/or isolation of analytes (e.g., rare cells). For example, some applications can include, but are not limited to, the capture of rare cells (e.g., cancer cells, cancer stem cells, malaria infected erythrocytes, stem cells, fetal cells, immune cells, infected cells) from fluids (e.g., body fluids) for diagnosis and prognosis of disease; isolation of single-celled parasites (e.g., *giardia, cryptosporidium*) for water quality monitoring; isolation of infected cells (e.g., lymphocytes, leukocytes) for monitoring disease progression (e.g., HIV, AIDS, cancer); fetal cells in maternal blood for screening (e.g., disease, genetic abnormalities); stem cells for use in therapeutic applications; prion-infected cells for prion-related (e.g., mad cow) disease screening; and others.

In a particular aspect, the rare particle is a rare cell. Rare cells can be nucleated or non-nucleated. Rare cells include, but are not limited to, cells expressing a malignant phenotype; fetal cells, such as fetal cells in maternal peripheral blood, tumor cells, such as tumor cells which have been shed from tumor into blood or other bodily fluids; cells infected with a virus, such as cells infected by HIV, cells transfected with a gene of interest; and aberrant subtypes of T-cells or B-cells present in the peripheral blood of subjects afflicted with autoreactive disorders.

As used herein, an "ensemble-decision" refers to a decision made based on the detection of the presence or absence of a characteristic in an ensemble, or a group, of particles. A group can comprise at least 3 particles, analytes and/or cells. In some aspects, an ensemble-decision will be made based on the presence or absence of a single distinct particle in an aliquot of a fluid sample containing a plurality of particles. Importantly, ensemble-decisions made based on the presence or absence of a single particle will be applied to the entire aliquot (i.e., to all of the particles present in the aliquot).

As used herein, an "aliquot" refers to a portion of the total volume of a fluid sample to be analyzed. An aliquot can contain at least one particle, analyte or cell. An aliquot can contain a group of particles, analytes or cells. An aliquot may occupy a three-dimensional space and the particles within may distribute randomly without organization. An aliquot may have a finite depth, and particles can distribute along the depth with no discernible layers. In the context of the present application, an aliquot is analyzed in its entirety without sub-division.

As used herein, the phrase "partitioning a fluid" refers to separating or otherwise redirecting a portion or aliquot of a fluid from the total volume of a fluid sample.

In certain aspects, an aliquot can comprise a fraction of a larger fluid sample, for example, about ½ of a fluid sample, or about ⅓, ¼, ⅕, ⅙, ⅐, ⅛, ⅑, ⅒, or less of a fluid sample. In certain aspects, an aliquot can comprise, for example, about 10% of a fluid sample, or about 9%, 8%, 7%, 6%, 5%, 4%, 3%, 2%, 1%, 0.5%, 0.1%, 0.05%, 0.01%, 0.001%, or less of a fluid sample. As such, a fluid that is to be examined or processed by an eDAR methodology provided herein can be divided, for example, into at least about 2 aliquots, or at least about 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 175, 200, 225, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, 5 million, 6 million, 7 million, 8 million, 9 million, 10 million, or more aliquots. One of skill in the art would understand that the number of aliquots into which a fluid sample would be partitioned into will depend upon the number of rare particles expected in the fluid and the total volume of the fluid sample.

In certain aspects, an aliquot can comprise a fraction of a larger fluid sample, for example, ½ of a fluid sample, or ⅓, ¼, ⅕, ⅙, ⅐, ⅛, ⅑, ⅒, or less of a fluid sample.

In certain aspects, an aliquot can comprise, for example, 10% of a fluid sample, or 9%, 8%, 7%, 6%, 5%, 4%, 3%, 2%, 1%, 0.5%, 0.1%, 0.05%, 0.01%, 0.001%, or less of a fluid sample. As such, a fluid that is to be examined or processed by an eDAR methodology provided herein can be divided, for example, into at least 2 aliquots, or at least 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 175, 200, 225, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, 3,000, 3,500, 4,000, 4,500, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1 million, 2 million, 3 million, 4 million, 5 million, 6 million, 7 million, 8 million, 9 million, 10 million, or more aliquots. One of skill in the art would understand that the number of aliquots into which a fluid sample would be partitioned into will depend upon the number of rare particles expected in the fluid and the total volume of the fluid sample.

In certain aspects, an aliquot can have a volume, for example, of between about 0.1 nL and about 10 mL, or between about 1 nL and about 1 mL, or between about 1 nL and about 100 µL, or between about 1 nL and about 10 µL, or between about 1 nL and about 1 µL, or between about 1 nL and about 100 nL, or between about 0.1 nL and about 10 nL.

In certain aspects, an aliquot can have a volume, for example, of between 0.1 nL and 10 mL, or between 1 nL and 1 mL, or between 1 nL and 100 μL, or between 1 nL and 10 μL, or between 1 nL and 1 μL, or between 1 nL and 100 nL, or between 0.1 nL and 10 nL.

As used herein, the term "ranking" refers to assessing a quantitative property, qualitative property, or importance of an aliquot by categorization. In one aspect, an aliquot can be ranked as either null (for example, when a rare particle is not detected in the aliquot) or nonzero (for example, when at least one rare particle is detected in an aliquot). In one aspect, the ranking can be binary. In other aspects, an aliquot can be ranked according to additional categories, for example, which correlate with the concentration of the rare particle in the aliquot, the identity of the rare particle in the aliquot, the identities of a plurality of different rare particles in the aliquot, and the like. In this fashion, any number of categories can be assigned based on ranges of concentration, for example, between about 1 and 10, between about 11 and 20, between about 1 and 50, between about 51 and 100, between about 1 and 100, between about 101 and 201, etc. In some aspects, the number of categories can be assigned based on ranges of concentration, for example, between 1 and 10, between 11 and 20, between 1 and 50, between 51 and 100, between 1 and 100, between 101 and 201, etc. These rankings can be assigned an arbitrary number corresponding to one of a number of predetermined quantitative or qualitative categories (e.g., 0, 1, 2, 3, 4, 5, etc.), or a number corresponding to an actual value for the number or approximate number or rare particles in the aliquot.

As used herein, the term "microfluidic chip" is used interchangeably with the terms chip, fluidic chip, microchip or fluidic microchip.

As used herein, a "computer" refers to at least a digital processor. The digital processor can be, but is not limited to, a field programmable gate array (FGPA), application specific integrated circuit (ASIC) or real-time (RT) processor.

The eDAR apparatus can be used for the identification and isolation of analytes (e.g., rare cells). eDAR can process a sample in aliquots and can collect rare cells in a channel or a chamber by an active sorting step controlled by a hydrodynamic switching scheme. An "all-in-one microfluidic chip," referred to herein as microfluidic chip, with channels and chambers can be used for sorting rare cells. The microfluidic chip can be composed, in part, of a functional area, a microfabricated filter. eDAR can be used to rapidly (e.g., less than or equal to 12.5 minutes per 1 mL) analyze a fluid containing a mixed population of analytes (e.g., whole blood at greater than or equal to one milliliter) with a high recovery ratio (e.g, greater than or equal to 90%) and a low false positive rate (e.g., close to zero).

Figure 5:
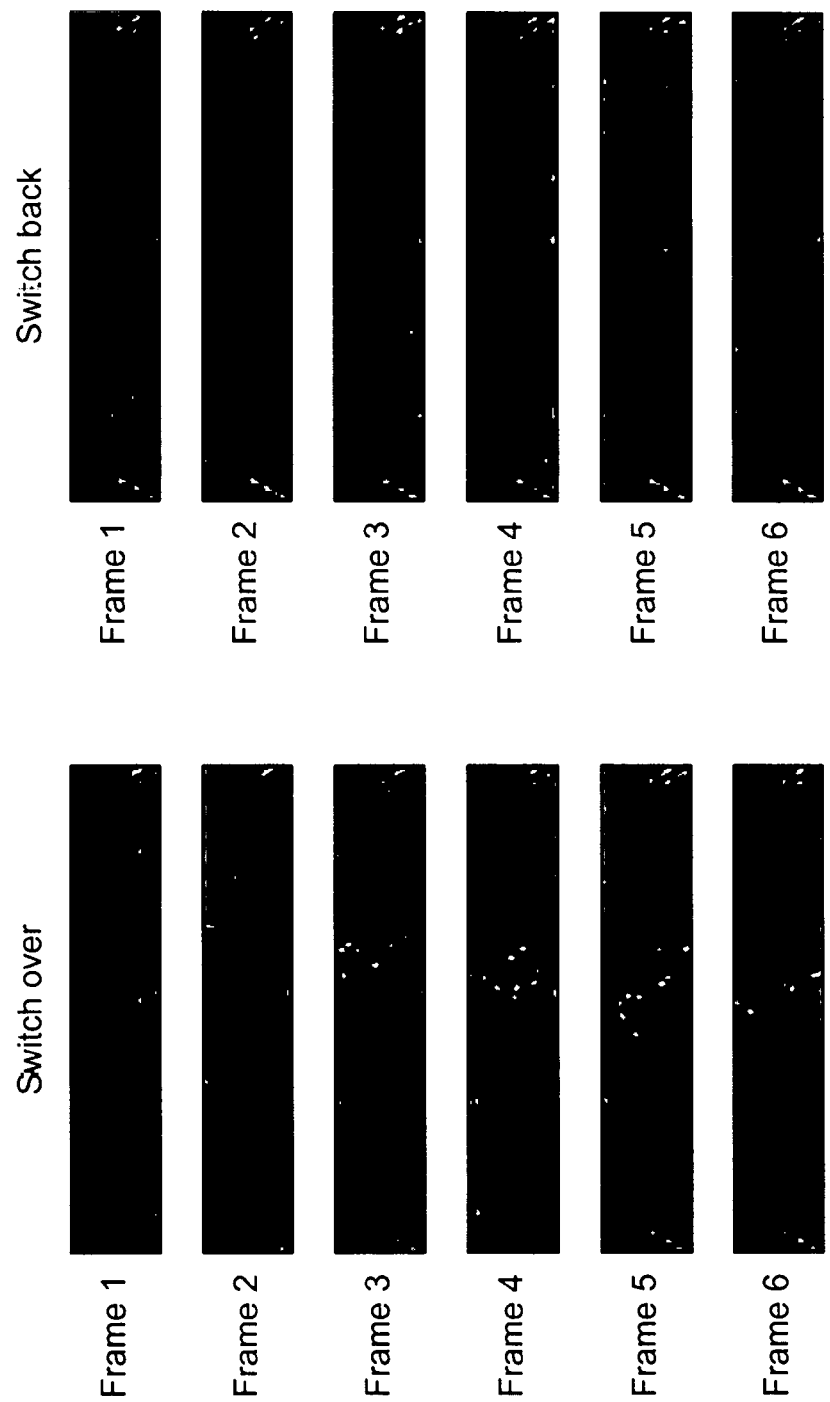
FIG. 5 depicts an example of the switching time for the current fluidic scheme recorded by high speed camera according to an aspect of the present disclosure.

The general structure of the microfluidic chip and an example configuration of eDAR are depicted in FIG. 5. The bottom left channel can be used to collect sorted aliquots and can be used to transfer them to the subsequent purification (e.g., purification chamber) area (e.g., 20,000 microslits). The area-marked with a dashed box is further depicted in FIG. 5B-D. An example flow condition when no positive aliquot was ranked is shown in FIG. 5B. The blood flow can be switched to the collection channel, and the sorted aliquot can be confirmed by the second window in FIG. 5C. FIG. 5D shows that the blood flow can be switched back after sorting the aliquot.

The apparatus can have several flow rates. The flow rates can refer to the rate in which a fluid flows through the eDAR apparatus and any components attached to the apparatus. In some aspects, exemplary flow rates can be less than about 5 μL/min, 10 μL/min, 20 μL/min, 25 μL/min, 30 μL/min, 35 μL/min, 40 μL/min, 41 μL/min, 42 μL/min, 43 μL/min, 44 μL/min, 45 μL/min, 46 μL/min, 47 μL/min, 48 μL/min, 49 μL/min, 50 μL/min, 51 μL/min, 52 μL/min, 53 μL/min, 54 μL/min, 55 μL/min, 56 μL/min, 57 μL/min, 58 μL/min, 59 μL/min, 60 μL/min, 61 μL/min, 62 μL/min, 63 μL/min, 64 μL/min, 65 μL/min, 66 μL/min, 67 μL/min, 68 μL/min, 69 μL/min, 70 μL/min, 71 μL/min, 72 μL/min, 73 μL/min, 74 μL/min, 75 μL/min, 76 μL/min, 77 μL/min, 78 μL/min, 79 μL/min, 80 μL/min, 81 μL/min, 82 μL/min, 83 μL/min, 84 μL/min, 85 μL/min, 86 μL/min, 87 μL/min, 87 μL/min, 88 μL/min, 89 μL/min, 90 μL/min, 91 μL/min, 92 μL/min, 93 μL/min, 94 μL/min, 95 μL/min, 96 μL/min, 97 μL/min, 98 μL/min, 99 μL/min, 100 μL/min, 105 μL/min, 110 μL/min, 115 μL/min, 120 μL/min, 125 μL/min, 130 μL/min, 140 μL/min, 150 μL/min, 160 μL/min, 170 μL/min, 180 μL/min, 190 μL/min, 200 μL/min, 225 μL/min, 250 μL/min, 275 μL/min, 300 μL/min, 350 μL/min, 400 μL/min, 450 μL/min, 500 μL/min, 600 μL/min, 700 μL/min, 800 μL/min, 900 μL/min or 1000 μL/min.

In some aspects, the flow rate can be within the range of about 51 μL/min-30 μL/min, 15 μL/min-50 μL/min, 25 μL/min-75 μL/min, 40 μL/min-80 μL/min, 50 μL/min-90 μL/min, 60 μL/min-100 μL/min, 800 μL/min-160 μL/min, 90 μL/min-180 μL/min, 100 μL/min-200 μL/min, 150 μL/min-300 μL/min, 200 μL/min-400 μL/min, 300 μL/min-500 μL/min, 400 μL/min-600 μL/min, 500 μL/min-700 μL/min, 600 μL/min-800 μL/min, 700 μL/min-900 μL/min or 800 μL/min-1000 μL/min.

In some aspects, exemplary flow rates can be less than 5 μL/min, 10 μL/min, 20 μL/min, 25 μL/min, 30 μL/min, 35 μL/min, 40 μL/min, 41 μL/min, 42 μL/min, 43 μL/min, 44 μL/min, 45 μL/min, 46 μL/min, 47 μL/min, 48 μL/min, 49 μL/min, 50 μL/min, 51 μL/min, 52 μL/min, 53 μL/min, 54 μL/min, 55 μL/min, 56 μL/min, 57 μL/min, 58 μL/min, 59 μL/min, 60 μL/min, 61 μL/min, 62 μL/min, 63 μL/min, 64 μL/min, 65 μL/min, 66 μL/min, 67 μL/min, 68 μL/min, 69 μL/min, 70 μL/min, 71 μL/min, 72 μL/min, 73 μL/min, 741 μL/min, 75 μL/min, 76 μL/min, 77 μL/min, 78 μL/min, 79 μL/min, 80 μL/min, 811 μL/min, 82 μL/min, 83 μL/min, 84 μL/min, 85 μL/min, 86 μL/min, 87 μL/min, 88 min, 89 μL/min, 90 μL/min, 91 μL/min, 92 μL/min, 93 μL/min, 94 μL/min, 95 μL/min, 96 μL/min, 97 μL/min, 98 μL/min, 99 μL/min, 100 μL/min, 105 μL/min, 1101 μL/min, 115 μL/min, 120 μL/min, 125 μL/min, 130 μL/min, 140 μL/min, 150 μL/min, 160 μL/min, 170 μL/min, 180 μL/min, 190 μL/min, 200 μL/min, 225 μL/min, 250 μL/min, 275 μL/min, 300 μL/min, 350 μL/min, 400 μL/min, 4501 μL/min, 500 μL/min, 600 μL/min, 700 μL/min, 800 μL/min, 900 μL/min or 1000 μL/min.

In some aspects, the flow rate can be within the range of 5 μL/min-30 μL/min, 15 μL/min-50 μL/min, 25 μL/min-75 μL/min, 40 μL/min-80 μL/min, 50 μL/min-90 μL/min, 60 μL/min-100 μL/min, 800 μL/min-160 μL/min, 90 μL/min-180 μL/min, 100 μL/min-200 μL/min, 150 μL/min-300 μL/min, 200 μL/min-400 μL/min, 300 μL/min-500 μL/min, 400 μL/min-600 μL/min, 500 μL/min-700 μL/min, 600 μL/min-800 μL/min, 700 μL/min-900 μL/min or 800 μL/min-1000 μL/min.

The apparatus can have several sorting efficiencies. The sorting efficiency can refer to the recovery of analytes of interest. In some aspects, an exemplary sorting efficiency can be greater than about 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In some aspects, the sorting efficiency can be within the range of about 5%-30%, 15%-50%, 25%-75%, 40%-80%, 50%-90% or 60%-100%.

In some aspects, an exemplary sorting efficiency can be greater than 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In some aspects, the sorting efficiency can be within the range of 5%-30%, 15%-50%, 25%-75%, 40%-80%, 50%-90% or 60%-100%.

The eDAR apparatus can have several recovery ratios. The recovery ratio can refer to the recovery of analytes of interest. In some aspects, the recovery ratio can be greater than about 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. In some aspects, the recovery ratio can be within the range of about 5%-30%, 15%-50%, 25%-75%, 40%-80%, 50%-90% or 60%-100%.

In some aspects, the recovery ratio can be greater than 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In some aspects, the recovery ratio can be within the range of 5%-30%, 15%-50%, 25%-75%, 40%-80%, 50%-90% or 60%-100%.

In some aspects an eDAR apparatus or method is used to separate a first cell type from a second cell type. In some aspects, an isolated sample comprises greater than 5%, 10%, 20%, 25%, 30%, 35%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of a total number of the first cell type. In some aspects, an isolated sample comprises less than than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45, 50%, 60%, 70%, 80%, or 90% of a total number of the second cell type.

The eDAR apparatus can include a microscope equipped with sources of radiation (e.g., lasers) for excitation and a mode of detection, sources of light, a timer, tubing, a waste-collection device, a camera for imaging tagged analytes (e.g., cells), pumps to control the flow of fluid in and out of the microfluidic chip, a digital processor to control the active sorting step and a digital processor (e.g., computer system) for processing images. The digital processor can be a computer.

In some aspects, the eDAR platform can include an apparatus for the capture of more than one analyte (e.g., rare cell). The "dual-capture" eDAR can separate multiple rare cells from a mixed sample. The mixed sample (e.g., fluid sample) can be labeled with a detection reagent and entered into the top of the "dual-capture" apparatus at a main channel. Two side channels can be used to control the hydrodynamic switching of the flow of the mixed sample. In some aspects, the flow can be controlled using two solenoids. Two subpopulations of rare cells can be separated and trapped on two different filtration areas on the same microfluidic chip.

In various aspects, apparatuses are provided for partitioning cells expressing a specific biomarker profile from a sample derived from a fluid, wherein: the apparatuses comprise a set of tubing connected to a microfluidic chip that has at least one channel and a chamber; and the apparatuses are capable of isolating the cells in the chamber, wherein, after isolation, the chamber comprises greater than 80% of the total population of cells in the sample expressing the specific biomarker profile and wherein, after isolation, the chamber comprises less than 5% of the total population of cells in the sample expressing a different biomarker profile.

In some aspects, the isolation of the cells expressing a specific biomarker profile occurs in less than 20 minutes. In some aspects, the specific biomarker profile is present on less than 5% of the cells in the sample of fluid. In certain aspects, the fluid is blood. In further aspects, the fluid is fractionated whole blood. In still further aspects, the fluid is the nucleated cell fraction of whole blood.

In various aspects, systems are provided for detecting a particle in a fluid sample, the systems comprising: a microfluidic chip comprising an input channel, a first output channel, a second output channel, and a directional flow channel; a valve, wherein the valve is separable from the microfluidic chip, and wherein: the valve regulates the flow of a first fluid in the directional flow channel; and the flow of the first fluid in the directional flow channel directs the flow of a second fluid from the input channel to the first output channel, the second output channel, or a combination thereof; a detector configured to detect a signal emitted from a portion of the second fluid in the input channel; and a processor configured to: assign a value to the portion based on the signal; and operate the valve. In some aspects, the valve is an electro-actuated valve.

In various aspects, systems are provided for detecting a particle in a fluid sample, the system comprising: (a) a microfluidic chip comprising at least one sample input channel, at least one directional flow channel, and at least two output channels, wherein the at least one directional flow channel intersects the sample input channel; (b) an electro-actuated valve that is located on a device that is not part of the microfluidic chip, wherein the electro-actuated valve controls the flow of a fluid by controlling an input channel that intersects at least one directional flow channel or at least one of the at least two output channels; (c) at least one detector capable of detecting one or more analytes in an aliquot of the fluid sample; and (d) a processor capable of assigning a value to the aliquot based on the presence, absence, identity, composition, or quantity of analytes in the aliquot, wherein the processor is in communication with the detector and the electro-actuated valve.

In some aspects, the electro-actuated valve is a solenoid valve. In certain aspects, the electro-actuated valve controls the flow of the fluid in at least one directional flow channel. In further aspects, the electro-actuated valve is normally closed and wherein the electro-actuated valve opens after receiving a signal from the processor. In still further aspects, the electro-actuated valve is normally open and wherein the electro-actuated valve closes after receiving a signal from the processor.

In some aspects, at least one directional flow channel comprises at least two ports and wherein the electro-actuated valve controls the flow of fluid through one of the ports. In certain aspects, the electro-actuated valve directly controls the flow of a fluid in at least one directional flow channel. In some aspects, the electro-actuated valve directly controls the flow of a fluid in a channel that feeds into at least one directional flow channel. In certain aspects, the electro-actuated valve directly controls the flow of a fluid in only one directional flow channel. In further aspects, the electro-actuated valve directly controls the flow of a fluid in an output channel. In still further aspects, the electro-actuated valve directly controls the flow of a fluid in a channel that feeds into an output channel. In some aspects, the electro-actuated valve is a piezo-electric valve.

In some aspects, a directional flow channel intersects an output channel at a junction. In certain aspects, the detector is located on at least one channel that is not an output channel. In some aspects, the device comprises a confirmatory laser. In certain aspects, the confirmatory laser is located on at least one channel that is not an input channel. In further aspects, the system comprises a second detector. In still further aspects, at least one channel is in fluidic communication with a filter.

In various aspects, devices are provided for detecting a rare particle in a fluid sample, the devices comprising: an input channel; a first output channel; a second output channel; a detector configured to detect the presence or absence of a particle in a portion of the fluid sample; a mechanism for directing the flow of the portion from the input channel to the first output channel, the second output channel, or a combination thereof based on the presence or absence of the particle; and a filter in fluidic communication with the first output channel. In some aspects, the filter comprises an array of apertures. In certain aspects, a smallest dimension of each aperture in the array is smaller than a smallest dimension of the particle.

In various aspects, devices are provided for detecting a rare particle in a fluid sample, the devices comprising: (a) at least one sample input channel; (b) at least two output channels, wherein at least one of the two output channels is in fluidic communication with an array of apertures; (c) at least one detector capable of detecting one or more rare particles in an aliquot of the fluid sample; and (d) a mechanism for sorting the one or more rare particles by directing the flow of aliquots containing the one or more rare particles through a first output channel.

In some aspects, the device comprises a first output channel and a second output channel. In certain aspects, the mechanism directs the flow of the aliquots into the second output channel if the aliquot does not contain a rare particle. In certain aspects, the mechanism for sorting comprises an electrode, a magnetic element, an acoustic element, or an electro-actuated element.

In some aspects, the array of apertures is disposed between an input channel and an output channel. In certain aspects, the array of apertures is in the same plane as an input channel and an output channels. In further aspects, the array of apertures is disposed within the first output channel. In still further aspects, the array of apertures is disposed in a chamber in fluidic communication with the first output channel. In some aspects, the array of apertures is configured so that the rare particles cannot pass through the apertures but at least one other particle is capable of passing through the apertures. In certain aspects, the array of apertures is configured so that the rare particles are capable of passing through the apertures but at least one other particle cannot pass through the apertures. In further aspects, the array of apertures comprises greater than 1000 apertures.

In certain aspects, the detector is selected from the group consisting of a camera, an electron multiplier, a charge-coupled device (CCD) image sensor, a photomultiplier tube (PMT), an avalanche photodiode (APD), a single-photon avalanche diode (SPAD), a silicon photomultiplier (SiPM), and a complementary metal oxide semiconductor (CMOS) image sensor.

In various aspects, integrated systems are provided for performing an assay, the systems comprising: a fluid sample comprising a particle, wherein the particle comprises a marker; an input channel; a first output channel; a second output channel; a first detector configured to detect the presence or absence of the particle in a portion of the fluid sample, the portion disposed within the input channel; a mechanism for directing the flow of the portion from the input channel to the first output channel based on the presence or absence of the particle; a micro-cavity in fluidic communication with the first output channel and configured to trap the particle.

Microfluidic Chip Design and Fabrication

The microfluidic chip can be fabricated to provide for an efficient active sorting scheme and subsequent purification (e.g., purification chamber) scheme. The microfluidic chip can be composed of two layers on a silicon master and can be fabricated with one-step replica molding into polydimethylsiloxane (PDMS). The microfluidic chip can be finished with bonding to a glass substrate.

Figure 2:
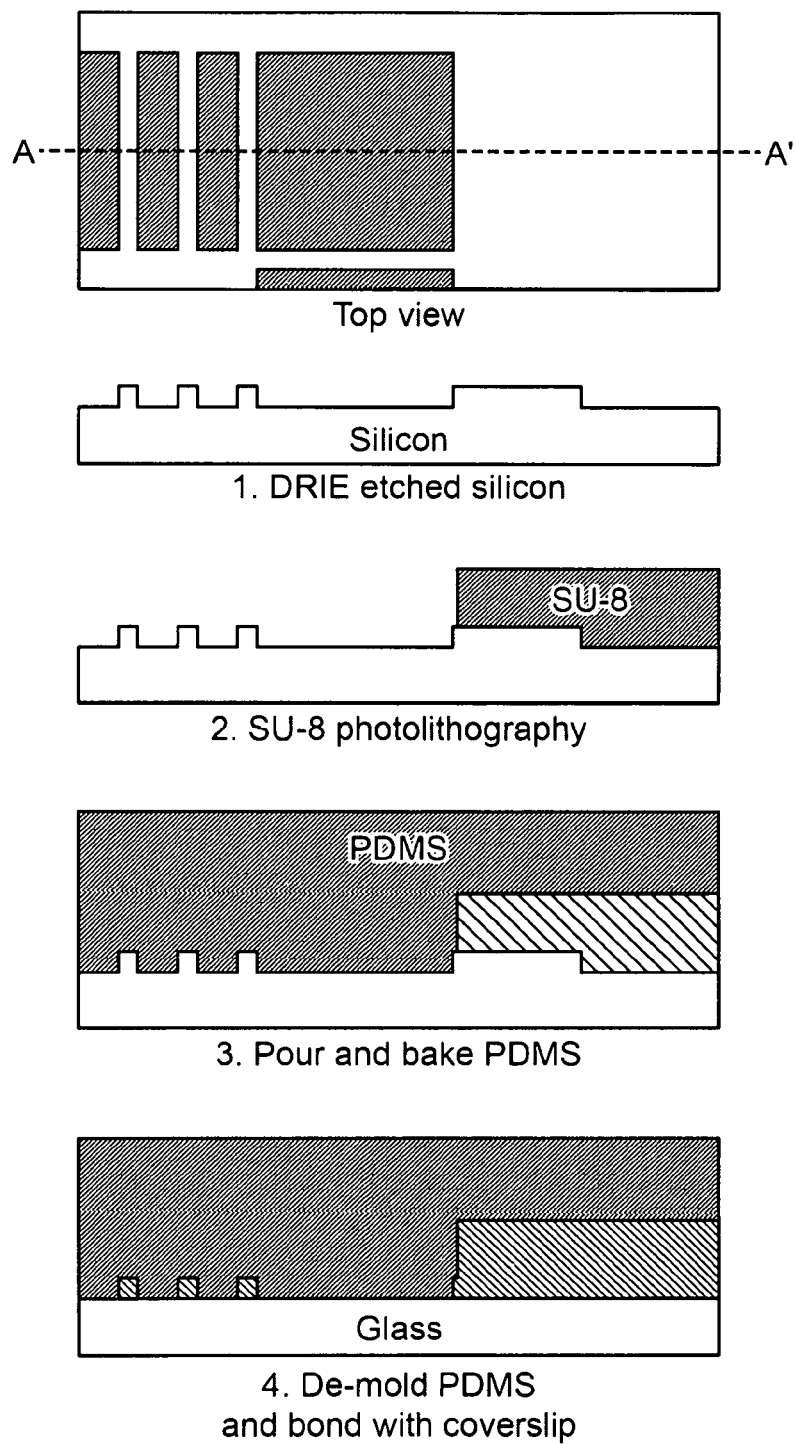
FIG. 2 illustrates an example of the process flow for microfabrication of the eDAR microfluidic chip according to an aspect of the present disclosure.

In some aspects, the silicon master can be fabricated using two photolithography processes (FIG. 2). The features can be designed using standard software (e.g., AutoCAD, Autodesk, San Rafael, Calif.), and can be written on a chrome mask. In these cases, positive resist lithography and deep reactive ion etching (DRIE) can be used to form the first layer (FIG. 2). The first layer can be the micro-filter feature. In some aspects, the positive photo resist (e.g., AZ 1512) is achieved by a process that can include a DRIE process. The DRIE process can achieve a depth (e.g., 4.5-5 µm) suitable for various features.

In some aspects, the second layer of the eDAR microfluidic chip features can be fabricated using a negative photoresist (e.g., SU-8-3050 from MicroChem, Newton, Mass.), and the height of the feature can be controlled (e.g., 50 µm). The master can be silanized using, for example, tridecafluoro-1,1,2,2-tetrahydrooctyl-1-trichlorosilane (Sigma-Aldrich, St. Louis, Mo.). The silanized master and silicon wafer can be coated with uncured PDMS and baked (e.g, for 2 hours at 70° C.). In some aspects, the piece of PDMS with the desired micro-features can be peeled off the silicon master, and then bonded with a piece of cover glass using the standard process of plasma oxidation to complete the fabrication of the eDAR microfluidic chip.

The microfluidic chip can contain specialized regions including, a staining region, an imaging region, and additional regions. In some aspects, the regions can be the same region used for at least one purpose. In other cases, the regions can be different regions use for one purpose. In other cases, the regions can be different regions use for at least one purpose. Each region can be used for more than one purpose. In some aspects, the eDAR microfluidic chip includes an integrated filtration area fabricated by standard lithography methods. In some aspects, the microfluidic chip can have two integrated functional areas, the eDAR sorting area and a slit-structure based filtration unit.

Channels in the Microfluidic Chip

The disclosure provided herein describes an apparatus for detecting an analyte (e.g., rare particle) in a fluid sample, the apparatus comprises: (a) at least a first input channel; (b) at least two outlet channels; (c) at least one detector capable of detecting one or more rare particles in an aliquot of the biological fluid; (d) a mechanism for directing the flow of the aliquot; and (e) a ranking device capable of assigning a value to the aliquot based on the presence, absence, identity, composition, or quantity of the rare particles in the aliquot, wherein the digital processor (e.g., computer) is in communication with the detector and the mechanism for directing the flow of the aliquot.

In some aspects, the apparatus provided herein can comprise a flow channel enclosed by walls and/or microfabricated on a substrate, with design features to minimize inadvertent damage to analytes (e.g., rare cells). Reducing inadvertent damage of rare cells can reduce the rate of false-negatives that cause erroneous patient diagnosis or prognosis. The flow channel can further comprise channels with hydrodynamically designed apertures to exclude biological cells with minimal stress or damage. The flow channel is as described in US Patent Publication Nos. 2007/0037172 and 2008/0248499. Such channels, referred to in the aforementioned patent applications as channels with one-dimensional ("1-D") apertures, reduce the hydrodynamic pressure experienced by the cells during the cell exclusion process and therefore reduce the likelihood of cell lysis. Channels with 1-D apertures can be strategically arranged in an array according to "effusive filtration" configuration as described in US Patent Publication No. 2008/0318324 to further re-direct, partition, dampen, or disperse the flow, consequently reducing the force of impact experienced by the cells at the moment of exclusion. The walls that enclose the flow channel can be fabricated using a UV-curing process in accordance with the procedures described in PCT/US2009/002426, from a biocompatible substrate material that is a medical-device grade polymer, so that the eDAR apparatus can be in compliance with regulations governing medical device manufacturing.

The main channel in the sorting area, which can be used to introduce fluid into the sorting junction, can have a particular height (e.g., 50 μm) and a particular width (e.g., 150 μm). In most cases, the other channels (e.g., four) can have a particular height (e.g., 50 μm) and a particular width (e.g., 200 μm). The slit-structure based filters in the filtration unit can have a particular height (e.g., 5 μm) and a particular width (e.g., 5 μm). The microfluidic chip can contain up to and can include 50,000 slits in the slit structure.

In some aspects, the eDAR apparatus can further comprise channels for channeling said aliquots based on said ranking. The channels can be treated with anticoagulant compounds, compounds that preferentially bind to the analytes (e.g., rare bioparticles), compounds that prevent agglomeration of rare bioparticles or their combinations.

In some aspects, the eDAR apparatus provided herein can comprise a plurality of flow channels, including one or more input flow channels (e.g., channels that bring an aliquot to a detection volume) and one or more output channels (e.g., channels that take an aliquot away from a detection volume). In some aspects, the eDAR apparatus as provided herein can comprise a combination of at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more input channels and at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more output channels. In some aspects, the eDAR apparatus as provided herein can comprise a combination of at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more input channels and at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, or more output channels. In some aspects, an apparatus can comprise multiple flow channels connecting to the main channel to inject additional fluid to alter the local velocity.

In some aspects, a fluid is delivered from a channel that is part of a microfluidic chip to a chamber that is in fluidic communication with the channel but is external to the microfluidic chip. In some aspects, the chamber is a vial. In other aspects, the chamber is a single well or a well in a well plate. In further aspects, the chamber is a microcentrifuge tube. In further aspects, the chamber is a microcentrifuge tube, wherein the microcentrifuge tube is an Eppendorf tube. Any suitable structure can be used for the vial and one of ordinary skill in the art could readily identify suitable chambers for use with the present disclosure.

In some aspects, a fluid is delivered from a channel to a chamber that is in fluidic communication with the channel via a tube or other suitable structure for transporting a fluid. The tube can comprise a material constructed from a biocompatible polymer. In other aspects, the chamber can be in fluidic communication with the channel via a capillary tube, such as a fused silica capillary tube, such as is used, e.g., for performing capillary electrophoresis. Other types of tubing suitable for bringing a channel into fluidic communication with a chamber will be readily apparent to one of ordinary skill in the art.

As used herein, the term "in fluidic communication with" (and variations thereof) refers to the existence of a fluid path between components. Being in fluidic communication neither implies nor excludes the existence of any intermediate structures or components. Two components can be in fluidic communication even if in some instances the path between them is blocked and/or fluid is not flowing between them. Thus, intermittent fluid flow is contemplated in certain aspects where there is fluidic communication.

In some aspects, an apparatus provided herein can comprise a flow channel or chamber enclosed by walls fabricated from materials including, but not limited to, polymeric materials (polydimethylsiloxane (PDMS), polyurethane-methacrylate (PUMA), polymethylmethacrylate (PMMA), polyethylene, polyester (PET), polytetrafluoroethylene (PTFE), polycarbonate, parylene, polyvinyl chloride, fluoroethylpropylene, lexan, polystyrene, cyclic olefin copolymers, cyclic olefin polymers, polyurethane, polyestercarbonate, polypropylene, polybutylene, polyacrylate, polycaprolactone, polyketone, polyphthalamide, cellulose acetate, polyacrylonitrile, polysulfone, epoxy polymers, thermoplastics, fluoropolymer, and polyvinylidene fluoride, polyamide, polyimide), inorganic materials (glass, quartz, silicon, GaAs, silicon nitride), fused silica, ceramic, glass (organic), metals and/or other materials and combinations thereof.

In some aspects, wall materials can be fabricated of porous membranes, woven or non-woven fibers (such as cloth or mesh) of wool, metal (e.g., stainless steel or Monel), glass, paper, or synthetic (e.g., nylon, polypropylene, polycarbonate, parylene, and various polyesters), sintered stainless steel and other metals, and porous inorganic materials such as alumina, silica or carbon.

In some aspects, the apparatus provided herein can comprise a flow channel or chamber that has been pre-treated with a chemical or biological molecule. For example, a channel or chamber can be treated with an anticoagulant compound to prevent or reduce the association of an analyte (e.g., rare particle or cell) in the fluid sample, a compound that preferentially binds to an analyte (e.g., rare particle or cell), or a compound that prevents or reduces the agglomeration or aggregation of a analyte (e.g., rare particle or cell) in the fluid sample.

In some aspects, the channel or chamber surfaces can be treated with anticoagulant compounds, compounds that preferentially bind to circulating tumor cells, or compounds that prevent the sticking of cells.

In some aspects, a channel or chamber surface can be modified chemically to enhance wetting or to assist in the adsorption of select cells, particles, or molecules. Surface-modification chemicals can include but not limited to silanes such as trimethylchlorosilane (TMCS), hexamethyldisilazane (HMDS), (Tridecafluoro-1,1,2,2-tetrahydrooctyl) trichlorosilane, chlorodimethyloctylsilane, Octadecyltrichlorosilane (OTS) or γ-methyacryloxypropyltrimethyoxy-silane; polymers such as acrylic acid, acrylamide, dimethylacrylamide (DMA), 2-hydroxyethyl acrylate, polyvinylalcohol (PVA), poly(vinylpyrrolidone (PVP), poly(ethylene imine) (PEI), Polyethylene glycol (PEG), epoxy poly(dimethylacrylamide (EPDMA), or PEG-monomethoxyl acrylate; surfactants such as Pluronic surfactants, Poly(ethylene glycol)-based (PEG) surfactants, sodium dodecylsulfate (SDS) dodecyltrimethylammonium chloride (DTAC), cetyltriethylammonium bromide (CTAB), or Polybrene (PB); cellulose derivatives such as hydroxypropylcellulose (HPC), or hydroxypropylmethylcellulose (HPMC); amines such as ethylamine, diethylamine, triethylamine, or triethanolamine, fluorine-containing compounds such as those containing polytetrafluoroethylene (PTFE) or Teflon.

Filtration

The eDAR apparatus provided herein can further comprise a filter element. In some aspects, the filter element can be in the form of micro-posts, micro-barriers, micro-impactors, micro-sieves, channels with apertures smaller than bioparticles, channels with apertures such that a bioparticle can be prevented from entering an aperture but fluid can be allowed to continue to flow around the bioparticle through the aperture ("1-D channels"), microbeads, porous membranes, protrusions from the walls, adhesive coating, woven or non-woven fibers (such as cloth or mesh) of wool, metal (e.g., stainless steel or Monel), glass, paper, or synthetic (e.g., nylon, polypropylene, polycarbonate, parylene, and polyester), sintered stainless steel or other metals, or porous inorganic materials such as alumina, silica. In some cases, a filter element can be formed using a 2-layer fabrication technique.

In some aspects, an array of apertures in the filter element is configured so that a particle of interest, such as a rare particle or cell, cannot pass through the apertures of the filter element, while at least one other particle is capable of passing through the apertures of the filter element. In other aspects, an array of apertures in the filter element is configured so that a particle of interest, such as a rare particle or cell, is capable of passing through the apertures of the filter element, while at least one other particle is incapable of passing through the apertures of the filter element.

In some aspects, the eDAR microfluidic chip can be fabricated with microslits (FIG. 7A). The microslits can be used to capture rare cells without retaining any additional non-specific particles (e.g., red blood cells, RBCs). The size of the microslits can vary. In some aspects, the height of the microslits can be less than or equal to about 0.1 µm, 0.5 µm, 1 µm, 5 µm, 10 µm, 15 µm, 20 µm, 25 µm, 30 µm, 35 µm, 40 µm, 50 µm, 75 µm or 100 µm tall. In some aspects, the height of the microslits can be in the range of about 0.1-5 µm, 1-10 µm, 5-15 µm, 10-30 µm, 15-40 µm, 20-50 µm, 30-75 µm and 50-100 µm tall. In some aspects, the width of the microslits can be less than or equal to about 0.1 µm, 0.5 µm, 1 µm, 5 µm, 10 µm, 15 µm, 20 µm, 25 µm, 30 µm, 35 µm, 40 µm, 50 µm, 75 µm or 100 µm tall. In some aspects, the width of the microslits can be in the range of about 0.1-5 µm, 1-10 µm, 5-15 µm, 10-30 µm, 15-40 µm, 20-50 µm, 30-75 µm and 50-100 µm tall. For example, the microslits can have a height of 5 µm and width of 5 µm (FIG. 7B).

In some aspects, the height of the microslits can be less than or equal to 0.1 µm, 0.5 µm, 1 µm, 5 µm, 10 µm, 15 µm, 20 µm, 25 µm, 30 µm, 35 µm, 40 µm, 50 µm, 75 µm or 100 µm tall. In some aspects, the height of the microslits can be in the range of 0.1-5 µm, 1-10 µm, 5-15 µm, 10-30 µm, 15-40 µm, 20-50 µm, 30-75 µm and 50-100 µm tall. In some aspects, the width of the microslits can be less than or equal to 0.1 µm, 0.5 µm, 1 µm, 5 µm, 10 µm, 15 µm, 20 µm, 25 µm, 30 µm, 35 µm, 40 µm, 50 µm, 75 µm or 100 µm tall. In some aspects, the width of the microslits can be in the range of 0.1-5 µm, 1-10 µm, 5-15 µm, 10-30 µm, 15-40 µm, 20-50 µm, 30-75 µm and 50-100 µm tall.

In some aspects, microfluidic chips can be prepared with 100, 200, 300, 400, 500, 600, 700, 800, 900, 1000, 5000, 20,000, 30,000, 40,000, or 50,000 apertures or microslits. In other aspects, microfluidic chips can be prepared with greater than 100, greater than 200, greater than 300, greater than 400, greater than 500, greater than 600, greater than 700, greater than 800, greater than 900, greater than 1000, greater than 5000, greater than 20,000, greater than 30,000, greater than 40,000, or greater than 50,000 apertures or microslits. In some aspects, pressures can be lower for microfluidic chips with more microslits. For example, the eDAR microfluidic chip with 20,000 slits required a pressure of less than 4 psi on the two side-buffer channels to balance the hydrodynamic switching process. In some aspects, the lower pressure across the microfilter can minimize the stress upon and deformation of the isolated rare cell.

Microslits can be used as a source of filtration. In some aspects, the microslits can be fabricated from any material that allows for sorting and does not cause aberrations during imaging (e.g., PDMS) and bonded with a piece of coverslip for use with imaging systems (FIGS. 7C and 7D). In some aspects, the microslits can be components of microfilters. For example, a microfilter can be a filter element having slits (e.g., microslits), pores (e.g., micropores), or apertures with at least one dimension (e.g., width, height, depth, or diameter) that is from 1 micrometer and 100 micrometers.

In some aspects, use of the microslits for filtration purposes can improve imaging accuracy and enumeration of trapped cells. In some aspects, the microslits can increase the speed and efficiency of a second round of labeling on trapped rare cells. For example, two cancer cells labeled with anti-EpCAM-PE can be trapped on the microslit (FIG. 7E). The cells can be fixed, permeabilized, and labeled with anti-Cytokeratin-Alexa488, anti-CD45-Alexa700, anti-Her2-Alexa647 and Hoechst.

Hydrodynamic Sorting

Two key factors that contribute to the features and performance of the eDAR platform are (1) an efficient and active sorting scheme and a (2) subsequent efficient purification (e.g., purification chamber) scheme. The analytical performance of the microfluidic chip and hydrodynamic switching mechanisms can be optimized for a particular recovery efficiency (e.g., 95%), a particular false positive rate (e.g., 0) and a particular throughput (e.g., 4.8 mL of whole blood per hour).

In some aspects, the mechanism for directing the flow directs the flow of an aliquot containing a rare particle into one of a plurality of outlet channels depending on the identity, composition, or quantity of the rare particle. The mechanism for directing the flow of the aliquot can either be into a first outlet channel, if the aliquot contains a rare particle, or a second outlet channel, if the aliquot does not contain a rare particle.

In some aspects, the mechanism for directing the flow of the aliquot can comprise an electrode, a magnetic element, an acoustic element, an electro-actuated element, an electric field, a piezo-electric valve, or a magnetic field. In other cases, the mechanism for directing the flow of the aliquot can comprise one or more electro-actuated valves or pistons, wherein the valves or pistons control the flow of a liquid in at least a first directional flow channel that intersects with the first input channel and the two outlet channels at a first junction.

In some aspects, the apparatus provided herein can comprise one or more electrodes for tracking and/or manipulating the trajectory or flow of a particle, aliquot, or fluid sample. In some aspects, the apparatus provided herein can comprise one or more electrodes for tracking and/or manipulating the trajectory or flow of an ensemble, or a group, of particles or aliquots. In this case, the electrode can enhance the separation of an aliquot based on phenomena such dielectrophoretic or electrowetting.

In other cases, the apparatuses provided herein can further comprise a magnetic element for the separation of a rare particle (e.g., cell) bound to or bound by a magnetic particle. In other cases, the apparatuses provided herein can further comprise a magnetic element for the separation of an ensemble or group of rare particles (e.g., cells) bound to or bound by at least one magnetic particle. In some aspects, the magnetic element can enhance the separation of an aliquot, particle, or cell based on the magnetic susceptibility of the cells or the micro-magnetic or nano-magnetic particles attached to a particle or cell. In some aspects, the magnetic element can enhance the separation of an ensemble or a group of particles, or cells based on the magnetic susceptibility of the cells or the micro-magnetic or nano-magnetic particles attached to at least one particle or cell.

The eDAR apparatus can have a second line-confocal detection window located on the collection side to monitor the efficiency of the hydrodynamic switching in real time. In some aspects, the eDAR apparatus can be paired with confocal imaging.

Figure 1A:
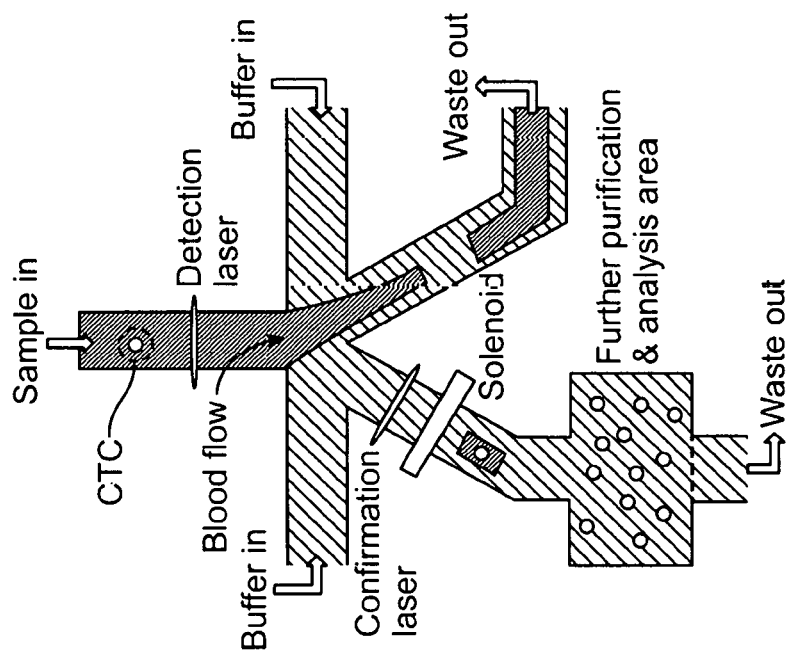
FIG. 1A is an overview of eDAR according to an aspect of the present disclosure.

In some aspects, the hydrodynamic switch can be controlled by a solenoid and the pressure drop in the two side buffer lines. A solenoid can be located in the rare cell collection channel. In some aspects, this solenoid is in the closed position on the left and the "negative" aliquots flow into the waste channel on the right (FIG. 1A). When the solenoid is opened, a pressure drop between the two side channels that contain buffer switches the blood flow from the waste channel to the collection side. This switch can occur in less than 10 milliseconds (e.g., 2-3 ms) to collect rare particles (e.g., cells).

In some aspects, various hydrodynamic sorting schemes can be used. The disclosure provides for eight different hydrodynamic sorting schemes (FIG. 3). The fluid sample (e.g., blood) can be injected from the main channel, shown as the dark black flow. Buffer (light grey color in the microfluidic chip) can flow in the two side channels, rare cells can be collected to the bottom left channel, and the waste can be directed to the bottom right channel. The rectangular blocks represent the solenoid (see "solenoids"). The solenoid can be set to be normally open (N.O.) or normally closed (N.C.), as indicated by a dark grey or light grey block, respectively (FIG. 3).

Channels of the microfluidic chip may intersect at junctions. In some aspects, one channel intersects with a different channel at a junction. In some aspects, one channel intersects with more than one different channels at a junction. In some aspects, one channel intersects with 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 different channels at a junction. In some aspects, more than one channel intersects with a different channel at a junction. In some aspects, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 different channels intersect with one different channel at a junction.

Channels of the microfluidic chip may not intersect at junctions. In some aspects, one channel intersects with a different channel at a location on the microfluidic chip that is not a junction. In some aspects, one channel intersects with more than one different channels at a location on the microfluidic chip that is not a junction. In some aspects, one channel intersects with 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 different channels at a location on the microfluidic chip that is not a junction. In some aspects, more than one channel intersects with a different channel at a location on the microfluidic chip that is not a junction. In some aspects, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 different channels intersect with one different channel at a location on the microfluidic chip that is not a junction.

Solenoids and Regulation of Flow

The eDAR apparatus includes solenoids to control flow of fluid and hydrodynamic sorting schemes. In some aspects, solenoids can be pistons. For example, solenoid pistons are subcomponents of electro-actuated solenoid valves. In some aspects, the electro-actuated solenoid valves can be piezo-electric valves. In some aspects, solenoid pistons can be embedded in the apparatus by molding. In some aspects, solenoids can be valves. For example, the embedded solenoid pistons may be replaced by solenoid valves in fluidic communication via tubings.

In some aspects, the eDAR apparatus can contain one solenoid. In other cases, the eDAR apparatus can contain more than one solenoid. For example, the eDAR apparatus can contain greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids. In some aspects, at least one solenoid can be open. For example, an open solenoid can be used to allow flow to pass from one part of the microfluidic device to a different part of the microfluidic device. In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be open. In some aspects, one part can be the sample entry point. In some aspects, one part can be the waste channel. In some aspects, one part can be a sorting chamber. In some aspects, at least one solenoid can be normally open (N.O.) In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be normally open.

In some aspects, solenoids can be closed. For example, a closed solenoid can be used to prevent flow from passing from one part of the microfluidic device to a different part of the microfluidic device. In some aspects, at least one solenoid can be closed. In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be closed. In some aspects, one part can be the sample entry point. In some aspects, one part can be the waste channel. In some aspects, one part can be a sorting chamber. In some aspects, at least one solenoid can be normally closed (N.C.) In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be normally closed.

In some aspects, solenoids can be switched from open to closed. For example, closing an open solenoid can be used to prevent flow from passing from one part of the microfluidic device to a different part of the microfluidic device. In some aspects, at least one solenoid can be switched from open to closed. In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be switched from open to closed. In some aspects, one part can be the sample entry point. In some aspects, one part can be the waste channel. In some aspects, one part can be a sorting chamber.

In some aspects, solenoids can be switched from closed to open. For example, opening a closed solenoid can be used to allow fluid to pass from one part of the microfluidic device to a different part of the microfluidic device. In some aspects, at least one solenoid can be switched from closed to open. In some aspects, greater than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 solenoids can be switched from closed to open. In some aspects, one part can be the sample entry point. In some aspects, one part can be the waste channel. In some aspects, one part can be a sorting chamber.

In some aspects, the structure of the fluidic microfluidic chip and the corresponding scheme of the hydrodynamic sorting that can be used for eDAR are shown in FIG. 3. The position of the solenoid can be marked when there are outlets or inlets on a single channel. For example in FIG. 3F, the position of the second solenoid can be "center waste," meaning that it is on the center outlet of the waste collection channel. In every scheme, except that shown in FIG. 3G, when the "positive" events can be detected, the DC voltage applied on the solenoids can be changed to trigger the sorting, and after a certain period of time can be returned to the normal state. In some aspects, 4 individual steps can be used to control the sorting (e.g., scheme shown in FIG. 3G). Both solenoids can be closed and the fluid can flow to the waste channel. The sorting can be triggered which could open the solenoid on the collection side to perform the switch-over step. The other solenoid can be opened to perform the switchback step after the cell is collected. Both solenoids can be closed at the same time after the fluid flow was completely switched back to revert to the normal state. A summary of the fluidic configuration and performance of eight different hydrodynamic sorting schemes described herein is depicted in Table 1 (below). In some aspects, two solenoids can be used (e.g., schemes shown in FIGS. 3C, 3E, and 3G).

TABLE 1

Summary of the fluidic configuration and performance of 8 sorting schemes.

| Scheme | Position | Normal state | Left pressure (psi) | Right pressure (psi) | Switch over time (ms) | Switch back time (ms) |
|---|---|---|---|---|---|---|
| a | Collection | Closed | Low | High | ~2-3 | ~15-25 |
| b | Waste | Open | High | Low | ~15-20 | ~2-3 |
| c | Collection Waste | Closed Open | Low | High | ~4-5 | ~10 |
| d | Right Buffer | Close | Low | High | ~3 | ~40 |
| e | Waste | Open | High | Low | ~25 | ~2 |
| f | Collection Center Waste | Closed Open | Low | High | ~25 | ~5-6 |
| g | Collection Center Waste | Closed Closed | Low | High | ~2-3 | ~2-3 |
| h | Center Right Buffer | Closed | Low | High | ~2-3 | ~2-3 |

In some aspects, an off-chip solenoid can be used. The off-chip solenoid can be closed for most of the method. To open the off-chip solenoid, voltage (e.g., 5V DC voltage) can be applied. The off-chip solenoid can open rapidly (e.g., less than or equal to three milliseconds). Where an off-chip solenoid is used, the preparation of the microfluidic chip can be modified and solenoids can be connected with microchannels. In some aspects, an on-chip solenoid can be used. The on-chip solenoid can be closed for most of the method. To open the on-chip solenoid, voltage (e.g., 5V DC voltage) can be applied. The on-chip solenoid can open rapidly (e.g., less than or equal to three milliseconds). Where an on-chip solenoid is used, the preparation of the microfluidic chip can be modified and solenoids can be connected with microchannels.

For example, in this scheme, an off-chip solenoid is used. The labeled fluid sample can be injected into the top channel of the microfluidic chip using a syringe pump (FIG. 4A). Two side channels, where buffer flows through, can be used to control the active sorting step. Two ports are located on the right-side channel, and both are connected to a pressurized buffer source. The off-chip solenoid can be connected to the port near the sorting junction to control the hydrodynamic switch. The switching process using an off-chip solenoid can be stable and can maintain stability through $10^5$ on-off cycles.

In some aspects, an in-line solenoid can be placed on the buffer line to prevent the fluid sample from contacting the solenoid. This can eliminate the possibility of sample decay and cross-contamination. There can be a constant flow of buffer in the rare cell collection channel during use of the eDAR apparatus and method. The on-chip solenoid can improve the efficiency of the subsequent purification (e.g., purification chamber) step and can prevent the formation of aggregates of cells.

In some aspects, the flow of fluid in the eDAR apparatus can be regulated with one of the following either upstream or downstream of the detection volume: a solenoid, a valve, a bubble, an electric field, a magnetic field, an optical field, a pneumatic pressure source, a solid particle, a membrane, an immiscible droplet, a gravitational differential, or a coating to alter surface tension of the channel. The flow of fluid in the eDAR apparatus can be regulated with one of the following either upstream or downstream of the detection volume: a second solenoid, a second valve, a second bubble, a second electric field, a second magnetic field, a second optical field, a second pneumatic pressure source, a second solid particle, a second membrane, a second immiscible droplet, a second gravitational differential, or a second coating to alter surface tension of the channel. The flow can be stopped, decelerated, or accelerated as the cells traverse through the detection volume.

In some aspects, continuous flow of the fluid sample through a flow channel can be maintained during detection. In some aspects, the individual aliquots may not be physically separated, but rather can be defined by an optical detection step and/or a sorting step.

For example, the flow can be directed into the channel that can be used to collect the waste (FIG. 4B). There can be two channels after the sorting junction. The left channel can collect positive aliquots, deliver them to the filtration and collection area for further purification (e.g., purification chamber); the right channel collects waste (e.g., the negative aliquots). In this case, no voltage is applied the solenoid when aliquots are ranked as "negative" and remains closed (FIG. 4B). The change in flow pattern can occur after an initial pressure drop between the No. 1 and 3 buffer sources (FIG. 4A). A positive event can be detected by the first detection window. In this case, a DC voltage (e.g., 5V) can be applied to the solenoid to open the buffer flow from the buffer reservoir (e.g., No. 2). The decreased flow resistance of the buffer channel on the right side can generate a higher flow rate. The fluid flow can be pushed from the right side to the left to collect the positive aliquot (FIG. 4C). The aliquot can be collected and confirmed by the second detection window. In some aspects, the solenoid can be closed to switch the fluid flow back to the waste collection channel (FIG. 4D). The time required for the switch-over and back can be less than 20 milliseconds, in an exemplary case the time is or between 2-3 milliseconds (Table 1 and FIG. 5; frame rate=1,918 frames per second). In some aspects, the conditions used can be repeated for more than $10^5$ on-off cycles.

In some aspects, the flow can be delivered by, for example, methods and devices that induce hydrodynamic fluidic pressure, which includes but is not limited to those that operate on the basis of mechanical principles (e.g., external syringe pumps, pneumatic membrane pumps, vibrating membrane pumps, vacuum devices, centrifugal forces, and capillary action); electrical or magnetic principles (e.g., electroosmotic flow, electrokinetic pumps piezoelectric/ultrasonic pumps, ferrofluidic plugs, electrohydrodynamic pumps, and magnetohydrodynamic pumps); thermodynamic principles (e.g., gas bubble generation/phase-change-induced volume expansion); surface-wetting principles (e.g., electrowetting, chemically, thermally, and radioactively induced surface-tension gradient).

In yet other cases, the fluid can be delivered or channeled by a fluid drive force provided by gravity feed, surface tension (like capillary action), electrostatic forces (electrokinetic flow), centrifugal flow (substrate disposed on a compact disc and rotated), magnetic forces (oscillating ions causes flow), magnetohydrodynamic forces and a vacuum or pressure differential.

In some aspects, fluid flow control devices, such as those enumerated with regard to methods and devices for inducing hydrodynamic fluid pressure or fluid drive force, can be coupled to an input port or an output port of the present subject matter. In some aspects, multiple ports are provided at either or both of the inlet and outlet and one or more ports are coupled to a fluid flow control device.

Transit Time

The analyte (e.g., rare cell or circulating tumor cell (CTC)) can flow from the first detection window to the second detection window. The time that can elapse between recording of the decision APD peak in the first window and detection of the confirmation signal can be the transit time for sorting an analyte. In some aspects, the transit time can vary. In some aspects, the liner flow rate can affect the transit time. In some aspects, the laminar flow of the microchannel can affect the transit time. In some aspects, the volumetric flow rate can be set to 40 μL/min (FIG. 6B). In some aspects, the volumetric flow rates can be about 1 μL/min, 2 μL/min, 3 μL/min, 4 μL/min, 5 μL/min, 6 μL/min, 7 μL/min, 8 μL/min, 9 μL/min, 10 μL/min, 11 μL/min, 12 μL/min, 13 μL/min, 14 μL/min, 15 μL/min, 16 μL/min, 17 μL/min, 18 μL/min, 19 μL/min, 20 μL/min, 21 μL/min, 22 μL/min, 23 μL/min, 24 μL/min, 25 μL/min, 30 μL/min, 35 μL/min, 40 μL/min, 45 μL/min, 50 μL/min, 55 μL/min, 60 μL/min, 651 μL/min, 70 μL/min, 75 μL/min, 80 μL/min, 85 μL/min, 90 μL/min, 95 μL/min, 100 μL/min, or 200 μL/min.

In some aspects, the flow rate can be within the range of about 1 μL/min-5 μL/min, 3 μL/min-10 μL/min, 5 μL/min-5 μL/min, 10 μL/min-20 μL/min, 151 μL/min-30 μL/min, 20 μL/min-40 μL/min, 30 μL/min-50 μL/min, 40 μL/min-60 μL/min, 50 μL/min-70 μL/min, 60 μL/min-80 μL/min, 70 μL/min-90 μL/min, 80 μL/min-100 μL/min, 90 μL/min-100 μL/min or 90 μL/min-200 μL/min. In other cases, the volumetric flow rate can be set to 80 μL/min (FIG. 6B).

In some aspects, the volumetric flow rates can be 1 μL/min, 2 μL/min, 3 μL/min, 41 μL/min, 5 μL/min, 6 μL/min, 7 μL/min, 8 μL/min, 9 μL/min, 10 μL/min, 1 μL/min, 121 μL/min, 13 μL/min, 14 μL/min, 15 μL/min, 16 μL/min, 17 μL/min, 18 μL/min, 19 μL/min, 20 μL/min, 21 μL/min, 221 μL/min, 23 μL/min, 241 μL/min, 25 μL/min, 30 μL/min, 35 μL/min, 40 μL/min, 45 μL/min, 50 μL/min, 55 μL/min, 60 μL/min, 65 μL/min, 70 μL/min, 75 μL/min, 80 μL/min, 85 μL/min, 90 μL/min, 95 μL/min, 100 μL/min, or 200 μL/min.

In some aspects, the flow rate can be within the range of 1 μL/min-5 μL/min, 3 μL/min-10 μL/min, 5 μL/min-15 μL/min, 10 μL/min-20 μL/min, 15 μL/min-30 μL/min, 20 μL/min-40 μL/min, 30 μL/min-50 μL/min, 40)μL/min-60 μL/min, 50 μL/min-70 μL/min, 60 μL/min-80 μL/min, 70 μL/min-90 μL/min, 80 μL/min-100 μL/min, 90 μL/min-100 μL/min or 90 μL/min-200 μL/min. A higher flow rate can be used to achieve a lower transit time (FIG. 6C).

Detection

The disclosure provides an apparatus for eDAR using a microfluidic chip that can be equipped with a detection system. In some aspects, the detection system can include a line-confocal detection scheme. In the line-confocal detection scheme, two laser sources (e.g., 488 and 633 nm) form detection windows (e.g., two) using a series of dichroic mirrors, cylindrical lens and beam splitters. The first detection window can have two laser beams simultaneously overlapping and can be used detect the fluorescence signals from the labeled rare cells (e.g., CTCs). The second detection window can be used to confirm the identity of the rare cells, or lack of rare cells, in the sorted aliquots. The second detection window can further be used to monitor the sorting efficiency.

In some aspects, two rare particles can be detected simultaneously. Each rare particle can be contacted with a unique detection reagent and each detection reagent can be detected by one of two detection devices. Furthermore, wherein the detection reagents comprise fluorescent moieties, two interrogation devices (e.g., two lasers) producing radiation at different wavelengths corresponding to excitation wavelengths of the different fluorescent moieties can be used. The respective fluorescent radiation can be detected by two different detection devices. In some aspects, the detection reagents can be differentiable by fluorescence at different wavelengths.

In some aspects, the two or more rare particles can be detected in series. For example, the method can comprise detecting a first rare particle at a first location of an eDAR apparatus and detecting a second rare cell at a second location of an eDAR apparatus. In this case, the aliquot in which the first and second particle reside can be channeled to a new location after the first detection step, after the second detection step, or after both detection steps.

In certain aspects, the detection event can occur at a regular frequency. The frequency may relate to the size of the detection volume and the flow rate of the fluid sample. The detection volume of a particular apparatus can be within the range of, and including the limits of, 0.1-100 µL (e.g., 10 µL) and the fluid sample can flow through the apparatus at a rate within the range of, and including the limits of, 1-1000 µL/second (e.g., 100 µL/second), a different aliquot can be detected within the range of, and including the limits of, once every 0.001-1 second (e.g., 0.1 seconds), or at a rate within the range of, and including the limits of, 1-100 Hz (e.g., 10 Hz).

In some aspects, the geometry of the apparatus and the volume of the fluid to be processed can affect the rate. For example, aliquots can traverse through the detection volume at a rate within the range of, and including the limits of, 0.1 kHz and 100 MHz. In some aspects, the aliquots traverse through the detection volume at a rate within the range of, and including the limits of, 10 Hz and 10 MHz or about 10 MHz. In some aspects, the aliquots may traverse through the detection volume at a frequency within the range of, and including the limits of, 0.1 kHz and 100 MHz or about 100 MHz, or within the range of, and including the limits of 1 kHz or about 1 kHz and 10 MHz or about 10 MHz, or frequency within the range of, and including the limits of about 1 kHz and 5 MHz or about 5 MHz, or frequency within the range of, and including the limits of 1 kHz or about 1 kHz and 1 MHz or about 1 MHz. In some aspects, the frequency by which the aliquots traverse through the detection volume can be at least about 0.1 kHz, or at least about 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70, 80, 90, 100, 125, 150, 200, 250, 300, 400, 500, 600, 700, 800, or 900 kHz, or at least about 1 MHz, or at least about 2, 3, 4, 5, 6, 7, 8, 9, 10, 15, 20, 25, 30, 35, 40, 45, 50, 60, 70, 80, 90, or 100 MHz. In some aspects, the frequency by which the aliquots traverse through the detection volume can be at least 0.1 kHz, or at least 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70, 80, 90, 100, 125, 150, 200, 250, 300, 400, 500, 600, 700, 800, or 900 kHz, or at least 1 MHz, or at least 2, 3, 4, 5, 6, 7, 8, 9, 10, 15, 20, 25, 30, 35, 40, 45, 50, 60, 70, 80, 90, or 100 MHz.

In some aspects, detection of a characteristic from an ensemble of analytes (e.g., cells) in an aliquot of a fluid sample can be simultaneous or cumulative over time. For example, detection of a characteristic can be simultaneous from a large aliquot containing an ensemble of analytes. During simultaneous mode, the particles can be carried by a flow of variable velocity. In other cases, particles can be carried by a steady flow as they traverse through the detection volume.

In various aspects, the eDAR apparatuses and methods allow a signal to be detected simultaneously from a plurality of analytes (e.g., a plurality of cells). In some aspects, an aliquot is ranked based on a signal detected simultaneously from a plurality of analytes present within the aliquot.

In other cases, the methods herein provide for detection of a characteristic from an ensemble of cells can emanate over time ("cumulative") from a small detection volume which is on the order of a single cell, but with multiple cells traversing through the detection volume with the aid of flow. Cumulative mode of eDAR is distinct from time-lapse overlay of consecutive signals or frames emanating from a single bioparticle; timelapse overlay of a single bioparticle does not constitute an ensemble of bioparticles. In both simultaneous and cumulative, a decision is rendered only after a characteristic from an ensemble of cells has been detected.

In some aspects, the detector is selected from the group consisting of a camera, an electron multiplier, a charge-coupled device (CCD) image sensor, a photomultiplier tube (PMT), an avalanche photodiode (APD), a single-photon avalanche diode (SPAD), a silicon photomultiplier (SiPM), and a complementary metal oxide semiconductor (CMOS) image sensor. In some aspects, the eDAR apparatus provided herein can comprise a photo, electro, acoustical or magnetic detector to track the motion of select cells or to enumerate select particles or cells present in an aliquot.

In some aspects, an apparatus or method provided herein can incorporate fluorescence (single or multi-color) microscopy imaging in various configurations, which include but are not limited to bright-field, epi, confocal, trans, DIC (differential interference contrast), dark-field, Hoffman, or phase-contrast.

In some aspects, the apparatuses provided herein can comprise a plurality of detection devices, for example, at least 2, 3, 4, 5, 6, 7, 8, 9, 10, or more detection devices. Multiple detection devices may be useful for performing the methods of the present disclosure, for example, wherein more than one rare particle or cell is present in a fluid sample, more than one cell marker is being used to differentiate different cell types, or multiple detection reagents are being detected simultaneously. In some aspects, the detection devices can include a confirmatory laser. For example, the confirmatory laser can be used to interrogate the sorted aliquot. In some aspects, the sorted aliquot detected by the confirmatory laser can be a positive aliquot and retained after sorting. In some aspects, the sorted aliquot detected by the confirmatory laser can be a negative aliquot and can be discarded after sorting. For example, the confirmatory laser can be used as a second detection method to control the accuracy of the eDAR sorting scheme.

Sources of Radiation and Devices

The disclosure provides an apparatus for eDAR that can include a detection device or an imaging device and a ranking device (e.g., a computer). In some aspects, a laser (or more than one laser) can serve as an interrogation device. An inverted microscope with photodiodes, photomultipliers, or cameras can be used as a detection device. A mask can be placed in a path between the channel and the detection devices.

In some aspects, the interrogation device (e.g., a 488 nm solid-state diode pumped laser and a 633 nm HeNe laser) can be directed into an inverted microscope. The two laser beams can be shaped using cylindrical optics or diffractive optics to form a collimated elliptical beam with an aspect ratio of 10 to 1 prior to entering the microscope objective. Using a combination of half-waveplate and polarizing beam splitter, the intensity of each beam can be adjusted, while mirrors independently steer the light to create a spatially co-localized excitation region. The fluorescence from bioparticles can be split into three wavelength bands by two dichroic mirrors before passing through the bandpass filters and refocused onto the three single-photon avalanche diodes (SPADs). One SPAD can collect fluorescence in the wavelength range of 560-610 nm, a second SPAD cab collect fluorescence in the range of 645-700 nm, and a third SPAD can collect in the range of 500-540 nm. The SPAD outputs are directed to a digital processor (e.g., computer) with a counter/timer board and analyzed with several algorithms.

In some aspects, a digital processor accepts a signal from the detection device and through an algorithm to rank the aliquot. The digital processor can direct the aliquot into the appropriate channel based on the value of the ranking (e.g., the presence, absence, quantity, identity, or composition of rare particles in the fluid sample). eDAR can comprise one, two, three, four, five or six detection devices and one, two, three, four, five or six interrogation devices, or multitudes of detection devices and interrogation devices.

Dual Capture eDAR

This disclosure further provides an apparatus for a "dual-capture" version of eDAR. The dual-capture apparatus can separate two different subpopulations of rare cells from the same sample of mixed fluid. This can be performed on a single microfluidic chip simultaneously. The two subpopulations can further be trapped separately on two different regions on the microfluidic chip.

Figure 8:
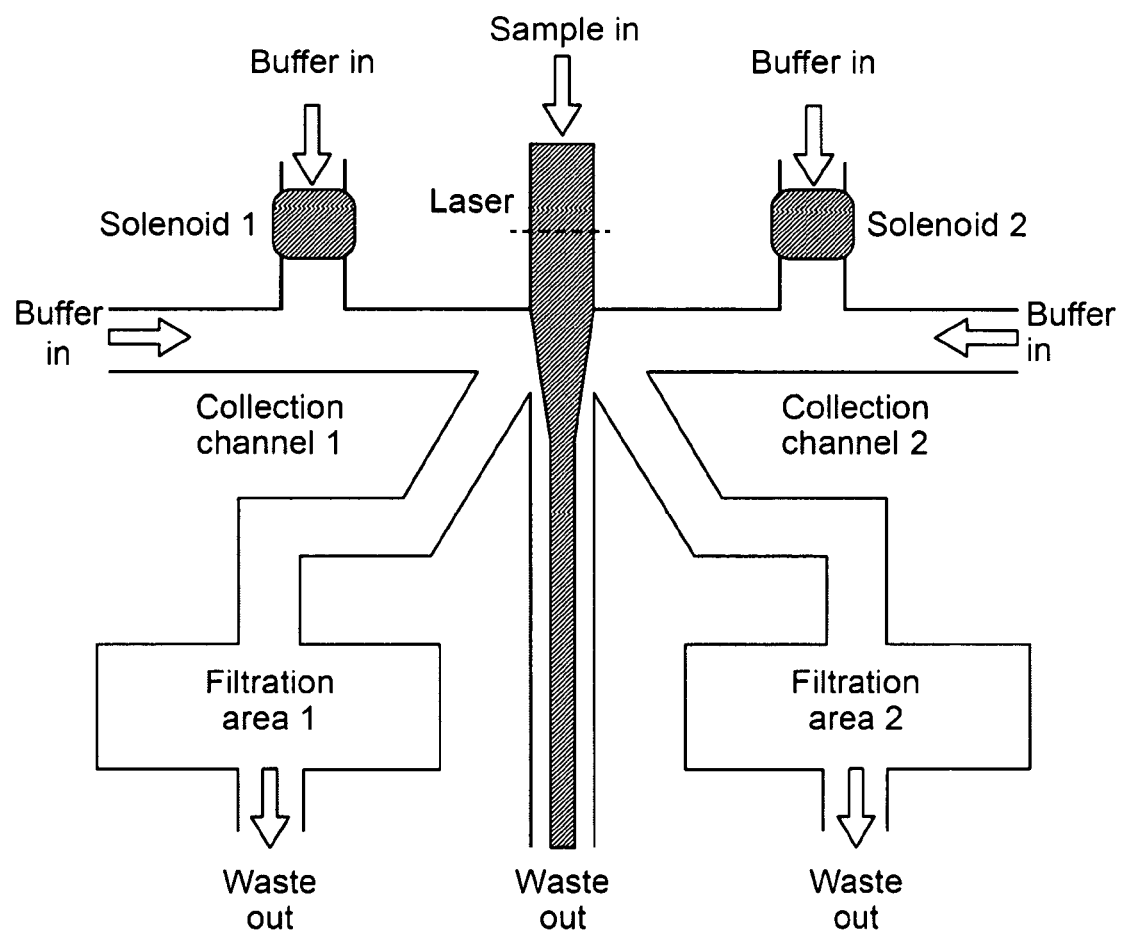
FIG. 8 depicts the general structure of the "dual-capture" eDAR according to an aspect of the present disclosure.

A general structure of the dual capture version of the microfluidic eDAR device is depicted in FIG. 8. Samples can be labeled with at least two unique antibodies that are conjugated to unique fluorescent tags. For example, the sample (e.g, blood) can be labeled with a first tag conjugated with a unique fluorophore that binds to a marker (e.g., epithelial, anti-EpCAM-PE) on an analyte within the sample and a second tag conjugated with a unique fluorophore that binds to a marker (e.g., mesenchymal, anti-EGFR or anti-vimentin) on an analyte within the sample where each fluorophore can have a different wavelength of emission (e.g., FITC). The labeled blood sample can be injected into the microfluidic chip. The rare cells which express EpCAM can be detected using the line-confocal scheme (described before) and the peak can be detected in the yellow channel. A sorting event can be triggered to collect that particular aliquot into a collection channel (e.g., collection channel #1). In some aspects, the aliquot can be ranked as positive to a mesenchymal markers then the rare cell can be sorted in to a different collection channel (e.g., collection channel #2). The two subpopulations of rare cells can be separately trapped and enriched on the dual-capture eDAR microfluidic chip.

The dual-capture eDAR apparatus can use a fluidic switching scheme (FIG. 8). The labeled sample can be introduced into the main channel on the top. Buffer can flow in the two side channels to control the hydrodynamic switching of the blood flow using two solenoids. In some aspects, the filtration area of the dual-capture eDAR can be built using microslits (described before). Two subpopulations of CTCs can be separated and trapped on two different filtration areas on the same microfluidic chip.

Figure 9A:
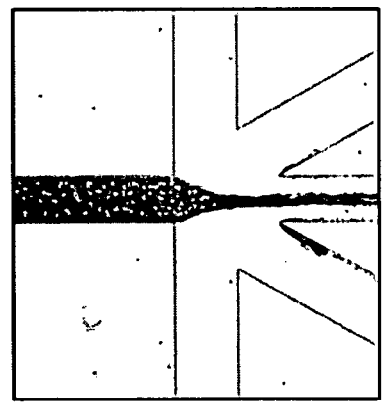
FIGS. 9A-9C shows bright field images of flow switching in accordance with some embodiments of the present disclosure.
Figure 9B:
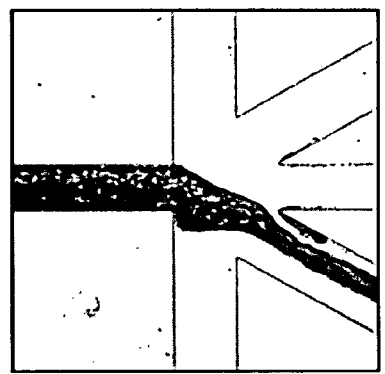
Figure 9C:
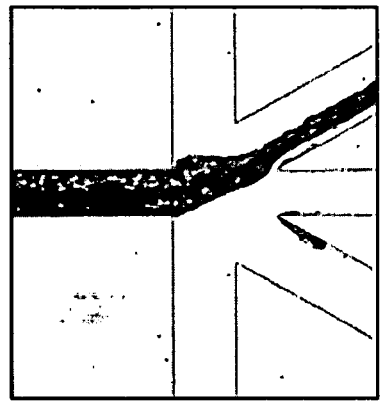

The dual-capture eDAR apparatus can include solenoids. In some aspects, both of the solenoids can be closed when aliquots are ranked as negative (FIG. 9). The sample can flow to the bottom center channel to collect as waste if the pressure is balanced in both channels. In other cases, when the aliquots are ranked positive with respect to only one of the two markers (e.g., epithelial) then solenoid #2 can be opened for the sample to flow into the collection channel on the left (FIG. 9B). After the aliquot is collected, solenoid #2 can be closed again and the flow of the sample is returned to the center channel. In some aspects, the aliquots can be ranked as positive to only one marker (e.g., epithelial) and solenoid #1 can be opened to allow flow of the sample to the right channel (FIG. 9C). In some aspects, the response time for the two types of sorting events in the dual-capture eDAR apparatus is quick (e.g., less than or equal to 3 milliseconds).

Dispersion

Figure 19:
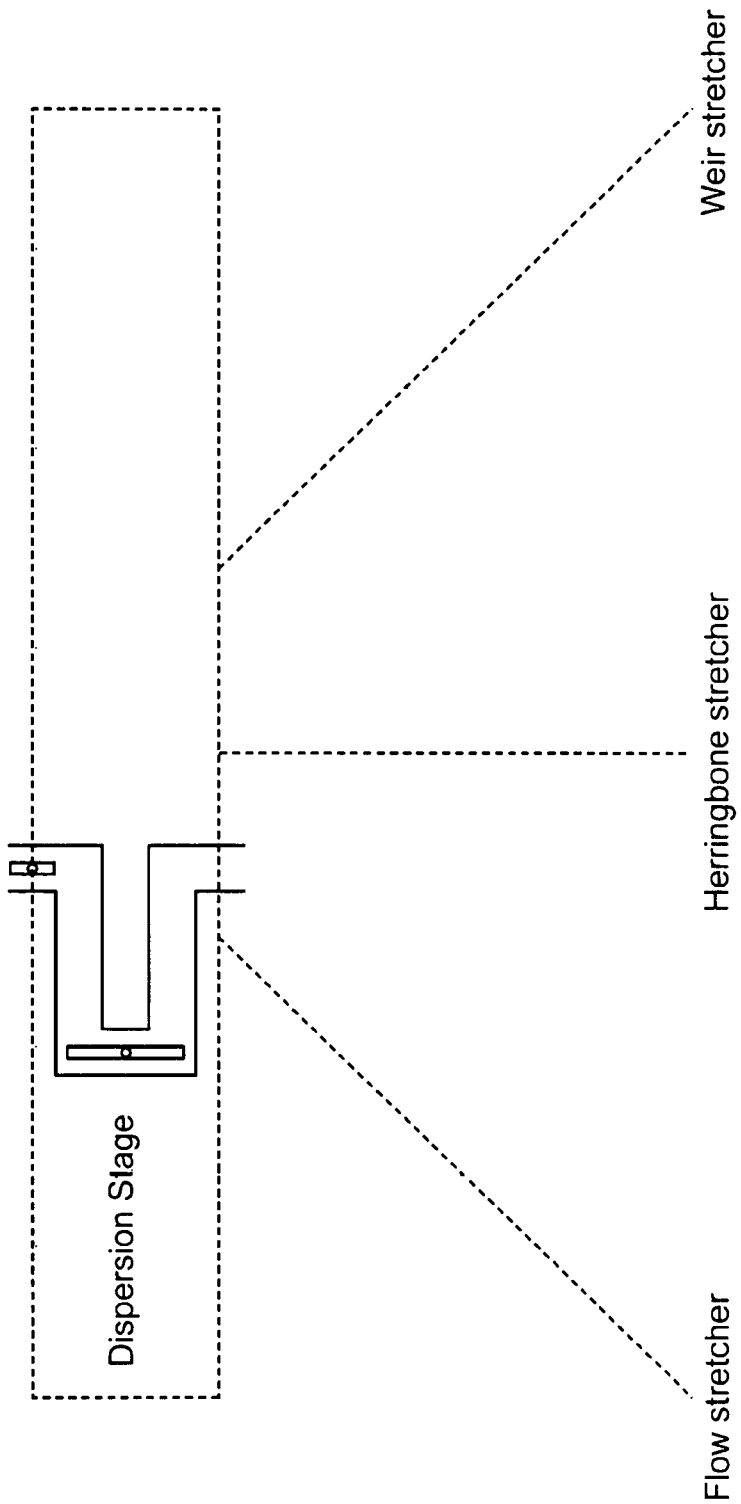
FIG. 19 shows exemplary dispersion stages.

FIG. 19 shows exemplary dispersion stages. The dispersion stage may comprise a flow stretcher, as described herein. The dispersion stage may comprise the use of parabolic flow profile to disperse the cells. The dispersion stage may comprise flowing cells down multiple flow paths to disperse the cells. The dispersion stage may comprise a herringbone stretcher, as described herein. The dispersion stage may comprise a weir stretcher, as described herein.

A dispersion stage, as described herein, can be used to form a dispersed sample from a sample (e.g., an undispersed sample, a first isolated sample, a second isolated sample, etc.) or portion thereof. A dispersed sample can be a sample in which two or more components of the sample are segregated or dispersed. For example, a dispersion stage can be used to physically segregate or disperse two types or populations of cells of a sample comprising 2, 3, 4, 5, 6, 7, 8, 9, 10, or more than 10 types or populations of cells.

A dispersed volume can comprise a dispersed sample. For example, a fluid volume comprising a sample (or portion thereof) can be passed to a dispersion stage (e.g., from a first sorting stage) and the sample (or portion of a sample) can be dispersed as it passes through the dispersion stage. A fluid volume comprising a dispersed sample (e.g., after having passed through a dispersion stage) can be a dispersed volume.

In some cases, the two or more components of the sample segregated or dispersed in a dispersed sample can be components of the same fluid volume or they can be components of different fluid volumes (e.g., a plurality of fluid volumes formed from a single fluid volume during dispersion of the sample). A fluid volume comprising a sample can form two or more dispersed fluid volumes when it is dispersed (e.g., in a dispersion stage). In some cases, two or more dispersed volumes are separated or segregated from each other by a discontinuity in the fluid between the two or more dispersed volumes. For example, two dispersed volumes formed from a single fluid volume as the fluid volume passes through a dispersion stage can be separated from one another (e.g., in a channel) by a second fluid, such as a gas or immiscible fluid.

Flow Stretching

Figure 20A:
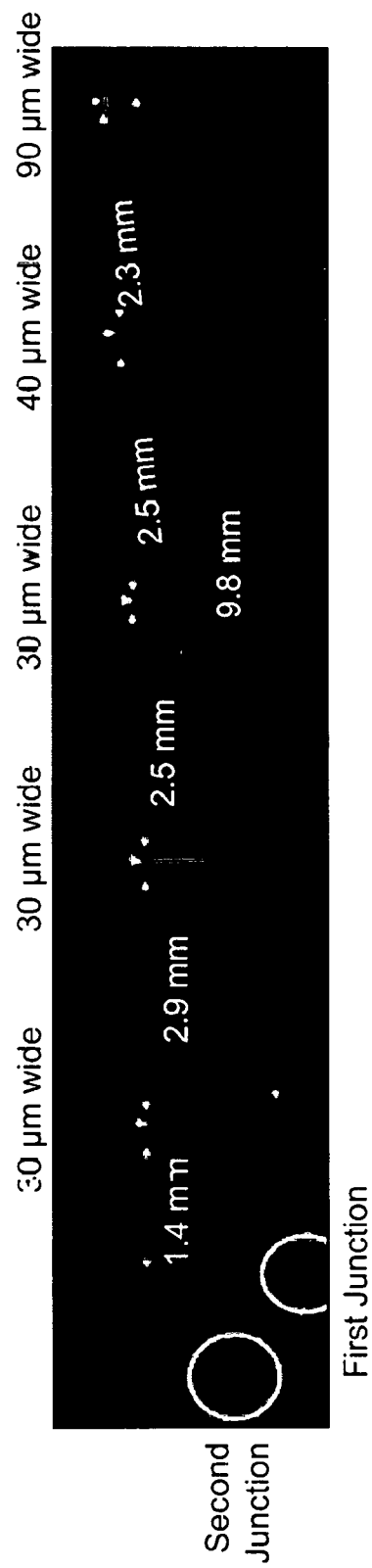
FIG. 20A shows a top view of an exemplary flow stretcher.

FIG. 20A shows a top view of an exemplary flow stretcher. The flow stretcher may comprise one or more straight flow sections. For instance, the flow stretcher may comprise a first straight flow section in which portions of the aliquot or fluid containing the particle flows to the right, as shown in the upper part of FIG. 20A. The flow stretcher may comprise a second straight flow section in which portions of the aliquot or fluid volume containing to the particle travels to the left at a downward angle, as shown in the middle and lower parts of FIG. 20A. The flow stretcher may comprise any number of straight flow sections traveling in any direction. The straight flow sections may have a width of less than 10 microns, less than 20 microns, less than 50 microns, less than 100 microns, less than 200 microns, less than 500 microns, or less than 1,000 microns. The straight flow sections may have a width that is within a range defined by any two of the preceding values.

The straight flow sections may stretch the aliquot or fluid volume containing the particle by imparting a flow distribution to the aliquot or fluid volume. That is, different portions of the aliquot or fluid volume may flow at different rates through the straight flow sections, leading to an overall lengthening of the aliquot or fluid volume containing the particle to be collected. The straight flow sections may impart a lateral flow distribution to the aliquot or fluid volume, such that the flow rates vary across the width of the straight flow sections. The straight flow sections may impart a parabolic flow distribution to the aliquot or fluid volume. The straight flow sections may have a height of less than 10 microns, less than 20 microns, less than 50 microns, less than 100 microns, less than 200 microns, less than 500 microns, or less than 1,000 microns. The straight flow sections may have a height that is within a range defined by any two of the preceding values. The straight flow sections may have a width of less than 10 microns, less than 20 microns, less than 50 microns, less than 100 microns, less than 200 microns, less than 500 microns, or less than 1,000 microns. The straight flow sections may have a width that is within a range defined by any two of the preceding values.

Herringbone Flow Stretching

Figure 20B:
FIG. 20B shows a top view of an exemplary herringbone flow stretcher.

FIG. 20B shows a top view of an exemplary herringbone flow stretcher, combined with straight flow sections. The herringbone flow stretcher may comprise one or more straight flow sections. For instance, the herringbone flow stretcher may comprise a first straight flow section in which the aliquot or fluid volume containing the particle flows to the right, as shown in the upper part of FIG. 20B. The straight flow sections may be similar to the straight flow sections described with respect to FIG. 20A. The herringbone flow stretcher may comprise one or more herringbone flow sections. For instance, the herringbone flow stretcher may comprise a herringbone flow section in which the aliquot or fluid volume containing the particle travels to the left at a downward angle, as shown in the middle and lower parts of FIG. 20B. The herringbone flow stretcher may comprise any number of straight flow sections traveling in any direction and any number of herringbone flow sections traveling in any direction. The herringbone flow sections may have a width of less than 10 microns, less than 20 microns, less than 50 microns, less than 100 microns, less than 200 microns, less than 500 microns, or less than 1,000 microns. The herringbone flow sections may have a width that is within a range defined by any two of the preceding values.

The herringbone flow sections may comprise one or more herringbone structures (v-like structures, as shown in FIG. 20B). The herringbone flow sections may comprise 1, 2, 5, 10, 20, 50, 100, or more than 100 herringbone structures. The herringbone flow sections may comprise a number of herringbone structures that is within a range defined by any two of the preceding values. Each herringbone flow section may have the same number of herringbone structures. Each herringbone flow section may have a different number of herringbone structures. The herringbone structures may have a width of less than 10 microns, less than 20 microns, less than 50 microns, less than 100 microns, less than 200 microns, less than 500 microns, or less than 1,000 microns. The herringbone structures may have a width that is within a range defined by any two of the preceding values. Each herringbone structure may be separated from other herringbone structures by a distance of less than 10 microns, less than 20 microns, less than 50 microns, less than 100 microns, less than 200 microns, less than 500 microns, or less than 1,000 microns. Each herringbone structure may be separated from other herringbone structures by a distance that is within a range defined by any two of the preceding values.

The herringbone flow sections may stretch the aliquot or fluid volume containing the particle to be collected by imparting chaotic mixing to the aliquot or fluid volume. The herringbone flow sections may have a height of less than 10 microns, less than 20 microns, less than 50 microns, less than 100 microns, less than 200 microns, less than 500 microns, or less than 1,000 microns. The herringbone flow sections may have a height that is within a range defined by any two of the preceding values.

Weir Stretching

FIG. 21A shows a top view of an exemplary weir stretcher. The weir stretcher may comprise one or more straight flow sections. For instance, the weir stretcher may comprise a first straight flow section in which the aliquot or fluid volume containing the particle flows to the right, as shown in the upper part of FIG. 21A. The straight flow sections may be similar to the straight flow sections described with respect to FIG. 21A. The weir stretcher may comprise one or more weir sections. For instance, the weir stretcher may comprise a weir section in which the aliquot or fluid volume containing the particle at a downward angle, as shown in the middle and lower parts of FIG. 21A. The weir stretcher may comprise any number of straight flow sections traveling in any direction and any number of weir sections traveling in any direction. The weir sections may have a width of less than 10 microns, less than 20 microns, less than 50 microns, less than 100 microns, less than 200 microns, less than 500 microns, or less than 1,000 microns. The weir sections may have a width that is within a range defined by any two of the preceding values.

The weir sections may comprise one or more weir structures (flow sections containing a plurality of posts for structural support, as shown in FIG. 21A). The weir sections may comprise 1, 2, 5, 10, 20, 50, 100, or more than 100 weir structures. The weir sections may comprise a number of weir structures that is within a range defined by any two of the preceding values. Each Weir section may have the same number of weir structures. Each weir section may have a different number of herringbone structures. The weir structures may have a width of less than 10 microns, less than 20 microns, less than 50 microns, less than 100 microns, less than 200 microns, less than 500 microns, or less than 1,000 microns. The herringbone structures may have a width that is within a range defined by any two of the preceding values. The weir structures may have a length of less than 10 microns, less than 20 microns, less than 50 microns, less than 100 microns, less than 200 microns, less than 500 microns, less than 1,000 microns, less than 2,000 microns, less than 5,000 microns, or less than 10,000 microns. The weir structures may have a width that is within a range defined by any two of the preceding values. Each weir structure may be separated from other weir structures by a distance of less than 10 microns, less than 20 microns, less than 50 microns, less than 100 microns, less than 200 microns, less than 500 microns, less than 1,000 microns, less than 2,000 microns, less than 5,000 microns, or less than 10,000 microns. Each weir structure may be separated from other weir structures by a distance that is within a range defined by any two of the preceding values.

The weir sections may stretch the particle by imparting different degrees of resistance to cell movement based on the cell size, shape, or deformability. The weir sections may have a height of less than 10 microns, less than 20 microns, less than 50 microns, less than 100 microns, less than 200 microns, less than 500 microns, or less than 1,000 microns. The weir sections may have a height that is within a range defined by any two of the preceding values.

FIG. 21B shows a top view of an exemplary long weir stretcher. The weir stretcher may comprise a single long weir section. The long weir section may be similar to any of the weir sections described with reference to FIG. 21A.

Figure 22A:
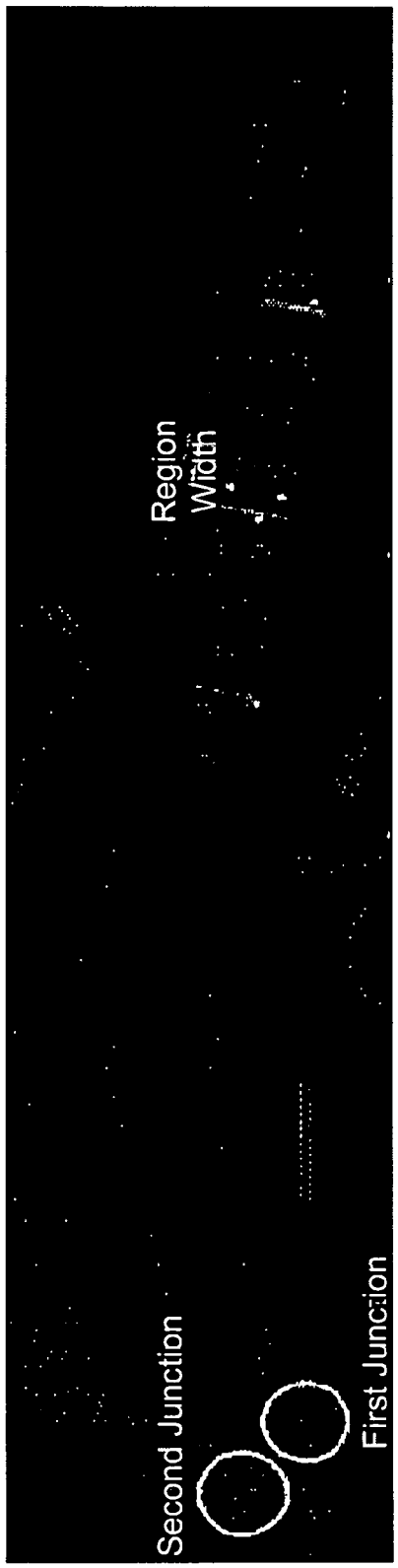
FIGS. 22A-22C show top views of exemplary two-dimensional weir and filter stretchers.
Figure 22B:
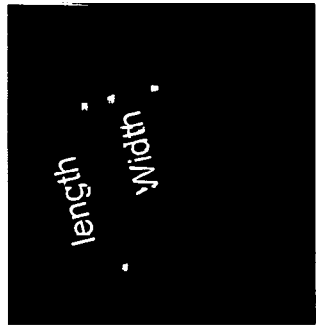
Figure 22C:
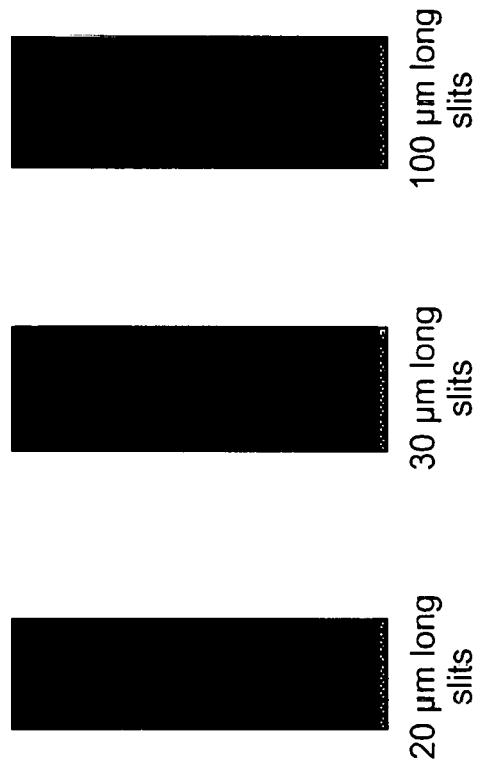

FIG. 22 shows a top view of an exemplary barrier or filter based cell stretcher.

Flow Stretching by Obstacles or Multiple Flow Paths

FIG. 11 shows a top view of an exemplary first sorting stage connected to a second sorting stage with a dispersion stage comprising a channel containing obstacles or multiple flow paths of varying designs.

FIG. 11A shows a dispersion stage comprise a plurality of obstacles within a wide flow channel. As shown in FIG. 11A, the first sorting stage may perform a first sorting, as described herein. The first sorting stage may pass an aliquot or fluid volume to a dispersion stage comprising a plurality of obstacles within a wide flow channel. The dispersion stage may comprise 1, 2, 3, 4, 5, 6, 7, 8, 9, 10, or more than 10 wide flow channels. For instance, the dispersion stage may comprise 1 wide flow channel, as shown in FIG. 11A. The obstacles may have a circular shape, as shown in FIG. 11A. The obstacles may have an ovular shape, a square shape, a rectangular shape, a pentagonal shape, a hexagonal shape, or any other shape. The obstacles may increase or decrease the fluid path length for one or more sub-volumes of the aliquot or fluid volume. The different path lengths experienced by different sub-volumes of the aliquot or fluid volume may increase the average distance between particles in the various sub-volumes. For instance, the distance between a particle to be collected and other particles of the aliquot or fluid volume may be increased. The obstacles may be posts that extend along a height of the flow channel. The posts may provide support to the channel and may help to prevent the channel from collapsing under the weight of the materials used to construct the channel. The dispersion stage may pass the dispersed volume to the second sorting stage. The second sorting stage may perform a second sorting, as described herein.

FIG. 11B shows a dispersion stage comprising a plurality of branching locations. As shown in FIG. 11B, the first sorting stage may perform a first sorting, as described herein. The first sorting stage may pass an aliquot or fluid volume to a dispersion stage comprising a plurality of branching locations in the channel. The dispersion stage may comprise 1, 2, 3, 4, 5, 6, 7, 8, 9, 10, or more than 10 branching locations. For instance, the dispersion stage may comprise 4 branching locations, as shown in FIG. 11B. At each branching location, different sub-volumes of the aliquot or fluid volume may take different flow paths. For instance, a first sub-volume may take a flow path consisting of (from top to bottom in FIG. 11B): left, right, left, right. A second sub-volume may take flow path consisting of: right, left, right, left. The first sub-volume may take a longer path than the second sub-volume. The first sub-volume may therefore take a longer time to travel from the first sorting stage to the second sorting stage than the second sub-volume. Any sub-volume of the aliquot or fluid volume may take any possible path. The plurality of branching locations may increase or decrease the fluid path length for one or more sub-volumes of the aliquot or fluid volume. The different path lengths experienced by different sub-volumes of the aliquot or fluid volume may increase the average distance between particles in the various sub-volumes. For instance, the distance between a particle to be collected and other particles of the aliquot or fluid volume may be increased. The branches may comprise posts (shown as half-circles in FIG. 11B) that extend along a height of the flow channel. The posts may provide support to the channel and may help to prevent the channel from collapsing under the weight of the materials used to construct the channel. The dispersion stage may pass the dispersed volume to the second sorting stage. The second sorting stage may perform a second sorting, as described herein.

FIG. 11C shows a dispersion stage comprising a plurality of flow sections that subsequently widen and narrow. As shown in FIG. 11C, the first sorting stage may perform a first sorting, as described herein. The first sorting stage may pass an aliquot or fluid volume to a dispersion stage comprising a plurality of flow sections that subsequently widen and narrow. The dispersion stage may comprise 1, 2, 3, 4, 5, 6, 7, 8, 9, 10, or more than 10 flow sections that subsequently widen and narrow. For instance, the dispersion stage may comprise 3 flow sections that subsequently widen and narrow, as shown in FIG. 11C. The flow sections that widen and narrow may have a diamond-like shape, as shown in FIG. 11C. The flow sections may have a circular shape, an ovular shape, a square shape, a rectangular shape, a pentagonal shape, a hexagonal shape, or any other shape. The flow sections may increase or decrease the fluid path length for one or more sub-volumes of the aliquot or fluid volume. The different path lengths experienced by different sub-volumes of the aliquot or fluid volume may increase the average distance between particles in the various sub-volumes. For instance, the distance between a particle to be collected and other particles of the aliquot or fluid volume may be increased. The sections that subsequently widen and narrow may further comprise posts that extend along a height of the flow channel (shown as circles in FIG. 11C). The posts may provide support to the channel and may help to prevent the channel from collapsing under the weight of the materials used to construct the channel. The dispersion stage may pass the dispersed volume to the second sorting stage. The second sorting stage may perform a second*sorting, as described herein.

FIG. 11D shows a dispersion stage comprising a plurality of multiple branching channels. As shown in FIG. 11D, the first sorting stage may perform a first sorting, as described herein. The first sorting stage may pass an aliquot or fluid volume to a dispersion stage comprising a plurality of multiple branching locations in the channel. Each multiple branching location may comprise 1, 2, 3, 4, 5, 6, 7, 8, 9, 10, or more than two branches. For instance, each multiple branching may comprise 4 branches, as shown in FIG. 11D. The dispersion stage may comprise 1, 2, 3, 4, 5, 6, 7, 8, 9, 10, or more than 10 multiple branching locations. For instance, the dispersion stage may comprise 2 multiple branching locations, as shown in FIG. 11D. At each multiple branching location, different sub-volumes of the aliquot or fluid volume may take multiple different flow paths. For instance, a first sub-volume may take a flow path consisting of (from top to bottom in FIG. 11D): rightmost, rightmost. A second sub-volume may take flow path consisting of: leftmost, leftmost. The first sub-volume may take a longer path than the second sub-volume. The first sub-volume may therefore take a longer time to travel from the first sorting stage to the second sorting stage than the second sub-volume. Any sub-volume of the aliquot or fluid volume may take any possible path. The plurality of multiple branching locations may increase or decrease the fluid path length for one or more sub-volumes of the aliquot or fluid volume. The different path lengths experienced by different sub-volumes of the aliquot or fluid volume may increase the average distance between particles in the various sub-volumes. For instance, the distance between a particle to be collected and other particles of the aliquot or fluid volume may be increased. The branches may comprise posts (shown as generally kidney-shaped in FIG. 11D) that extend along a height of the flow channel. The posts may provide support to the channel and may help to prevent the channel from collapsing under the weight of the materials used to construct the channel. The dispersion stage may pass the dispersed volume to the second sorting stage. The second sorting stage may perform a second sorting, as described herein.

FIG. 12 shows a top view of an exemplary first sorting stage connected to a second sorting stage with a channel of different geometries.

Figure 12A:
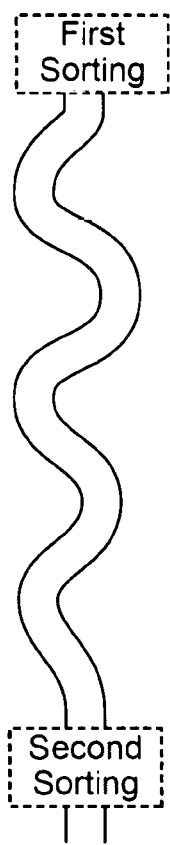
FIGS. 12A-12C show top views of an exemplary first sorting stage connected to a second sorting stage with a channel of different geometries.

FIG. 12A shows a dispersion stage comprising a plurality of curved flow sections forming a serpentine channel. As shown in FIG. 12A, the first sorting stage may perform a first sorting, as described herein. The first sorting stage may pass an aliquot or fluid volume to a dispersion stage comprising a plurality of curved flow sections that form an overall serpentine shape. The dispersion stage may comprise 1, 2, 3, 4, 5, 6, 7, 8, 9, 10, or more than 10 curved sections. For instance, the dispersion stage may comprise 5 curved sections, as shown in FIG. 12A. The curved sections may increase or decrease the fluid path length for one or more sub-volumes of the aliquot or fluid volume. The different path lengths experienced by different sub-volumes of the aliquot or fluid volume may increase the average distance between particles in the various sub-volumes. For instance, the distance between a particle to be collected and other particles of the aliquot or fluid volume may be increased. The dispersion stage may pass the dispersed volume to the second sorting stage. The second sorting stage may perform a second sorting, as described herein.

Figure 12B:
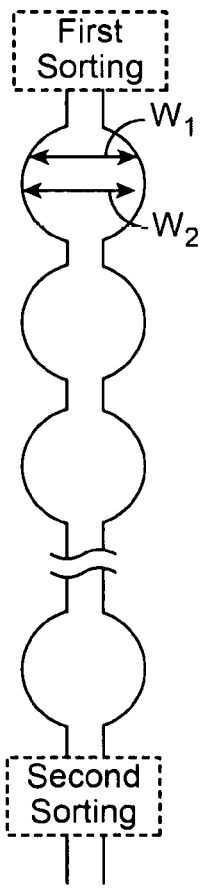

FIG. 12B shows a dispersion stage comprising a plurality of flow sections that subsequently widen and narrow connected by a plurality of straight flow sections. As shown in FIG. 12B, the first sorting stage may perform a first sorting, as described herein. The first sorting stage may pass an aliquot or fluid volume to a dispersion stage comprising a plurality of flow sections that subsequently widen and narrow connected by a plurality of straight flow sections. The dispersion stage may comprise 1, 2, 3, 4, 5, 6, 7, 8, 9, 10, or more than 10 flow sections that subsequently widen and narrow. For instance, the dispersion stage may comprise 4 flow sections that subsequently widen and narrow, as shown in FIG. 12B. The flow sections that widen and narrow may have a circular shape, as shown in FIG. 12B. The flow sections that widen and narrow may have an ovular shape, a square shape, a rectangular shape, a pentagonal shape, a hexagonal shape, or any other shape. The flow sections that widen and narrow may have a width (e.g., a flow section may widen from width "$w_1$" at a first longitudinal location to width "$w_2$" at a second longitudinal position, as shown in FIG. 12B) that varies over the length of the flow sections that widen and narrow. The flow sections that widen and narrow may increase or decrease the fluid path length for one or more sub-volumes of the aliquot or fluid volume. The different path lengths experienced by different sub-volumes of the aliquot or fluid volume may increase the average distance between particles in the various sub-volumes. For instance, the distance between a particle to be collected and other particles of the aliquot or fluid volume may be increased. The dispersion stage may pass the dispersed volume to the second sorting stage. The second sorting stage may perform a second sorting, as described herein.

Figure 12C:
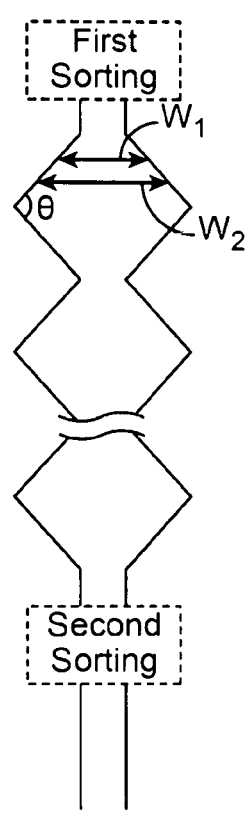

FIG. 12C shows a dispersion stage comprising a plurality of flow sections that subsequently widen and narrow. As shown in FIG. 12C, the first sorting stage may perform a first sorting, as described herein. The first sorting stage may pass an aliquot or fluid volume to a dispersion stage comprising a plurality of flow sections that subsequently widen and narrow. The dispersion stage may comprise 1, 2, 3, 4, 5, 6, 7, 8, 9, 10, or more than 10 flow sections that subsequently widen and narrow. For instance, the dispersion stage may comprise 3 flow sections that subsequently widen and narrow, as shown in FIG. 12C. The flow sections that widen and narrow may have a generally diamond-like shape, as shown in FIG. 12C. The flow sections may have a width ("w", as shown in FIG. 12C) that varies over the length of the flow sections (e.g., a flow section may widen from width "$w_1$" at a first longitudinal location to width "$w_2$" at a second longitudinal position). In this cases of diamond-like flow sections, two sides of the diamond may meet at any angle ($\theta$, as shown in FIG. 12C). The angle may be greater than 0 degrees. The angle may be less than 180 degrees. The flow sections may increase or decrease the fluid path length for one or more sub-volumes of the aliquot or fluid volume. The different path lengths experienced by different sub-volumes of the aliquot or fluid volume may increase the average distance between particles in the various sub-volumes. For instance, the distance between a particle to be collected and other particles of the aliquot or fluid volume may be increased. The dispersion stage may pass the dispersed volume to the second sorting stage. The second sorting stage may perform a second sorting, as described herein.

Multiple Dispersion Strategies

The dispersion stage may combine two or more of the dispersion strategies described herein. For instance, the dispersion stage may combine 2, 3, 4, 5, 6, 7, 8, 9, 10, or more than 10 of the dispersion strategies. The dispersion stage may combine the dispersion strategies in any possible combination and any possible order.

Figure 13:
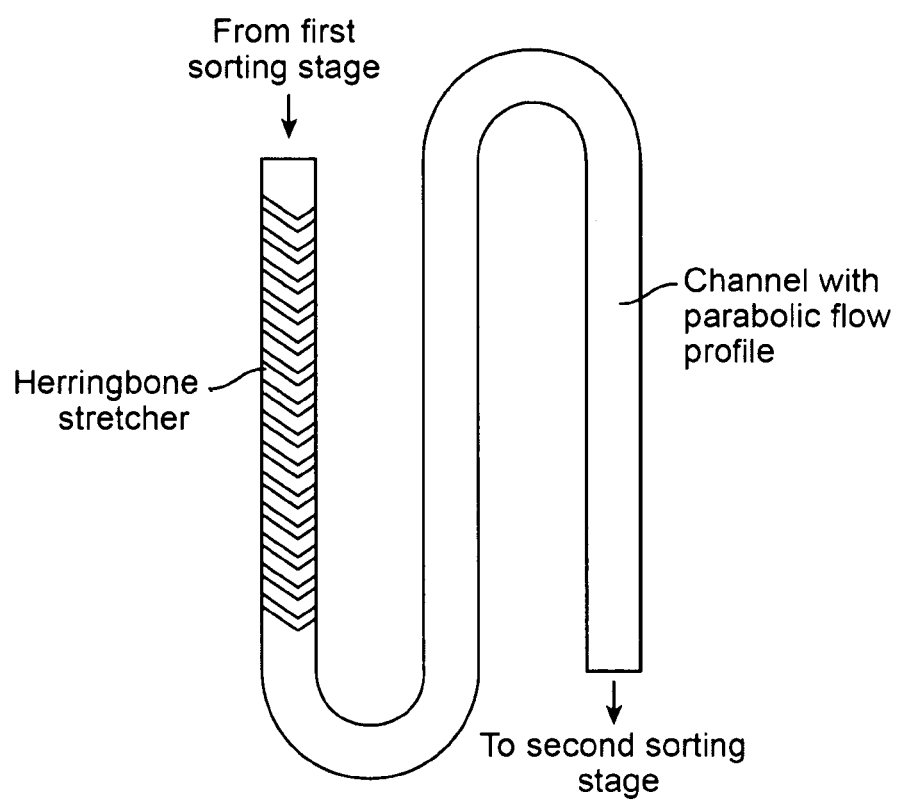
FIG. 13 shows a top view of an exemplary herringbone stretcher combined with a straight channel with a parabolic flow profile.

FIG. 13 shows a top view of an exemplary herringbone stretcher combined with a straight channel with a parabolic flow profile. The herringbone stretcher may be similar to any herringbone stretcher described herein, such as a herringbone stretcher described herein with respect to FIG. 20B. The straight channel may be similar to any straight channel described herein, such as a straight channel described herein with respect to FIG. 20A. The herringbone stretcher and straight channel may occur in any possible order.

Figure 14:
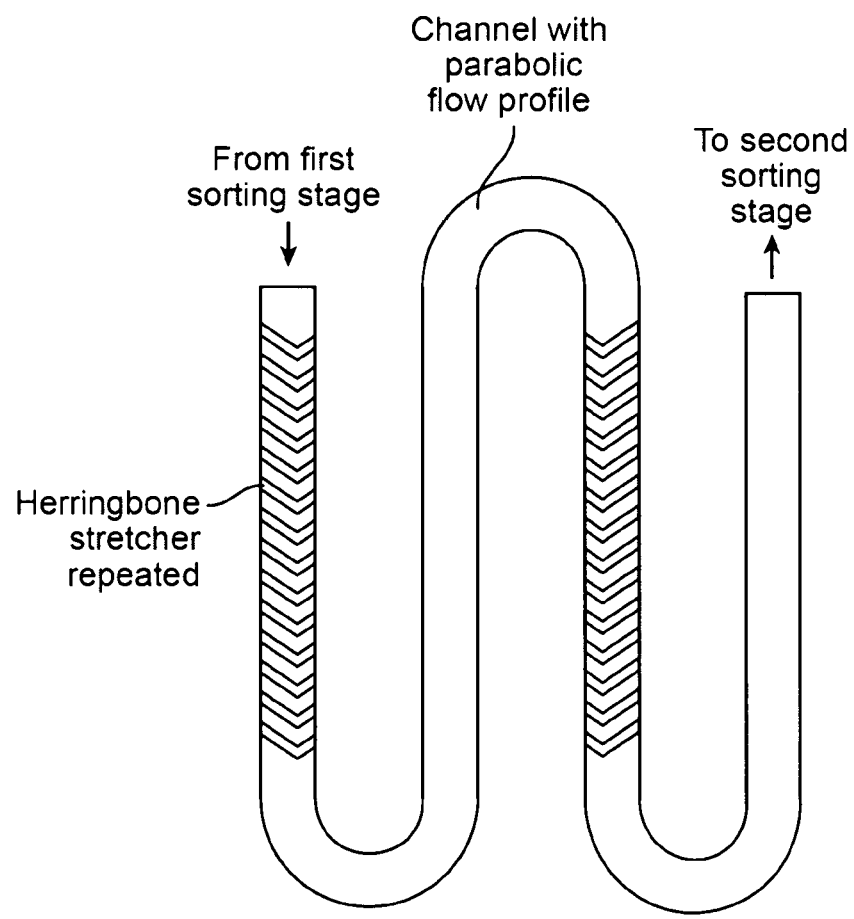
FIG. 14 shows a top view of exemplary multiple herringbone stretchers combined with multiple straight channels.

FIG. 14 shows a top view of exemplary multiple herringbone stretchers combined with multiple straight channels. The device may comprise 2, 3, 4, 5, 6, 7, 8, 9, 10, or more than 10 herringbone stretchers. Each herringbone stretcher may be similar to any herringbone stretcher described herein, such as a herringbone stretcher described herein with respect to FIG. 20B. The device may comprise 2, 3, 4, 5, 6, 7, 8, 9, 10, or more than 10 straight channels. Each straight channel may be similar to any straight channel described herein, such as a straight channel described herein with respect to FIG. 20A. The herringbone stretchers and straight channels may occur in any possible order.

Figure 15:
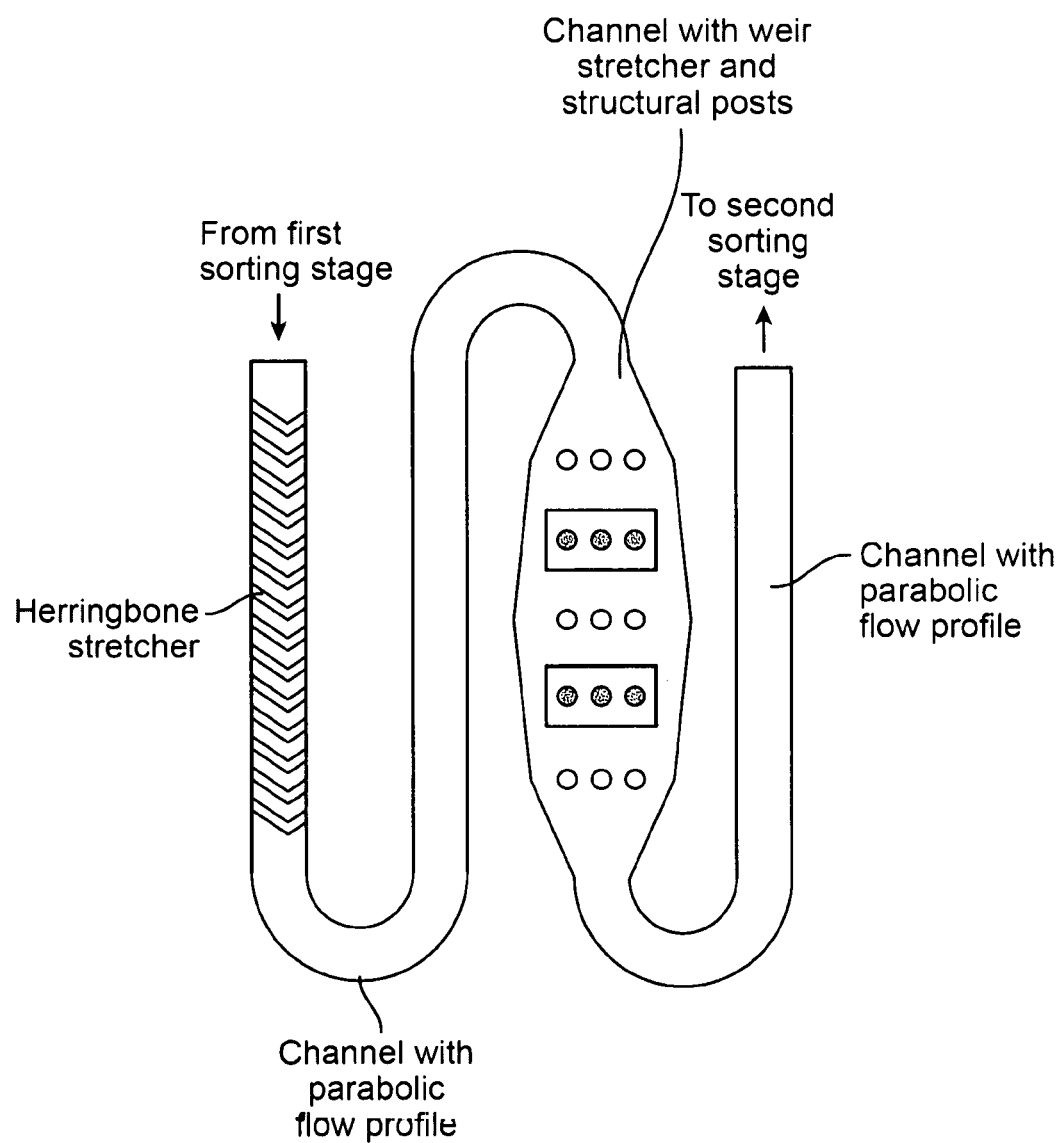
FIG. 15 shows a top view of an exemplary herringbone stretcher, combined with a straight channel and a weir stretcher.

FIG. 15 shows a top view of an exemplary herringbone stretcher combined with a straight channel and a weir stretcher. The weir stretch may further comprise structural posts. The structural posts may prevent channel collapse, as described herein. The device may comprise 2, 3, 4, 5, 6, 7, 8, 9, 10, or more than 10 herringbone stretchers. Each herringbone stretcher may be similar to any herringbone stretcher described herein, such as a herringbone stretcher described herein with respect to FIG. 20B. The device may comprise 2, 3, 4, 5, 6, 7, 8, 9, 10, or more than 10 straight channels. Each straight channel may be similar to any straight channel described herein, such as a straight channel described herein with respect to FIG. 20A. The device may comprise 2, 3, 4, 5, 6, 7, 8, 9, 10, or more than 10 weir stretchers. Each weir stretcher may be similar to any weir stretcher described herein, such as a weir stretcher described herein with respect to FIG. 21A. The herringbone stretchers, straight channels, and weir stretchers may occur in any possible order.

Figure 16:
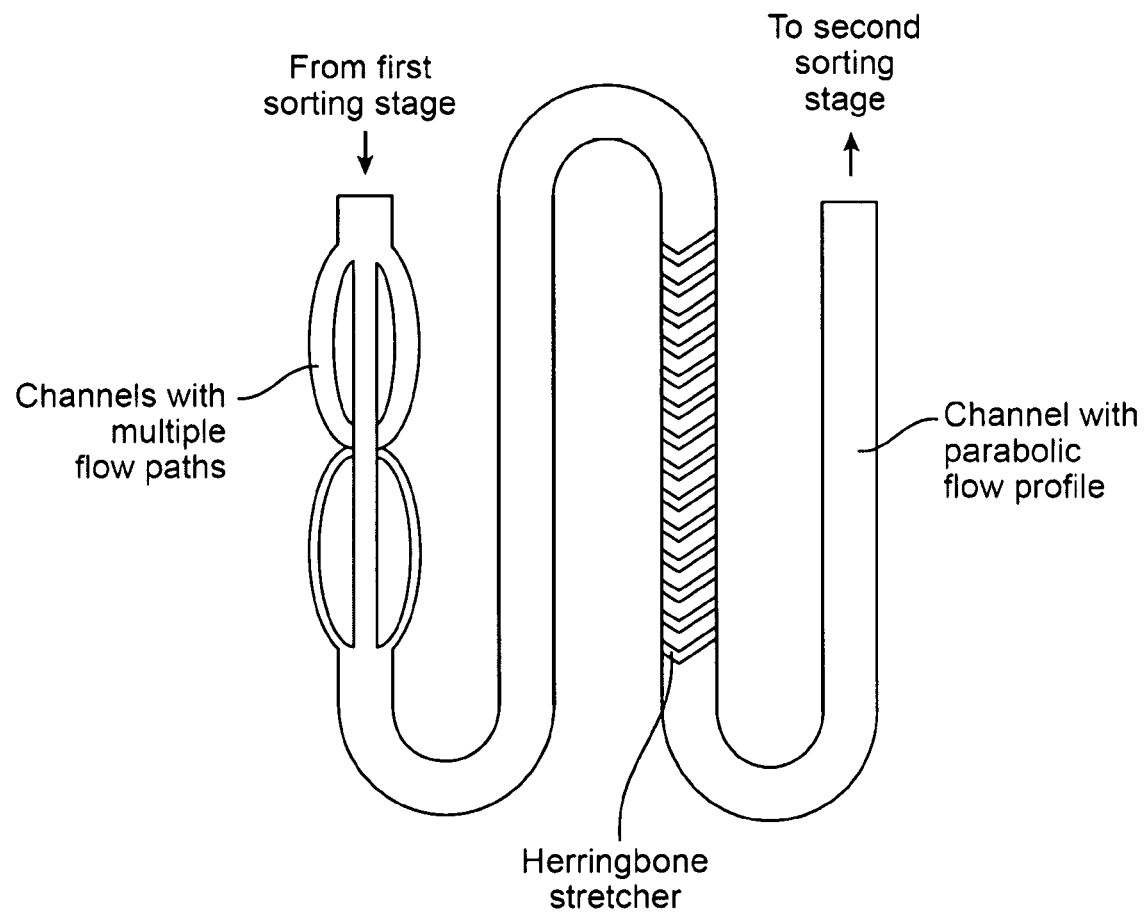
FIG. 16 shows a top view of an exemplary flow stretcher with multiple fluid paths combined with a herringbone stretcher.

FIG. 16 shows a top view of an exemplary flow stretcher with multiple fluid paths combined with a herringbone stretcher. The device may comprise 2, 3, 4, 5, 6, 7, 8, 9, 10, or more than 10 multiple fluid path sections. Each multiple fluid path section may be similar to any multiple fluid path described herein, such as a multiple fluid path described herein with respect to FIG. 11D. The device may comprise 2, 3, 4, 5, 6, 7, 8, 9, 10, or more than 10 herringbone stretchers. Each herringbone stretcher may be similar to any herringbone stretcher described herein, such as a herringbone stretcher described herein with respect to FIG. 20B. The multiple fluid path sections and herringbone stretchers may occur in any possible order.

Figure 17:
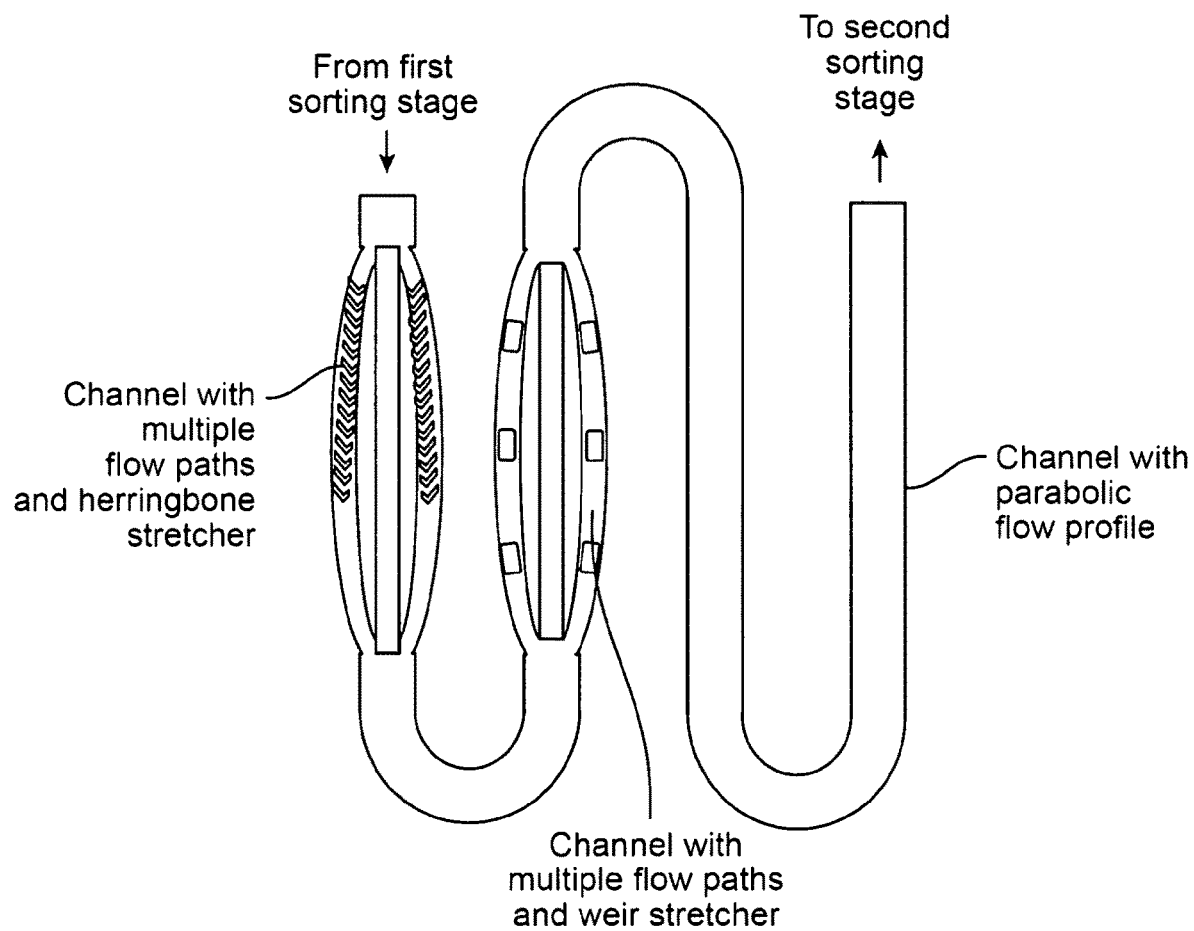
FIG. 17 shows a top view of an exemplary flow stretcher with multiple fluid paths combined with multiple herringbone stretchers and weir stretchers.

FIG. 17 shows a top view of an exemplary flow stretcher with multiple fluid paths combined with multiple herringbone stretchers and weir stretchers. The device may comprise 2, 3, 4, 5, 6, 7, 8, 9, 10, or more than 10 multiple fluid path sections. Each multiple fluid path section may be similar to any multiple fluid path described herein, such as a multiple fluid path described herein with respect to FIG. 11D. The device may comprise 2, 3, 4, 5, 6, 7, 8, 9, 10, or more than 10 herringbone stretchers. Each herringbone stretcher may be similar to any herringbone stretcher described herein, such as a herringbone stretcher described herein with respect to FIG. 20B. The device may comprise 2, 3, 4, 5, 6, 7, 8, 9, 10, or more than 10 weir stretchers. Each weir stretcher may be similar to any weir stretcher described herein, such as a weir stretcher described herein with respect to FIG. 21A. The multiple fluid path sections, herringbone stretchers, and weir stretchers may occur in any possible order.

Flow Stretching Microdevices

Figure 23A:
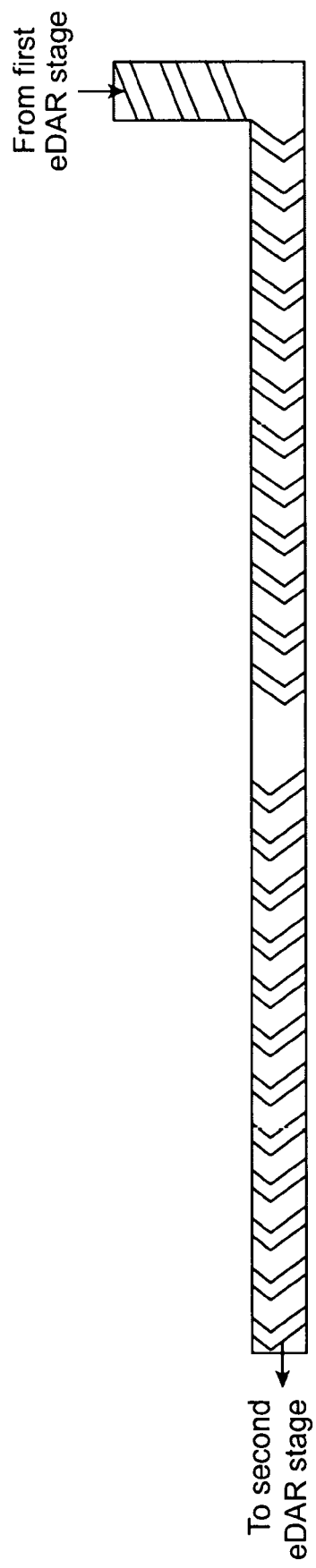
FIG. 23A shows a schematic of a flow path through a microfluidic device utilizing herringbone structures.

FIG. 23A shows a schematic of a flow path through a microfluidic device utilizing herringbone structures. An aliquot or fluid volume containing a particle may enter a herringbone section along a flow channel from the first eDAR stage. The aliquot or fluid volume may encounter one or more herringbone flow sections. For instance, the aliquot or fluid volume may encounter a first herringbone flow section comprising a plurality of straight herringbone structures, as shown in the upper right of FIG. 23A. The aliquot or fluid volume may then encounter a second herringbone section comprising a plurality of v-shaped herringbone structures offset from the center of a flow channel, as shown in the bottom right of FIG. 23A. The aliquot or fluid volume may then encounter a third herringbone section comprising a plurality of v-shaped herringbone structures offset from the center of the flow channel in the opposite direction from the second herringbone section. The herringbone sections and structures may be any herringbone sections and structures as described herein.

Figure 23B:
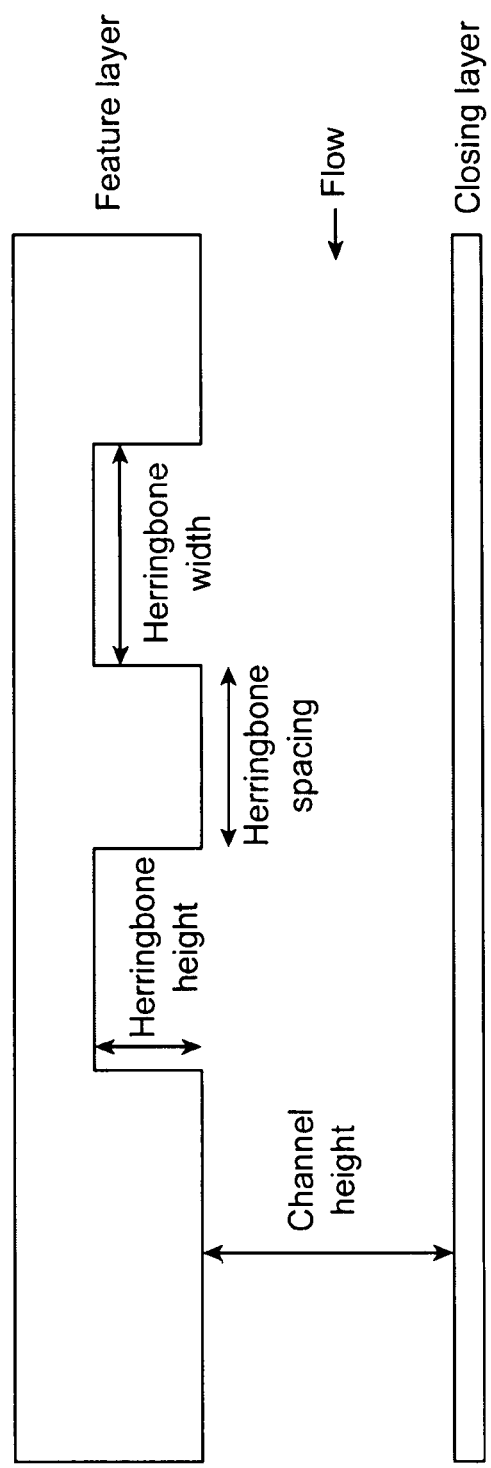
FIG. 23B shows a side view of the layers of a flow channel in a microfluidic device utilizing herringbone structures.

FIG. 23B shows a side view of the layers of a flow channel in a microfluidic device utilizing herringbone structures. The microfluidic device may comprise a feature layer and a closing layer. The feature layer and the closing layer may be separated by a flow channel. The flow channel may have a height less than 10 microns, less than 20 microns, less than 50 microns, less than 100 microns, less than 200 microns, less than 500 microns, or less than 1,000 microns. The flow channel may have a height that is within a range defined by any two of the preceding values. The feature layer may comprise polydimethylsiloxane (PDMS). The PDMS feature layer may be produced using soft lithography techniques. The feature layer may comprise a cured photoresist, such as SUS. The feature layer may be produced using photolithography techniques. The feature layer may comprise silicon. The feature layer may be produced using semiconductor etching techniques, such as wet etching, alkaline etching, dry etching, reactive ion etching, or deep reactive ion etching. The feature layer may comprise glass. The feature layer may be produced using glass etching techniques, such as hydrofluoric acid etching. The feature layer may comprise a plastic, such as a cyclo-olefin copolymer (COC), cyclo-olefin polymer (COP), or polymethylmethylacrylate (PMMA). The feature layer may be produced using imprint lithography. The feature layer may be produced using injection molding. The feature layer may be produced using 3D printing techniques. The feature layer may be produced using any microfluidic production method described herein.

The feature layer may comprise one or more herringbone structures. The herringbone structures may comprise a plurality of wells and ridges. The herringbone structures may be any of the herringbone structures described herein.

The closing layer may be sealed to the feature layer using one or more bonding techniques. The closing layer may comprise glass. The glass closing layer may be sealed to a PDMS feature layer using plasma bonding techniques. The glass closing layer may be sealed to a glass feature layer using fusion bonding techniques. The glass closing layer may be sealed to a silicon feature layer using fusion bonding techniques or anodic bonding techniques. The closing layer may comprise a plastic, such as COC, COP, or PMMA. The plastic closing layer may be sealed to a plastic feature layer using fusion bonding techniques. The plastic closing layer may be sealed to a plastic feature layer using solvent bonding techniques.

Figure 10E:
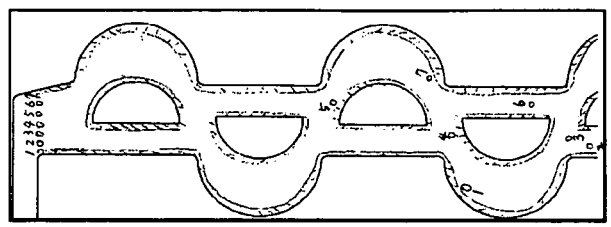
FIG. 10A shows a multi-stage sorting apparatus comprising a first eDAR stage, a dispersion stage, and a second stage of fluorescence activated sorting.
FIG. 10B shows an exemplary second sorting stage.
FIG. 10C shows an exemplary first sorting stage.
FIGS. 10D and E show a portion of a dispersion stage flow stretcher between the first and second sorting stage.
Figure 10D:
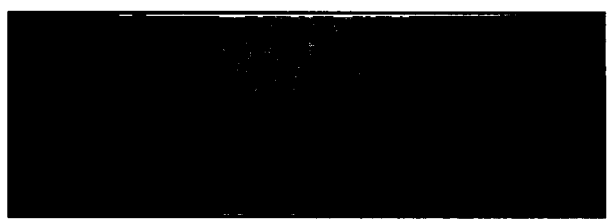
Figure 10C:
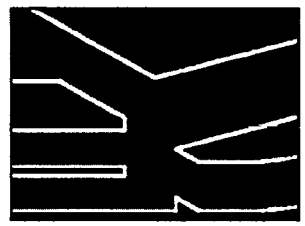
Figure 10B:
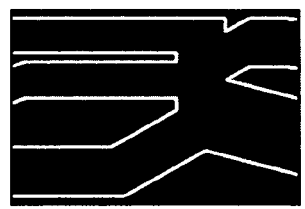
Figure 10A:
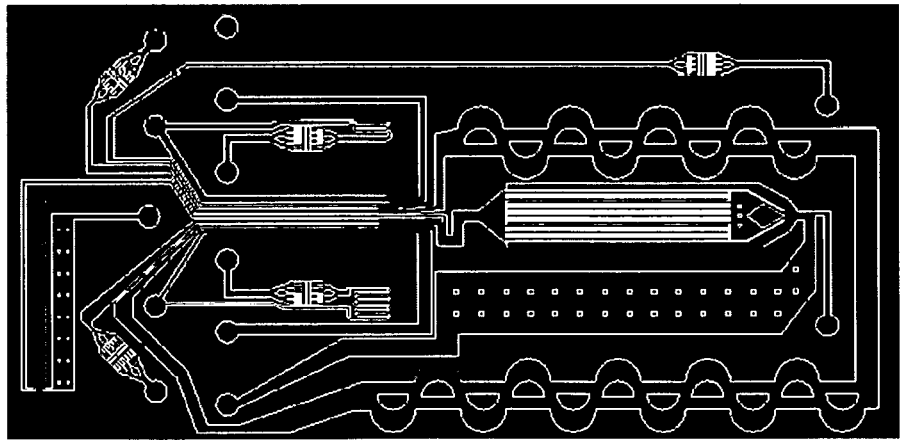

FIG. 10A shows a top view of an exemplary multi-stage fluorescence activated sorting apparatus. The multi-stage apparatus may be a microfluidic apparatus, as described herein. The multi-stage apparatus may comprise a first sorting stage utilizing the eDAR sorting principle described herein. The multi-stage apparatus may further comprise a dispersion stage following the eDAR stage, as described herein. The dispersion stage may comprise a flow stretcher, as described herein. The multi-stage apparatus may further comprise a second sorting stage following the dispersion stage, as described herein. The second sorting stage may be a fluorescence activated sorting stage, as described herein.

FIG. 10C shows an exemplary first sorting stage. The first sorting stage may be an eDAR stage, as described herein. For instance, the first sorting stage may be similar to the first eDAR stage described herein with respect to FIG. 18A.

FIG. 10B shows an exemplary second sorting stage. The second sorting stage may be any fluorescence activated sorting stage described herein. For instance, the second sorting stage may be similar to the second sorting stage described herein with respect to FIG. 18A.

FIGS. 10D and E show a portion of a dispersion stage comprising a flow stretcher between the first sorting stage and the second sorting stage. As shown in FIG. 10E, a plurality of particles (labeled as 1, 2, 3, 4, 5, 6, and 7 in FIG. 10E, though the plurality may comprise 8 particles, 9 particles, 10 particles, more than 10 particles, more than 20 particles, more than 50 particles, more than 100 particles, more than 200 particles, more than 500 particles, more than 1,000 particles, or a number of particles that is within a range defined by any two of the preceding values) may flow through the dispersion stage. The flow stretcher may act on the fluid flow such that particles (such as the particles labeled 1 through 7 at the top of the flow stretcher in FIG. 10E) end up at different positions after a given amount of time spent flowing through the flow stretcher. Thus, the particles may arrive at the second sorting stage at different points in time. In the example shown in FIG. 10E, particle 2 may arrive at the second sorting stage, followed by particle 3, then particle 6, then particle 1, then particle 4, then particle 7, then particle 5. The flow stretcher may act on the fluid such that the particles arrive at the second sorting stage in any possible order and in any possible amounts of time. The different times of arrival may increase the amount of distance between any two particles. Thus, the particles may be sorted independently due to the increased distance.

Cell Stretching

Stretching in the dispersion stage may also comprise cell stretching. The cell stretching may be imparted by a barrier in a flow channel. The barrier may alter the velocity of the particle contained in the aliquot or fluid volume (such as a cell) based on a physical attribute of the particle. For instance, the barrier may alter the velocity of the particle based on its volume, shape, or deformability. When the particle is a cell, the barrier may alter the velocity of the cell based on the cell volume, cell shape, or cell deformability. The barrier may comprise a filter structure, a weir structure, or a constriction/reduction in cross-sectional dimension in the channel. In some cases, the dispersion stage may utilize flow stretching and cell stretching.

Second Separation

Following dispersion, the particle to be collected may be further separated from other particles contained in the aliquot or fluid volume using a separation procedure (e.g., a separation technique). In a preferred embodiment, the particle to be collected may be subjected to a second eDAR process. A second eDAR process may further separate particle(s) or cell(s) to be collected, as described herein.

A separation procedure (e.g, a second separation) can be an active separation procedure or a passive separation procedure. A second separation procedure (e.g., a separation procedure that is performed after a first separation, such as eDAR) can be performed on an isolated sample or a dispersed sample (e.g., a sample that has been subjected to a first separation or to a first separation and a dispersion procedure).

The particle to be collected may be further separated from other particles (e.g., following a first separation, such as eDAR, and/or a dispersion procedure, such as one performed by passing the particle(s) or cell(s) through a dispersion stage) using a passive separation procedure. In some cases, passive separation can comprise a dispersion procedure. A passive separation comprising a dispersion procedure can comprise passing the particle(s) or cell(s) (e.g., of an isolated sample or a dispersed sample) through a dispersion stage. In some cases, a passive separation comprises the use of a herringbone stretcher, a weir, a channel (or a portion of a channel) comprising multiple flow paths, and/or a channel having dimensions capable of producing parabolic flow in a fluid at flow rates described herein.

The particle to be collected may be further separated from other particles (e.g., after a first separation) using an active separation procedure. For example, a separation procedure (e.g., a second separation procedure) can comprise fluorescence activated sorting. In some cases, fluorescence activated sorting can comprise sorting a single cell in a fluid volume or a group of cells in a fluid volume. Fluorescence activated sorting may include sorting a small group of cells in a fluid volume, which may not be in the form of an aliquot (e.g., fluorescence activated sorting may comprise sorting a small group of cells that are not randomly dispersed in a fluid volume, as can be the case in eDAR), or sorting single cells. The second separation, which can be a second fluorescence activated sorting, may concentrate the particle to be collected into a smaller volume than the aliquot produced by the first separation procedure, which can comprise eDAR sorting. In this manner, the second stage fluorescence activated sorting may further increase the purity of the aliquot or fluid volume containing the particle to be collected as compared to the aliquot produced by the first eDAR stage. Optionally and either alternatively or additionally, the particle to be collected may be further separated from other particles using other separation techniques. A particle to be collected may be further separated after a first separation (e.g., a first eDAR sorting performed in an eDAR sorting stage of an apparatus) by employing a flow cytometry operation or technique. The flow cytometry operation may be a fluorescence activated cell sorting (FACS) operation, which can comprise sorting a plurality of particles or cells of an isolated sample or dispersed sample on a single-particle or single-cell basis. The flow cytometry operation may separate the target particle to be collected from non-target particles by flowing a dispersed aliquot or fluid volume containing both the target particle and non-target particle through a flow cell. The flow cell may align the aliquot or fluid volume so that particles flow single file through the flow cell. The flow cell may be configured such that the distance between two particles is significantly larger than the diameter of the particles.

While in the flow cell, the aliquot or fluid volume may be illuminated with one or more light sources. From instance, the aliquot or fluid volume may be illuminated with one or more lasers. Light emitted by the light sources may interact with the target particle and non-target particles. For instance, light emitted by the light sources may induce fluorescence of the target particle or non-target particles. Particles may be autofluorescent. In this case, the fluorescence may arise from an interaction between the light and an endogenous component of the particle. The particles may be tagged with a fluorescent molecule. In this case, the fluorescence may arise from an interaction between the light and an exogenous fluorophore which has been attached to the particle. The exogenous fluorophore may be attached to the particle based on a physical or chemical property of the particle. For instance, an exogenous fluorophore may be attached to a cell by targeting the exogenous fluorophore that is covalently bound to an antibody to a corresponding surface antigen of the cell. Different fluorophore may bind to different types of particles. In this manner, different types of particles may be distinguished by differing fluorescence signals. The fluorescence interaction may be detected by an optical detector (such as a photodiode) and processed by a processor.

The flow cell may be configured to produce small droplets of liquid from the aliquot or fluid volume. For instance, the flow cell may comprise a vibrating mechanism that produces small droplets. The vibrating mechanism may be configured to produce droplets that contain zero or one particle per droplet. The vibrating mechanism may be configured to produce droplets that contain more than one particle with a very low probability.

The droplets may pass a device that places an electric charge on the droplet. For instance, the droplets may pass a charging ring. The electric charge placed on the droplet may be dependent on the fluorescence signal detected by the optical detector and processed by the processor. For instance, a target particle may give rise to a fluorescence signal when illuminated by light of a specific color, while a non-target particle may not give rise to the fluorescence signal when illuminated by light of that color. Thus, a different charge may be placed on a droplet containing a target particle than the charge placed on a droplet containing a non-target particle. The charged droplets may pass through an electric field, where they may be deflected based on their charge. For instance, a droplet containing a target particle may be deflected in one direction based on its charge, while a droplet containing a non-target particle may be deflected in a different direction based on its differing charge. The droplets may be collected, for instance in one or more vials or well plates.

The separation procedure (e.g., a separation operation) may comprise a magnetic separation operation. The separation operation may comprise magnetic-activated cell sorting (MACS). The magnetic separation operation may utilize magnetic particles to separate target particles from non-target particles. The magnetic particles may comprise superparamagnetic particles. The magnetic particles may comprise superparamagnetic microparticles. The magnetic particles may comprise superparamagnetic nanoparticles. The magnetic particles may be configured to tag target particles or non-target particles. The magnetic particles may be attached to the particle based on a physical or chemical property of the particle. For instance, magnetic particles may be attached to a cell by targeting magnetic particles that are covalently bound to an antibody to a corresponding surface antigen of the cell. The magnetic particles may be configured to bind to target particles. Alternatively, the magnetic particles may be configured to bind to non-target particles. The particles may be passed through a column. The column may be located within a magnetic field. Particles which have been tagged with magnetic particles may stick to column due to interactions with the magnetic field. Particles which have not been tagged may pass through the column. If target particles have been tagged, they may be collected by placing a collection container, such as a vial or well plate, at the end of the column and turning off the magnetic field after the non-target particles have been allowed to pass through the column. If target particles have not been tagged, they may be collected by placing a collection container at the end of the column during the magnetic separation operation.

Multi-Stage Fluorescence Activated Sorting after First-Stage eDAR Sorting

This disclosure further provides an apparatus for a multi-stage fluorescence activated sorting following a first stage of eDAR that utilizes a dispersive separation stage between each set of fluorescence activated sorting and the first eDAR stage. The apparatus can provide further purification of samples compared to a single-stage eDAR apparatus. The apparatus can be performed on a single microfluidic chip.

Figure 18A:
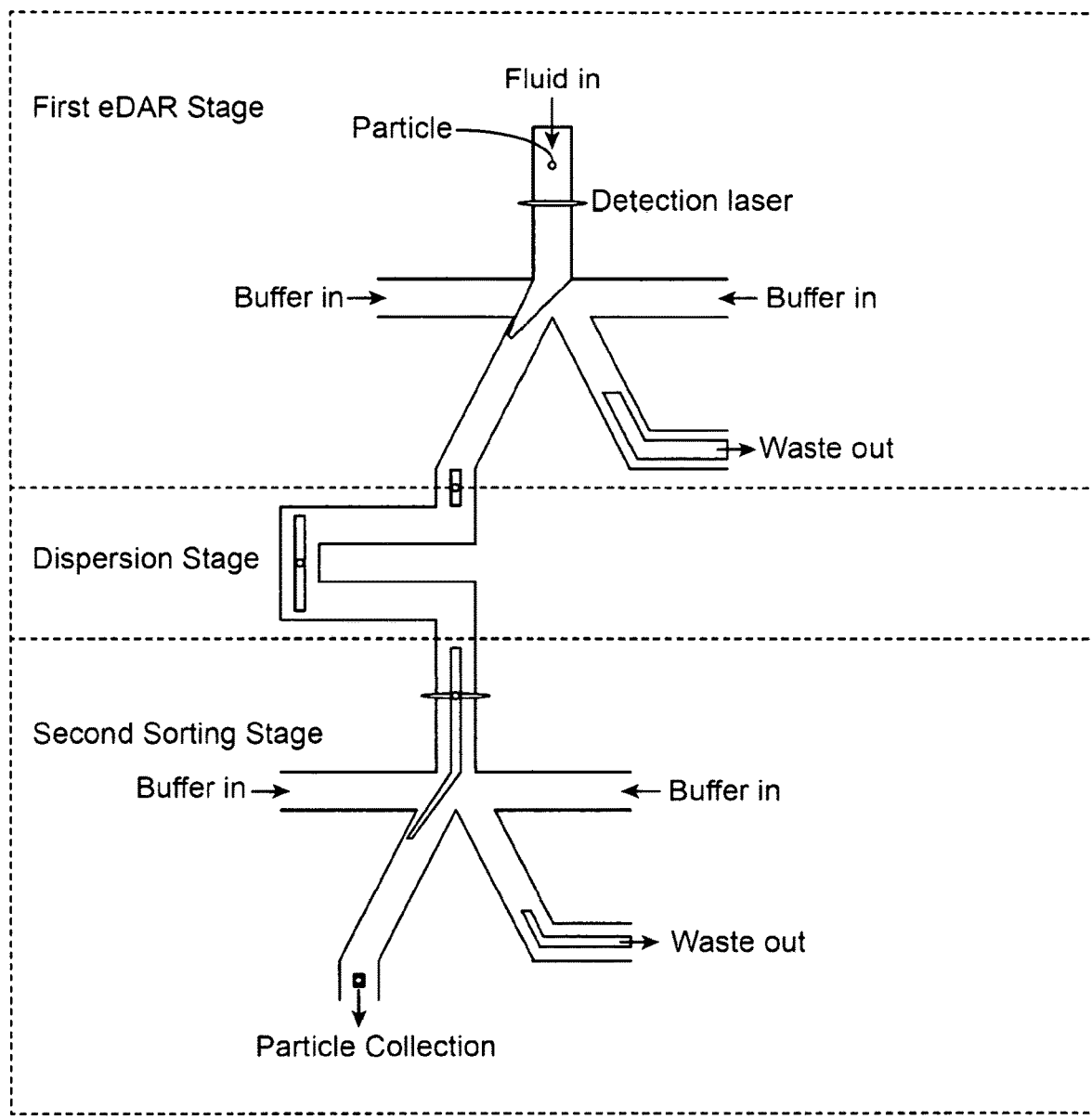
FIG. 18A shows a multi-stage sorting apparatus comprising a first eDAR stage, a dispersion stage, and a second stage of fluorescence activated sorting.

The apparatus may comprise a first eDAR stage, a dispersion stage, and a second stage of fluorescence activated sorting, as shown in FIG. 18A. The dispersion stage may be implemented between the first eDAR stage and the second-stage of fluorescence activated sorting. Although shown as a three stage apparatus in FIG. 18A, the multi-stage apparatus may further comprise a second dispersion stage and a third stage of fluorescence activated sorting. The second dispersion stage may be implemented between the second and third stages of fluorescence activated sorting. The multi-stage apparatus may further comprise a third dispersion stage and a fourth stage of fluorescence activated sorting. The third dispersion stage may be implemented between the third and fourth stages of fluorescence activated sorting. The multi-stage apparatus may further comprise a fourth dispersion stage and a fifth stage of fluorescence activated sorting. The third dispersion stage may be implemented between the fourth and fifth stages of fluorescence activated sorting. In general, the multi-stage apparatus may comprise n stages of fluorescence activated sorting and n dispersion stages after the first stage eDAR, where n is a positive integer. The n-th dispersion stage may be implemented between the n-th and n-th stages of fluorescence activated sorting and after the first stage eDAR.

In the first eDAR stage, a fluid sample enters a flow channel. The fluid sample may be a blood sample. The fluid sample may be any fluid sample as described herein. The fluid sample may comprise one or more particles to be collected. The particle may be a rare particle. The particle may be a cell. The cell may be a rare cell. The rare cell may be a cancerous cell. The cancerous cell may be a circulating tumor cell (CTC). The rare cell may be a white blood cell. The particle may be any particle to be collected as described herein. As the fluid sample flows in through a first section of the flow channel, the fluid sample passes a detection apparatus. The detection apparatus may continuously detect a series of signals from a series of aliquots of the fluid sample that pass the detection apparatus at a series of points in time. Each signal may be indicative of the presence (or absence) of the particle to be collected in a given aliquot. The detection apparatus may be any detection apparatus as described herein.

The detection apparatus may detect the presence of the particle to be collected by interrogating each group of cells of the fluid sample with a source of electromagnetic radiation. When the particle to be collected is present in a group of cells being interrogated by the detection apparatus, the detection apparatus may detect an interaction of the electromagnetic radiation with the particle in that group of cells. In particular, the detection apparatus may emit electromagnetic radiation in the form of light. The light may be ultraviolet light, visible light, or infrared light. The light may have a wavelength in a range from 100 nm to 400 nm, 400 nm to 700 nm, 700 nm to 1,000 nm, 1 µm to 10 Mm, 10 µm to 100 µm, or 100 m to 1,000 µm. The light may be emitted by one or more light emitting diodes (LEDs) or lasers. The light may be emitted by one or more gas lasers, excimer lasers, dye lasers, solid-state lasers, fiber lasers, doped fiber lasers, rare earth doped fiber lasers, semiconductor lasers, diode lasers, diode pumped lasers, vertical cavity surface emitting lasers (VCSELs), or any other lasers.

The light may interact with the particle through any optical interaction, such as optical reflection, optical transmission, elastic optical scattering, inelastic optical scattering, Rayleigh scattering, Raman scattering, surface-enhanced Raman scattering, Mie scattering, Brillouin scattering, fluorescence, autofluorescence, laser-induced fluorescence, bioluminescence, or chemiluminescence. The optical interaction between the particle and the light may be inferred by detecting the optical signal with an optical detector, such as a photodiode, photodiode array, photomultiplier, avalanche photomultiplier, camera, charge coupled device (CCD) camera, complementary metal oxide semiconductor (CMOS) camera, spectrometer, dispersive spectrometer, grating spectrometer, Fourier transform spectrometer, or microscope. The detection apparatus may utilize any optical detection technique as described herein.

The flow channel may branch into two channels. One channel (shown on the right in FIG. 18A) may constitute a waste channel. For periods of time in which the detector fails to detect the presence of the particle to be collected, the fluid sample may flow to the waste channel. The other channel (shown on the left in FIG. 18A) may flow to a dispersion stage, as described herein. Upon detecting the particle in an aliquot, the detection apparatus may send a signal to a controller (not shown) to activate a flow switching mechanism (not shown) for switching the direction of flow, so that the aliquot containing the particle to be collected flows to the dispersion stage. The flow switching mechanism may comprise a solenoid (not shown). The flow switching mechanism may switch the direction of flow back to the waste channel once the particle to be collected has moved past the junction between the flow channel and the channel leading to the dispersion stage. The movement of the particle to be collected past the junction may be detected, for instance, by placing a second detection apparatus (not shown) between the junction and the dispersion stage. In this manner, only a small aliquot of fluid containing the particle to be collected may flow toward the dispersion stage.

In the dispersion stage, the aliquot or fluid volume containing the particle to be collected may be subjected to stretching. The stretching may increase the average distance between the particle to be collected and other particles in the aliquot or fluid volume containing the particle to be collected. The stretching may be achieved by any of the stretching methods described herein. For instance, the stretching may be achieved by flow of aliquot or fluid volume through a straight channel, flow of the aliquot or fluid volume through a flow stretcher, flow of the aliquot or fluid volume through a herringbone stretcher, flow of the aliquot or fluid volume through a herringbone stretcher combined with a straight channel, flow of the aliquot or fluid volume through multiple flow paths, flow of the aliquot or fluid volume through a herringbone stretcher combined with multiple flow paths, flow of the aliquot or fluid volume through a straight channel combined with multiple flow paths, or flow or the aliquot or fluid volume through a weir stretcher, as described herein. The stretching may be imparted by parabolic flow of the aliquot or fluid volume through a microchannel, herringbone mixing, or through multiple flow paths, as described herein.

Following flow stretching in the dispersion stage, the aliquot or fluid volume containing the particle to be collected may flow to a second stage fluorescence activated sorting. The second stage fluorescence activated sorting may be configured similarly to the first eDAR stage. The second stage fluorescence activated sorting may be identical to the first eDAR stage. The second eDAR stage may be different from the first eDAR stage; for example, the second stage may sort a plurality of particles or cells in a fluid volume wherein the plurality of particles or cells are randomly distributed throughout the fluid volume (e.g., as can be the case in an aliquot) or the second stage may sort a group of cells in a fluid volume wherein the plurality of particles or cells are not randomly distributed throughout the fluid volume (e.g., as can be the case in an isolated sample or a dispersed sample). The second stage fluorescence activated sorting may utilize any separation methods as described herein with respect to the first eDAR stage. The second stage fluorescence activated sorting may concentrate the particle to be collected into a smaller volume than the aliquot produced by the first eDAR stage. In this manner, the second stage fluorescence activated sorting may further increase the purity of the aliquot or fluid volume containing the particle to be collected as compared to the aliquot produced by the first eDAR stage.

Though FIG. 18A describes an apparatus comprising a first eDAR stage followed by a second stage of fluorescence activated sorting and one dispersion stage, the principles developed may be applied to produce apparatuses utilizing two stages of fluorescence activated sorting and two dispersion stages following the first eDAR stage, three stages of fluorescence activated sorting and three dispersion stages following the first eDAR stage, four stages of fluorescence activated sorting and four dispersion stages following the first eDAR stage, or nstages of fluorescence activated sorting and n dispersion stages following the first eDAR stage, where n is a positive integer.

Figure 18B:
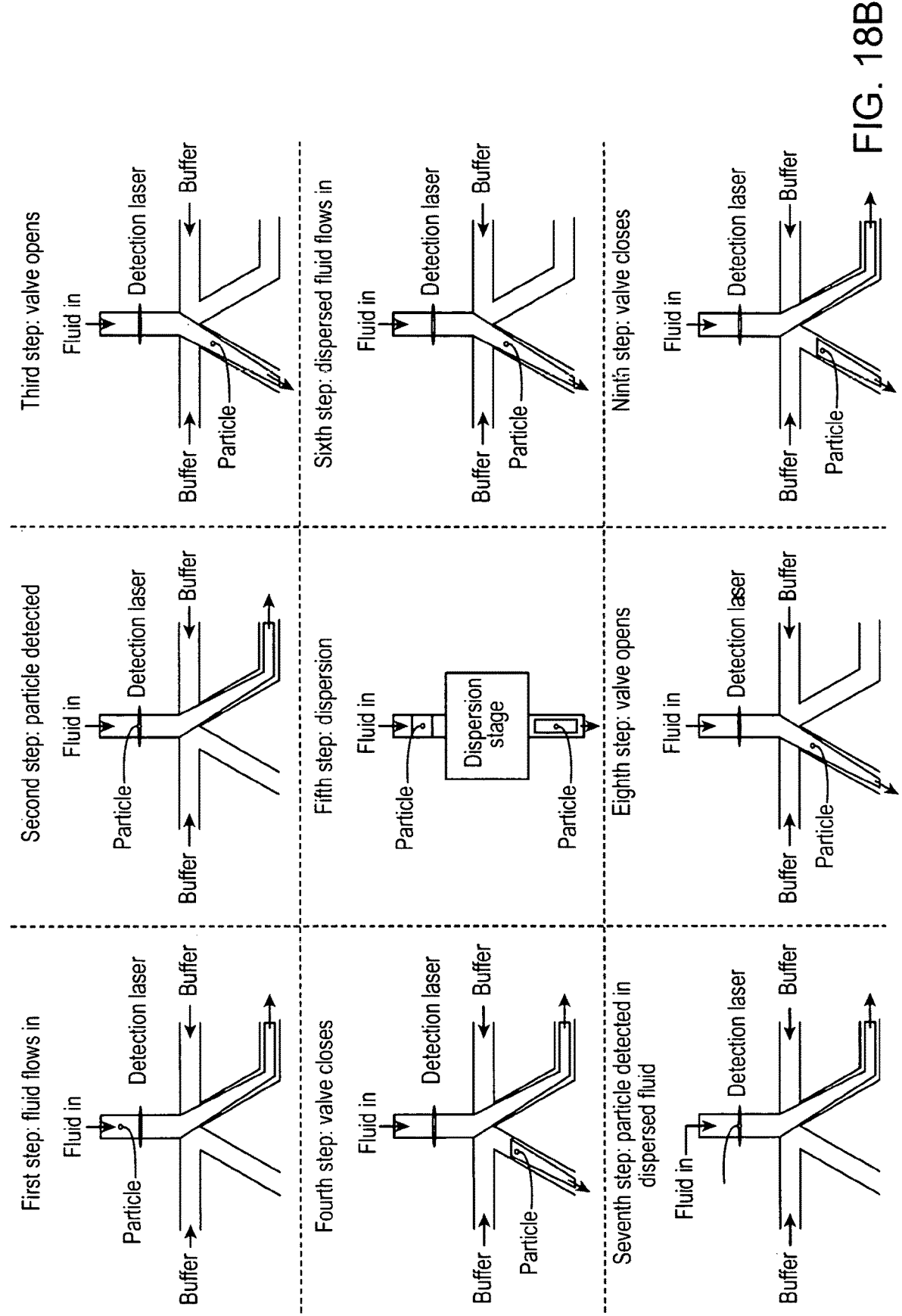
FIG. 18B shows a method of operating a multi-stage sorting apparatus.

FIG. 18B shows a method of operating an apparatus with multiple stages of fluorescence activated sorting and dispersion following a first eDAR stage, in accordance with some embodiments. In a first step, a sample flows into a junction with a first buffer stream (denoted as "L" in FIG. 18B) and a second buffer stream (denoted as "R" in FIG. 18B). The first and second buffer streams may comprise any buffer. For instance, the first and second buffer streams may comprise an aqueous buffer. The first and second buffer streams may comprise an organic buffer. The first and second buffer streams may comprise a zwitterionic buffer. The first and second buffer streams may comprise a cell growth medium. The first and second buffer streams may comprise a minimal cell growth medium. The first and second buffer streams may comprise the same buffer. The first and second buffer streams may comprise different buffers.

Prior to detection of a particle to be collected (for instance, a target cell among a population of non-target cells, such as a circulating tumor cell or white blood cell among a population of red blood cells and/or white blood cells), the flow rates of the first and second buffer streams may be selected such that the sample flows toward a waste channel. For instance, the flow rate of the first buffer stream may be chosen to be higher than the flow rate of the second buffer stream.

In a second step, a particle to be collected may be detected by a detection apparatus. The detection apparatus may be any detection apparatus as described herein. The detection apparatus may be an optical detection apparatus, as described herein.

In a third step, upon detection of the particle to be collected, a fluidic switch valve may open. The opening of the fluidic switch valve may be achieved by altering the flow rates of the first or second buffer streams. The flow rate of the first buffer stream may be decreased, so that the fluid sample flows away from the waste channel and toward the dispersion stage. The flow rate of the second buffer stream may be increased, so that the fluid sample flows away from the waste channel and toward the dispersion channel.

In a fourth step, the fluidic switch valve may be closed (such as by altering the flow rates of the first or second buffer streams to have the same flow rates as they had before the opening of the fluidic switch valve). This may cause the fluid sample to once again flow toward the waste channel. In this manner, a small aliquot or fluid volume of the fluid sample (containing the particle to be collected) may be formed and flow toward the dispersion stage. The fluidic switch valve may be closed shortly after it is opened. The fluidic switch valve may be closed in response to detection of the particle to be collected by a second detection apparatus located downstream. The fluidic switch valve may be closed after a predetermined amount of time, such as after a calculated flow time from the detection apparatus to the waste channel. The fluidic switch valve may be closed after a period of less than 1 ms, less than 2 ms, less than 5 ms, less than 10 ms, less than 20 ms, less than 50 ms, less than 100 ms, less than 200 ms, less than 500 ms, or less than 1,000 ms. The fluidic switch valve may be closed after a period that is within a range defined by any two of preceding values.

In a fifth step, the aliquot or fluid volume containing the particle to be collected may be stretched by the dispersion stage, as described herein. The stretching of the aliquot or fluid volume may result in an increase in the average spacing between the particle to be collected and the non-target particles in the aliquot or fluid volume. The aliquot or fluid volume may be stretched by any of the stretching apparatuses or methods described herein.

In a sixth, seventh, and eighth, and ninth step, the stretched aliquot or fluid volume may be further sorted by the second stage of fluorescence activated sorting. The sixth step may be similar to the first step. The seventh step may be similar to the second step. The eighth step may be similar to the third step. The ninth step may be similar to the fourth step. Following the second stage of fluorescence activated sorting, the particle to be collected may be collected in a smaller aliquot or fluid volume than the aliquot produced following the first eDAR stage. The aliquot or fluid volume may be collected downstream from the second stage of fluorescence activated sorting. For instance, the aliquot or fluid volume may be flowed to a well plate, such as a 96 well plate, for collection. The aliquot or fluid volume may be flowed to a vial for collection. The aliquot or fluid volume may be flowed to a filtration volume for collection.

The method described with respect to FIG. 18B may be extended to include a second dispersion stage and third stage of fluorescence activated sorting. The second dispersion stage may enact steps similar to the fifth step described herein. The third stage of fluorescence activated sorting may enact steps similar to the sixth, seventh, eighth, and ninth steps described herein. The method described with respect to FIG. 18B may be extended to include a third dispersion stage and fourth stage of fluorescence activated sorting. The third dispersion stage may enact steps similar to the fifth step described herein. The fourth stage of fluorescence activated sorting may enact steps similar to the sixth, seventh, eighth, and ninth steps described herein. The method described with respect to FIG. 18B may be extended to include a fourth dispersion stage and fifth stage of fluorescence activated sorting. The fourth dispersion stage may enact steps similar to the fifth step described herein. The fifth stage of fluorescence activated sorting may enact steps similar to the sixth, seventh, eighth, and ninth steps described herein. In general, the method described with respect to FIG. 18B may be extended to include an n-th dispersion stage and (n+1)-th stage of fluorescence activated sorting, where n is a positive integer. The n-th dispersion stage may enact steps similar to the fifth step described herein. The (n+1)-th stage of fluorescence activated sorting may enact steps similar to the sixth, seventh, eighth, and ninth steps described herein.

Many variations, alterations and adaptations based on the method described with respect to FIG. 18B may be possible. For example, the order of the steps of the method described with respect to FIG. 18B may be changed, some of the steps removed, some of the steps duplicated, and additional steps added as appropriate. Some of the steps can be performed in succession. Some of the steps can be performed in parallel. Some of the steps can be performed once. Some of the steps can be performed more than once. Some of the steps can comprise sub-steps. Some of the steps can be automated and some of the steps can be manual. A processor as described herein can comprise one or more instructions to perform at least a portion of one or more steps of the method described with respect to FIG. 18B.

Particle Capture and Collection

After one or more particles, such as cells (e.g., target cells), are separated and/or concentrated during two-stage sorting (and, optionally, subjection to one or more dispersion operation), the particles can be captured or collected using a filter element (e.g., as shown in FIG. 7A and FIG. 29A-FIG. 31). For example, a plurality of particles (e.g., target cells) can be purified from one or more particle or one or more type of particle using a filter element after multi-stage sorting. In some cases, the plurality of particles is concentrated to reduce the final volume of the fluid volume in which the plurality of particles are present.

Figure 29A:
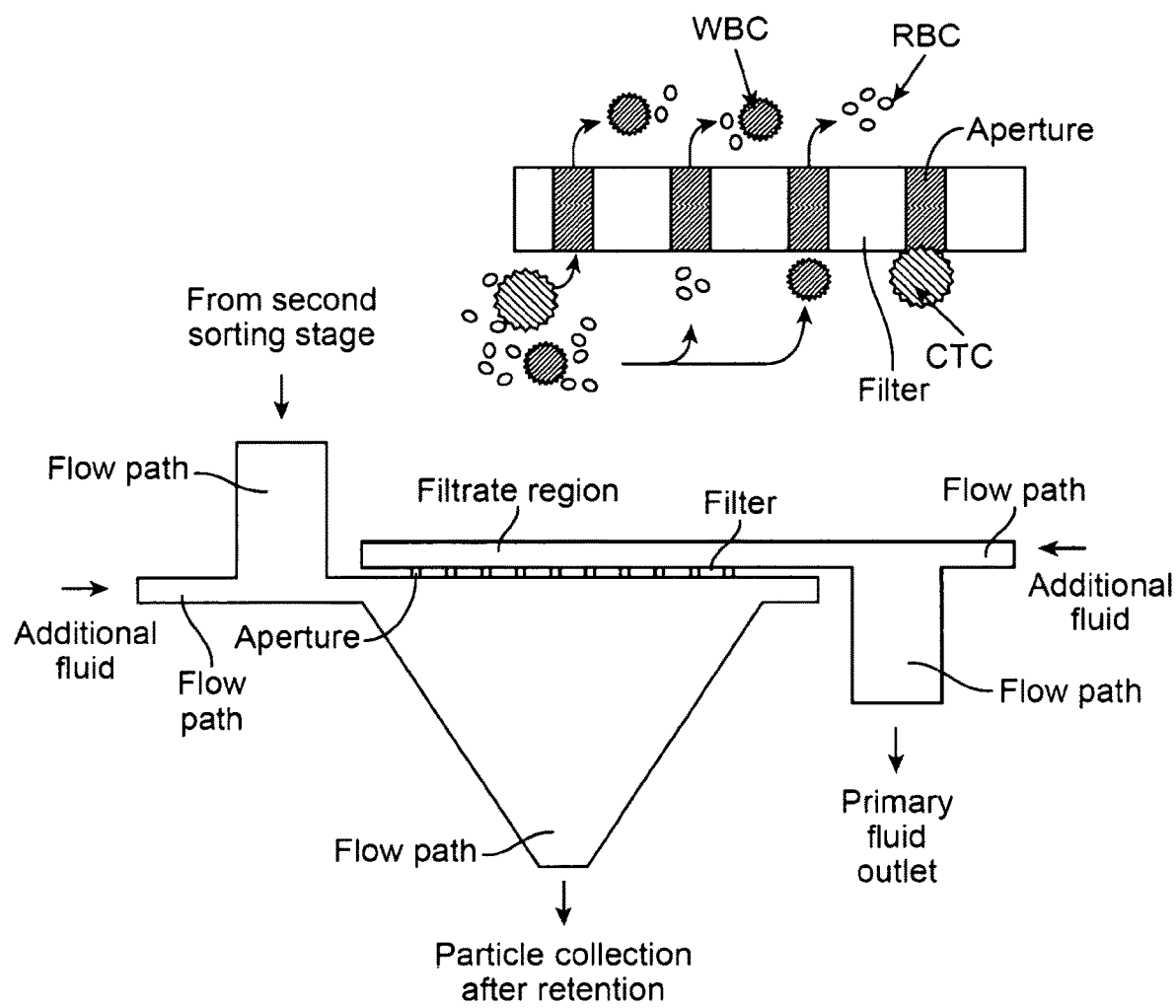
FIG. 29A shows an exemplary flow path configured for capture and release of target particles.
Figure 29B:
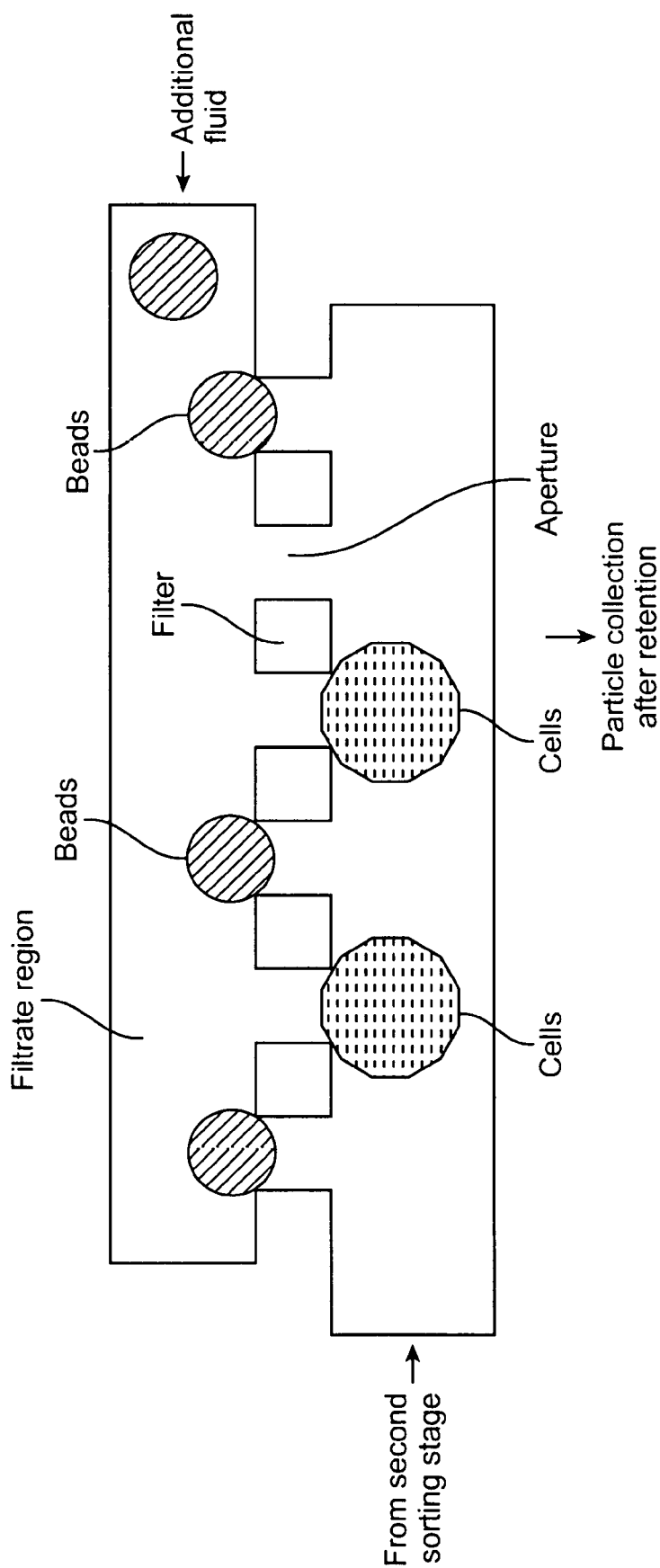
FIG. 29B shows a method of releasing cells from a filter using beads and flow reversal across the filter.

Referring now to FIGS. 29A and 29B, a fluid volume comprising one or more particle (e.g., target cell) can be introduced into a filtration area (e.g., after passing through a second sorting stage). The filtration area can be used to further separate or purify one or more target particles from one or more non-target particles present in the fluid volume.

A filtration area can comprise an input flow path in fluid communication with an output channel or flow path of a second sorting stage. A filtration area can further comprise a filter element having one or more apertures (e.g., slits, microslits, pores, micropores, or gaps). In some cases, one or more apertures (or slits, pores, or gaps) can have at least one dimension that is sized to prevent a target particle from passing through the aperture to a filtrate region located on the opposite side of the filter (e.g., the downstream side of the filter). For example, one or more apertures (or slits, pores, or gaps) can have a width, height, diameter, or cross-sectional area sized to prevent a target cell from passing through the aperture. In some cases, a dimension of an aperture is smaller than the diameter or radius of a target cell to prevent the target particle from passing through the aperture. In some cases, a dimension of an aperture is sized to allow one or more non-target particle to pass through the aperture (either while deformed or undeformed) while disallowing a target particle from passing through the aperture intact (either while deformed or undeformed). Target particles (e.g., target cells) can be captured by a filter element of a filtration area (e.g., as shown in FIGS. 29A and 29B) by applying fluid pressure (e.g., from an upstream flow path, such as the input from the second sorting stage or one or more additional upstream flow path connected to the filtration area on the upstream side of the filter element) to a fluid volume comprising the target particles such that the target particles are placed in contact with (e.g., associated with) the filter and prevented from passing through the apertures of the filter (e.g., as a result of the size and/or shape of the apertures).

A filtrate region can be connected to one or more flow paths on the opposite side of the filter as the input flow path from the sorting stage(s) upstream of the filtration area. In some cases, a flow path connected to the filtration area on the opposite side of the filter as the input flow path can comprise an output channel (e.g., a primary fluid outlet). Non-target cells can pass through such an output channel to a collection vial or to a waste receptacle after passing through the filter. For example, FIG. 29A shows white blood cells (WBC) passing through an aperture that has a width smaller than the diameter of the cell (e.g., by deformation of the WBC as a result of the fluid pressure differential across the filter element). FIG. 29 also shows red blood cells (RBC) having a diameter smaller than the width of the aperture passing through the aperture. Circulating tumor cells (CTC; e.g., target cells) are not able to pass through the aperture due to the width of the aperture relative to the diameter of the CTC and/or the CTC's deformability.

In some cases, a flow path connected to the filtration area on the opposite side of the filter as the input flow path can be a fluid input channel. For example, an additional fluid may be injected into the filtration area through a flow path downstream of the filter element of the filtration area (e.g., as shown m FIG. 29A and FIG. 29B).

In some cases, application of downstream fluid pressure to a filter element (e.g., by injecting a fluid into the filtration area via a flow path downstream of the filter element) can cause one or more particle (e.g., target particle) to be released from the filter element (e.g., to become unassociated with the filter element).

A plurality of beads may be introduced into the filtration area via an additional fluid injected through a flow path connected to the filtration area on the downstream side of the filter element. As shown in FIG. 29B, the beads (which may be rigid beads) can associate with one or more aperture of the filter element and block flow through the one or more aperture. In some cases, association of one or more bead with one or more aperture of a filter element of a filtration area can change the pressure differential across the filter element and cause one or more target particle to be released from (e.g., to become disassociated with) the filter element). In some cases, the association of one or more bead with one or more aperture of the filter element can cause an increase in retrograde fluid flow (e.g., fluid flow from the downstream side of the filter to the upstream side of the filter) through one or more aperture of the filter element, which can aid in releasing one or more target particle from the upstream side of the filter element. In some cases, the association of one or more bead with one or more aperture of the filter element can cause a decrease in the pressure differential across the filter element, which can aid in the release of one or more target particle from the upstream side of the filter element.

Figure 31:
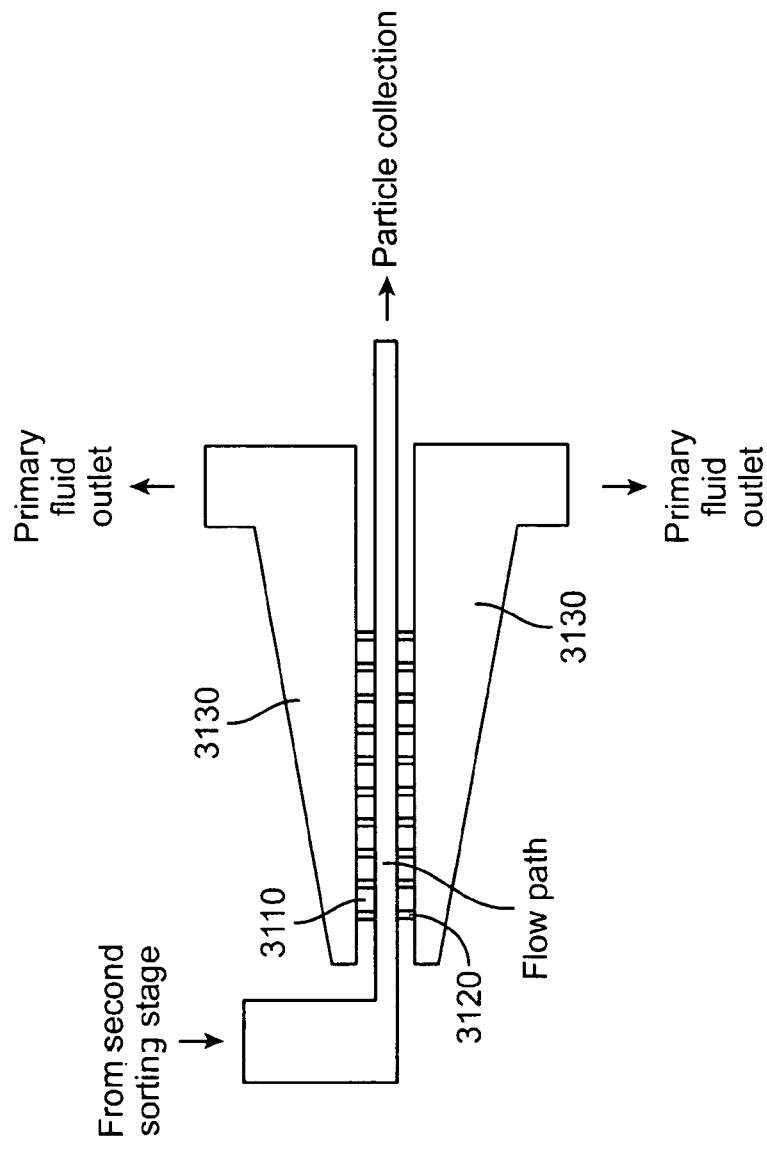
FIG. 31 shows an exemplary flow path for reducing the fluid volume in which particles are collected after separation.

After a particle or plurality of particles are released from the filter element on the upstream side of the filter element, the particle or plurality of particles can be flushed through a flow path (e.g., an outlet flow path) in fluid communication with a collection vial or collection region (e.g., as shown in FIG. 29A and FIG. 31).

In some cases, a particle can be concentrated in a fluid volume after passing through a sorting stage, after capture and release in a filtration area, and/or prior to collection. A particle can be concentrated in a fluid volume by the operation of a valve (e.g., by computer control) to allow a small volume of fluid volume comprising the particle to pass through a flow path. For example, a valve can be useful in concentrating a particle in a fluid volume by opening only for a brief period of time to allow a target particle to pass through the flow path at the location of the valve. In some cases, a valve can be open for only 2-3 milliseconds, from 2 to 20 milliseconds, or from 20 milliseconds to 50 milliseconds, and can allow 1 to 3 nanoliters, 3 to 5 nanoliters, 5 to 10 nanoliters, 10 to 20 nanoliters, or 20 to 30 nanoliters to pass through the flow path each time the valve is opened. The valve can be a solenoid valve, which can be useful in concentrating a particle because it can be opened and closed in a very short, reproducible period of time (e.g., 2-3 milliseconds, from 2 to 20 milliseconds, or from 20 milliseconds to 50 milliseconds).

The opening and/or closing of a valve can be controlled by a computer. For example, a valve used to concentrate a particle in a fluid volume can be opened when a detector connected to the computer detects a target particle. By opening a valve only when a target particle is detected, a minimum amount of fluid can be allowed through the flow path along with each target particle that is allowed to pass through the flow path.

Figures 30A, 30B:
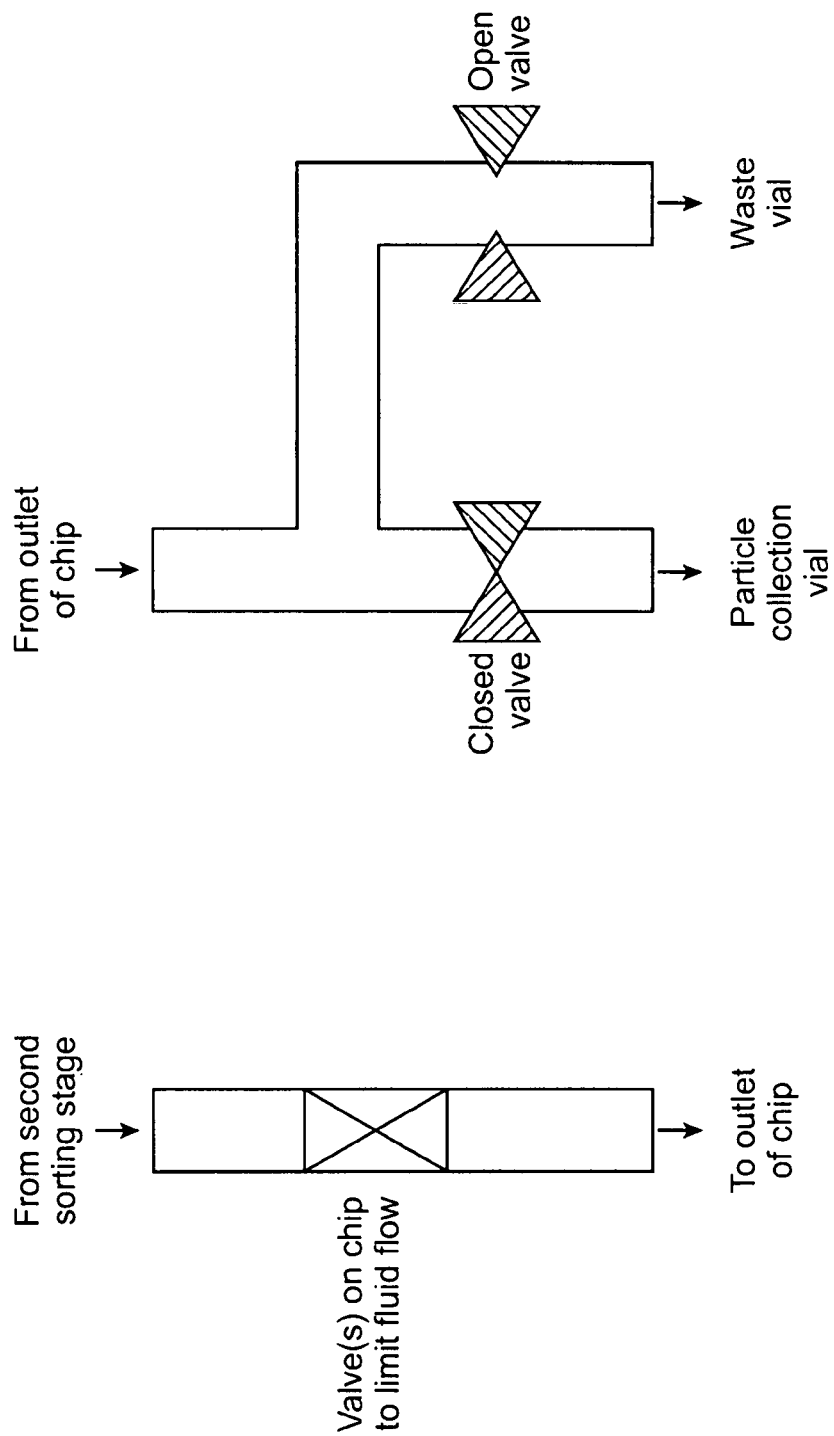
FIG. 30A shows a top view of an exemplary flow path with a valve to limit flow through the flow path.
FIG. 30B shows an exemplary flow path comprising valves for reduction of the fluid volume in which particles are collected.
Figure 30C:
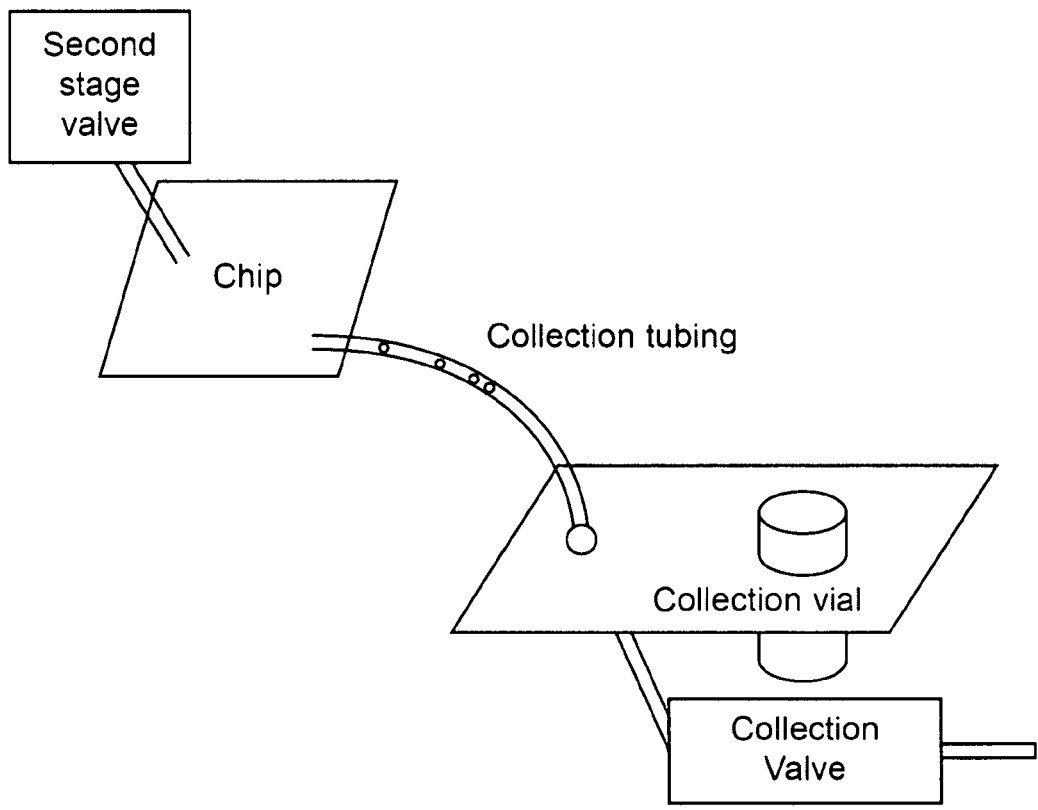
FIG. 30C shows an apparatus for collecting concentrated particles after multi-stage sorting.

As shown in FIGS. 30A-30C, the valve can be an in-line valve, a two-way pinch valve, or an external valve. An in-line valve or a two-way pinch valve can be integrated into a microfluidic chip. An external valve can be connected to a microfluidic chip (e.g., by fasteners). In some cases, an external valve can be removable from a microfluidic chip. An external valve can operate by pinching off a flow path (e.g., a length of tubing) when closed.

As shown in FIG. 30C, a flow path comprising a valve (e.g., a collection valve) can be in fluid communication with an outlet of a second sorting stage, a microfluidic chip (e.g., a microfluidic sorting chip), and/or a length of collection tubing. In some cases, the collection valve can be disconnected from the flow path and the flow path (e.g., tubing previously connected to the collection valve) can be placed in fluid communication with a collection vial when particles that have been sorted are present in the flow path between the second sorting stage and the collection valve (e.g., in one or more flow path of the microfluidic chip or in tubing between the second sorting stage and the collection valve). The sorted particles in the flow path can be flushed into the collection vial after the flow path is connected to the collection vial.

Referring now to FIG. 31, a filtration area can comprise structures useful for passive reduction of the volume of the fluid volume comprising one or more target particles. A filtration area can comprise an input flow path or channel in fluid communication with an outlet from a second sorting stage and in fluid communication with a particle collection region or structure, such as a collection vial. The flow path connecting the outlet of the second sorting stage with the particle collection region can comprise one or more filter element 3110 having a plurality of apertures 3120 (or slits, microslits, pores, micropores, or gaps) with a dimension (e.g., a width, height, diameter, or cross-section) sized so that one or more target particle is disallowed from passing through the aperture intact while fluid and, optionally, one or more non-target particle are able to pass through the aperture. The filtration area may comprise one or more filtrate region 3130 located on the opposite side of filter element 3110 as the flow path connecting the second sorting stage to the particle collection region or structure. The filtrate region(s) can be in fluid communication with one or more fluid outlet (e.g., a flow path in fluid communication with an outlet or waste).

Through the application of fluid pressure to the upstream end of the flow path (e.g., application of fluid pressure at or upstream of the input flow path or channel of the filtration area), one or more particle in a fluid volume introduced into the filtration area from the second sorting stage can be placed into contact with (e.g., associated with) filter element 3110. This fluid pressure can cause a portion of the fluid volume comprising the one or more particle to pass through the apertures of filter element 3110 into filtrate region 3130. In some cases, this movement of a portion of the fluid volume across filter element 3110 can cause the fluid volume comprising the one or more particles to decrease in size. In some cases, the movement of a portion of the fluid volume across filter element 3110 can cause one or more particles (e.g., one or more non-target particles) to pass through one or more apertures 3120 of filter element 3110 to filtrate 3130. In some cases, capillary forces and/or the volume differential between filtrate region 3130 and the flow path connecting the second sorting stage with the collection region can be sufficient to cause a portion of the fluid volume and/or one or more particles (e.g., non-target particles) to move across filter element 3110 to filtrate region 3130 (e.g., through one or more aperture 3120 of filter element 3110).

Markers/Biomarkers

The method provides for a plurality of biomarkers that can be expressed by, located on or near an analyte (e.g., trapped particle). The plurality of biomarkers that can be detected by the instant disclosure is subject to the number of rounds of immunostaining and photobleaching that can be performed on the trapped particle. Each round of immunostaining can include no tags, 1 tag, 2 tags, 3 tags, 4 tags, 5 tags, 6 tags, 7 tags, 8 tags, 9 tags or 10 tags. The range of tags for each round of immunostaining can include 1-10 tags (e.g., 4).

In some aspects, the presence of a marker, such as a biomarker, is indicated by a signal emitted by a tag, wherein the tag has an affinity for the marker. As used herein, the phrase "has an affinity for" broadly encompasses both direct molecular binding affinity for a marker by a tag, as well as indirect affinity, such as an ability of the tag and the marker to interact via a molecular complex involving one or more other structures. For example, in some aspects, the tag may be a primary antibody with a direct affinity for the marker, whereas in other aspects, the tag may be a secondary antibody with an indirect affinity for the marker.

In some aspects, cells are isolated according a specific marker or biomarker profile, such that a given cell exhibits a unique and/or identifiable marker or biomarker profile. In certain aspects, the marker or biomarker profile is a specific combination of one or more, two or more, three or more, four or more, five or more, six or more, seven or more, eight or more, nine or more, or ten or more markers or biomarkers, which can be used to define and identify a cell or cell type. In some aspects, the marker or biomarker profile can be used to identify a cell as being part of a particular population of cells have a particular set of properties.

In some aspects, biomarkers are extracellular. In other cases, biomarkers can be intracellular, cytoplasmic, intra-cytoplasmic, cell surface, extranuclear, intranuclear, lysosomal, mitochondrial, endoplasmic reticular and the like. In other cases, biomarkers can be attached to but not in trans to the particle.

In some aspects, biomarkers can be an amino acid, a peptide, a polypeptide, a protein, a denatured protein. In these cases, structures can be native or denatured.

In some aspects, biomarkers can be a nucleic acid, an oligonucleic acid, a ribonucleic acid, a transfer ribonucleic acid, a messenger ribonucleic acid, a micro ribonucleic acid or a deoxyribonucleic acid. In these cases, acids can be single or double stranded.

In other cases, the rare particle can be a cell, protein, protein complex, nucleic acid, nucleoprotein complex, carbohydrate, metabolite, catabolite, and the like. In some aspects, the rare particle is a cell. In some aspects, the cell can be a cancer cell, a circulating tumor cell (CTC), a cancer stem cell, a cancer cell displaying a cancer surface antigen, for example, one selected from the groups consisting of CD44, CD2, CD3, CD10, CD14, CD16, CD24. CD31, CD45, CD64, CD140b, or a combination thereof.

In some aspects the cell is a fetal cell. In some aspects, the fetal cell can be in maternal fluid. The maternal fluid can include whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolympth, peritoneal fluid, pleural fluid, cerumen, epicardial fluid, and secretions of the respiratory, intestinal and genitourinary tracts.

In some aspects, the analyte is a dissociated cell that is not connected to other cells or extracellular matrix, or embedded within a tissue.

In some aspects, cancer stem cells can be distinguished from ordinary cancer cells by perfusing other reagents that selectively bind to biomarkers, which can include but are not limited to CD44, CD2, CD3, CD10, CD14, CD16, CD24, CD31, CD45, CD64, CD140b or CD166.

For example, tags can be designed to detect expression of EGFR and CD166 to demonstrate the mesenchymal characteristics of tumor cells. Other related markers, such as vimentin and cadherin, can be used in this group.

In other cases, biomarkers that indicate the viability of the particle can be used. In these cases, biomarkers which indicate apoptosis, necrosis, mitosis, stage of mitosis, meiosis and the like can be used.

In some aspects, each set of markers can include a nuclear stain (Hoechst) as a positive control biomarker, CD45 conjugated with FITC as a negative control biomarker, and two protein biomarkers conjugated with PE or Alexa 647. In some aspects, the Hoechst stain may not be photobleached. In this case, Hoechst is a positive control. In this case, Hoechst may not be photobleached with a standard light source. In this case, a UV exposure may be used to bleach the stain.

Samples

In the disclosure provided herein, samples can include fluid samples. Fluid samples can originate from a variety of sources. In some aspects, the sources may be humans, mammals, animals, microbes, bacteria, fungus, yeast, viruses, rodents, insects, amphibians and fish.

Fluid samples provided in this disclosure can be liquids that may or may not contain a rare particle of interest. In some aspects, the sample may be an environmental fluid sample, for example from a lake, river, ocean, pond, stream, spring, marsh, reservoir, or the like. In yet other cases, the sample may be a water sample, for example from a desalinization plant, water treatment plant, reservoir, spring, stream, glacial water flow, water tower, or other water source that may be contemplated as a source of potable water.

In some aspects, this disclosure provides analytes, including analytes that are rare particles. A rare particle can be a cell or macromolecule present in a fluid sample at a low level. In certain aspects, a rare particle can be a cell, protein, protein complex, nucleic acid, nucleoprotein complex, carbohydrate, metabolite, catabolite, and the like. In certain aspects, a particle can be considered rare if it is present in a fluid sample at a concentration of less than about 10% of the total particle population in the fluid, or at less than about 9%, 8%, 7%, 6%, 5%, 4%, 3%, 2%, 1%, 0.5%, 0.1%, 0.05%, 0.01%, or less of the total particle population in the fluid. In yet other cases, the rare particle can be present in a fluid sample at less than about 1 part per $10^3$ of the total particle population in the fluid, or at less than about 1 part per $10^4$, $10^5$, $10^6$, $10^7$, $10^8$, $10^9$, $10^{10}$, $10^{11}$, $10^{12}$, or less of the total particle population in the fluid. In certain aspects, a particle can be considered rare if it is present in a fluid sample at a concentration of less than 10% of the total particle population in the fluid, or at less than 9%, 8%, 7%, 6%, 5%, 4%, 3%, 2%, 1%, 0.5%, 0.1%, 0.05%, 0.01%, or less of the total particle population in the fluid. In yet other cases, the rare particle can be present in a fluid sample at less than 1 part per $10^3$ of the total particle population in the fluid, or at less than 1 part per $10^4$, $10^5$, $10^6$, $10^7$, $10^8$, $10^9$, $10^{10}$, $10^{11}$, $10^{12}$, or less of the total particle population in the fluid.

In some aspects, a fluid sample can contain a certain percentage of water and/or other elements. For example, a fluid sample can be blood which contains, amongst other materials, plasma. Generally, plasma is mostly water and can contain proteins, ions, vitamins, enzymes, hormones, and other chemicals in the body.

In some aspects, the fluid samples can be body fluids. Body fluids are often complex suspensions of biological particles in a liquid. For example, a body fluid can be blood. In some aspects, blood can include plasma and/or cells (e.g., red blood cells, white blood cells, circulating rare cells) and platelets. In some aspects, 55% of blood fluid volume can be cells. In some aspects, a blood sample can be concentrated so that at least 30%, at least 40%, at least 50%, at least 60%, at least 70%, at least 80%, or at least 90% of the blood is cells. In some aspects, a blood sample contains blood that has been depleted of one or more cell types. In some aspects, a blood sample contains blood that has been enriched for one or more cell types. In some aspects, a blood sample can be diluted so that at least 30%, at least 40%, at least 50%, at least 60%, at least 70%, at least 80%, or at least 90% of the blood is cells. In some aspects, a blood sample contains a heterogeneous, homogenous or near-homogenous mix of cells.

Body fluids can include, but are not limited to, whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolymph, peritoneal fluid, pleural fluid, cerumen, epicardial fluid, and secretions of the respiratory, intestinal and genitourinary tracts. In some aspects, body fluids can be in contact with various organs (e.g., lung) that contain mixtures of cells and bioparticles.

In some aspects, body fluids can contain rare particles. In some aspects, the rare particle is a rare cell. Rare cells can be nucleated or non-nucleated. Rare cells include, but are not limited to, cells expressing a malignant phenotype; fetal cells, such as fetal cells in maternal peripheral blood, tumor cells, such as tumor cells which have been shed from tumor into blood or other bodily fluids; cells infected with a virus, such as cells infected by HIV, cells transfected with a gene of interest; and aberrant subtypes of T-cells or B-cells present in the peripheral blood of subjects afflicted with autoreactive disorders.

In some aspects, the body fluid can be blood and contain rare cells. The rare cells can be erythrocytes, white blood cells, leukocytes, lymphocytes, B cells, T cells, mast cells, monocytes, macrophages, neutrophils, eosinophils, dendritic cells, stem cells, erythroid cells, cancer cells, tumor cells or cell isolated from any tissue originating from the endoderm, mesoderm, ectoderm or neural crest tissues. Rare cells can be from a primary source or from a secondary source (e.g, a cell line).

The type and amount of cells and bioparticles that are present in a particular body fluid (e.g., blood) can reveal information about the health of the organism. For example, a subject suffering from cancer can have cancerous cells in body fluid. A sample from a subject suffering from an infection can contain an increased number of immune cells (e.g., lymphocytes, neutrophils, B cells, T cells, dendritic cells, etc.) indicative of infection or can contain pathogenic material such as microbial cells or nucleic acids. A sample from a pregnant female can contain fetal cells indicative of the genotype or karyotype of the fetus.

Some cells or bioparticles can be present in a body fluid in rare quantities compared to normal quantities. Such rare cells can include, circulating tumor cells, cancer stem cells, etc. These cells can appear in a body fluid as a result of an event (e.g., cancer) occurring in a region of the body. The cell can originate from the organ containing the body fluid or an organ near the body fluid. For example, the rare breast cancer cell can be present in blood or lymph fluid located near a mammary gland. In some aspects, the cell originates from a more distant organ. For example, a cell that originates from a testicular tumor can be present in a blood sample taken from the arm.

Analysis

The disclosure further provides for methods whereby an analysis can be performed. In some aspects, the analysis can include a source for interrogating an aliquot or a fluid volume. In other cases, wherein an aliquot contains an analyte (e.g., rare particle) that can intrinsically exhibit chemiluminescence or bioluminescence, the apparatus may not require a source for interrogating the aliquot.

In some aspects, a ranking device can be selected from a computer, a processor, a controller, a chip with integrated circuits, a circuit board, an electronic element, software, an algorithm, or a combination thereof. In some aspects, the processor can be a digital processor (e.g., FGPA, ASIC, or RT). In some aspects, a computer accepts the signal from the detection device and through an algorithm ranks the aliquot. The ranking device can direct the aliquot into the appropriate channel based on the value of the ranking (e.g., the presence, absence, quantity, identity, or composition of rare particles in the fluid sample).

In some aspects, the information coming from the first detector can be analyzed. The information from the first detector can be analyzed and the result can show that the analyte is positive. In some aspects, the information from the detector can be analyzed and the result can show that the analyte is negative. In some aspects, the ranking device sends the signal, which reads to the positive or the negative analyte, to the hydrodynamic switching element (e.g., solenoid valve) to sort the analytes. In some aspects the positive analyte can be moved to a unique channel of the microfluidic chip. In some aspects, the positive analyte can be moved to a unique chamber of the microfluidic chip. In some aspects, the positive analyte can be moved to the waste chamber of the microfluidic chip. In some aspects the negative analyte can be moved to a unique channel of the microfluidic chip. In some aspects, the negative analyte can be moved to a unique chamber of the microfluidic chip. In some aspects, the negative analyte can be moved to the waste chamber of the microfluidic chip. In some aspects, the positive analyte is partitioned from the negative analyte.

In some aspects, analysis can be performed using the information relayed from a second detector. The second detector can be used to confirm the information obtained using the first detector. In some aspects, the second detector can be located on the microfluidic chip. In some aspects, the second detector may not be located on the microfluidic chip. In some aspects, the second detector obtains a signal from the cells that can be sorted based on the signal detected by the first detector. In some aspects, the second detector receives detects signal from the sorted cells and can send information about the signal to a computer. The computer can be used to determine whether the appropriate cell was sorted.

Applications

The disclosure provides for the method to be used in a variety of applications. In some aspects, the method can provide a subject a diagnosis or prognosis for a condition associated with the presence of a rare particle in a fluid sample, for example a biological fluid such as a blood sample.

The methods and apparatuses described herein can comprise the steps of: (a) contacting a biological fluid from the subject with a tag under conditions suitable to transform the tag into a complex comprising said tag and an analyte; (b) detecting the presence or absence of a complex formed in step (a) in an aliquot of the biological fluid; (c) assigning a value to the aliquot based on the presence or absence of a complex formed in step (a); and (d) providing a diagnosis or prognosis to the subject based on analysis of the isolated aliquot. In some aspects, step (b) can comprise interrogating the aliquot with a source of radiation and detecting a signal emitted by the tag bound to the analyte.

In various aspects, methods are provided for identifying a plurality of markers present on an analyte within a fluid, wherein the method comprises: (a) detecting a signal from a first tag using a source of radiation, wherein the first tag is attached to a first structure that binds to a first marker on the analyte; (b) partitioning the analyte based on the presence of the first tag; (c) reducing the intensity of the signal of the first tag; (d) contacting the analyte with a second structure that binds to a second marker, wherein the second structure is attached to a second tag; and (e) detecting the second tag.

In some aspects, the partitioning of step (b) is based on the presence of the first tag and a third tag. In further aspects, the partitioning of step (b) is performed with a microfluidic device. In still further aspects, the partitioning of step (b) and the detecting in at least one of step (b) or step (e) occurs within the same microfluidic device.

In various aspects, methods are provided for detecting a plurality of markers present on an analyte, the method comprising: contacting the analyte with a first tag, wherein the analyte comprises a first marker and the first tag has an affinity for the first marker; detecting a first signal emitted by the first tag, wherein the presence of the first signal indicates the presence of the first marker; partitioning a fluid comprising the analyte based on the presence of the first signal; reducing the intensity of the first signal; contacting the analyte with a second tag, wherein the analyte comprises a second marker and the second tag has an affinity for the second marker; and detecting a second signal emitted by the second tag, wherein the presence of the second signal indicates the presence of the second marker.

In some aspects, the signal of the first tag is reduced by greater than 50%. In certain aspects, reducing the intensity of the signal is accomplished by applying radiation to the analyte. In further aspects, white light is used to reduce the intensity of the signal. In still further aspects, a laser is used to reduce the intensity of the signal. In other aspects, a light emitting diode is used to reduce the intensity of the signal. In some aspects, reducing the intensity of the signal is accomplished by applying a chemical to the first tag. In certain aspects, the chemical is a reducing agent. In further aspects, the reducing agent is dithiothreitol.

In some aspects, partitioning the fluid is based on the presence of the first signal and a third signal. In further aspects, detecting the first signal, detecting the second signal, partitioning the fluid, or a combination thereof is performed using a microfluidic device.

In some aspects, the analyte is a cell. In certain aspects, the cell is a cancerous cell. In further aspects, the cancerous cell is a rare cell. In some aspects, the analyte is a circulating tumor cell. In certain aspects, the cell is a bacterial cell, an immune cell, a fetal cell, a cell indicative of a disease remaining after treatment, or a stem cell. In further aspects, the cell is a rare cell, comprising less than 1% of the total cell population in the fluid. In certain aspects, the analyte is a dissociated cell.

In some aspects, the fluid is selected from the group consisting of: whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolympth, peritoneal fluid, pleural fluid, cerumen, epicardial fluid, and secretions of the respiratory, intestinal and genitourinary tracts. In certain aspects, the fluid is whole blood. In other aspects, the fluid is fractionated whole blood.

In some aspects, the first tag is a fluorophore. In further aspects, the first tag is an antibody. In other aspects, the first tag is a probe comprised of a nucleic acid. In certain aspects, the methods further comprise imaging the signal from the first tag and the second tag. In some aspects, the analyte is present in a fluid, and the fluid is an aliquot of a larger volume of fluid. In further aspects, detecting the first signal emitted by the first tag is performed simultaneously on a plurality of analytes.

In certain aspects, the partitioning is performed semi-automatically or automatically. In certain aspects, the partitioning is performed by ensemble-decision aliquot ranking. In some aspects, a flow cytometer is not used to partition the analyte.

In further aspects, the analyte comprises a plurality of markers. In some aspects, each of the plurality of markers is a biomarker. In certain aspects, the analyte comprises an expression profile, wherein the expression profile is defined by the plurality of markers.

In further aspects, the method further comprises contacting the analyte with a buffer. In still further some aspects, the buffer contains a fixative. In certain aspects, the buffer contains a permeabilization agent. In other aspects, the buffer is a washing buffer.

In various aspects, methods are provided for isolating cells from a sample comprising a first cell type and a second cell type, the methods comprising: (a) introducing the sample into a microfluidic chip via a set of tubing wherein the microfluidic chip comprises (i) at least one channel fluidly connected to the set of tubing; (ii) a detector configured to detect signals of cells within the at least one channel; and (iii) at least one chamber fluidly connected to the at least one channel; (b) flowing a portion of the sample past the detector; (c) using the detector to detect the presence or absence of the first cell type within the portion of the sample; (d) if the first cell type is detected within the portion of the sample, directing an aliquot of the sample into the chamber, wherein the aliquot comprises the first cell type; and (e) repeating steps (b), (c), and (d), thereby isolating multiple aliquots in the chamber such that the chamber comprises greater than 80% of a total number of first cell types within the sample and less than 5% of a total number of second cell types within the sample.

In various aspects, methods are provided for isolating cells from a sample, the methods comprising: (a) introducing the sample into a microfluidic chip, wherein the sample comprises a first cell type and a second cell type, and wherein the microfluidic chip comprises: a channel; a detector configured to detect a signal emitted within the channel; a chamber in fluidic communication with the channel; (b) flowing a portion of the sample through the channel, wherein the portion comprises a plurality of the first cell type, a plurality of the second cell type, or a combination thereof; (c) detecting the presence or absence of the first cell type within the portion using the detector; (d) directing the portion into the chamber if the first cell type is present within the portion; and (e) repeating (b), (c), and (d) a sufficient number of times such that the chamber comprises more than 80% of the total number of the first cell type present within the sample and less than 5% of the total number of the second cell type present within the sample.

In some aspects, at least one of the first cell type and the second cell type is a cancerous cell. In certain aspects, the cancerous cell is a rare cell. In further aspects, at least one of the first cell type and the second cell type is a circulating tumor cell. In still further aspects, at least one of the first cell type and the second cell type is a bacterial cell, an immune cell, a fetal cell, a cell indicative of a disease remaining after treatment, or a stem cell. In some aspects, at least one of the first cell type and the second cell type is a rare cell, comprising less than 1% of the total cell population in the sample.

In some aspects, the sample is selected from the group consisting of: whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolympth, peritoneal fluid, pleural fluid, cerumen, epicardial fluid, and secretions of the respiratory, intestinal and genitourinary tracts. In certain aspects, the sample is whole blood. In other aspects, the sample is fractionated whole blood.

In some aspects, the chamber is external to the microfluidic chip. In certain aspects, the chamber is a vial, a microcentrifuge tube, or a well in a well plate. In further aspects, the chamber is in fluidic communication with the channel via tubing. In still further aspects, the chamber is in fluidic communication with the channel via a capillary tube.

In various aspects, methods are provided for isolating an aliquot or fluid volume of a fluid sample within a microfluidic chip, wherein the aliquot or fluid volume comprises a rare particle, the methods comprising the steps of: (a) detecting the presence or absence of the rare particle in the aliquot; (b) assigning a value to the aliquot based on the presence or absence of the rare particle; and (c) directing the flow of the aliquot based on the assigned value by opening an electro-actuated valve, wherein the electro-actuated valve is located on a device that is external to the microfluidic chip. In some aspects, the microfluidic chip comprises a sample input channel, at least two output channels, and at least one directional flow channel, and wherein the electro-actuated valve controls the flow of fluid within the directional flow channel.

In various aspects, the steps of introducing a tag, sample (e.g., a sample comprising a particle, such as an analyte, which can be, for example, a cell or molecule) or portion of a sample into a channel, microfluidic chip, or sorting device, causing the tag, sample, or portion of a sample to flow through a channel or flow path, causing the sample or portion thereof to reverse its direction of flow, interrogating a tag, sample, or portion of a sample (e.g., by operating a source of radiation), modulating the flow of a sample or portion thereof in a flow path or channel, modulating a flow profile within a flow path or channel can be controlled or performed by a processor of a computer. In various aspects, the steps of operating one or more detector, detecting the presence or absence of a rare particle, assigning a value to an aliquot (e.g., a portion of a sample, which can comprise an analyte such as a cell or molecule) based on the presence or absence of a rare particle, causing the aliquot or sample to be partitioned, subjecting the aliquot to a separation procedure (e.g., such as directing the flow of the aliquot based on the assigned value by opening an electro-actuated valve), performing a separation procedure, operating a valve, capturing a particle such as an analyte (e.g., a cell or molecule), releasing a particle such as an analyte, filtering a sample or portion thereof, or collecting a sample or portion thereof can be controlled by a processor of a computer.

Diagnosis of Disease

In some aspects, analytes (e.g., cells) isolated using the present method can be further subjected to subpopulation analysis (e.g., according to genotype or phenotype) to develop a targeted treatment. For example, the isolated cells (e.g., tumor cells) can be incubated with tags (e.g., fluorescent antibodies) binding to specific biomarkers (e.g., drug targets) to determine the presence or degree of expression of a drug target. Once the expression of the drug target is confirmed, drugs can be chosen for therapy that are specifically developed to target the expression of a particular drug target. In one example, the isolated tumor cells can be incubated with fluorescent antibodies binding specifically to Her2 receptor to determine whether the breast tumor shedding CTCs is Her2-positive. If the isolated tumor cells exhibit high Her2 expression, Herceptin (trastuzumab) can be used as a therapy as this drug is designed to target and block the function of HER2 protein overexpression. Other known drug targets, including BCR-ABL or PDGFR (targeted by drug Gleevec), ERBB2 (targeted by Herceptin), EFGR (targeted by Iressa, Tarceva), RAR-alpha (targeted by ATRA), Oestrogen receptor (targeted by Tamoxifen), aromatase (targeted by Letrazole), androgen receptor (targeted by Flutamide, Biclutamide), CD20 (targeted by Rituximab), VEGF-receptor (targeted by Avastin) can also be similarly screened from the isolated tumor cells before prescribing the appropriate chemotherapy regimen.

In some aspects, the analyte can be a rare particle (e.g., a cancer cell or circulating tumor cell (CTC)). In other cases, the rare particle can be a parasitic cell or organism, for example, a species of *Giardia* or *Cryptosporidium*, a erythrocyte infected with a species of *Plasmodium*, a lymphocyte or leucocyte infected with HIV, a fetal cell in maternal blood, a stem cell, a prion-infected cell, a CD4+ T-cell, and the like.

In some aspects, the method can comprise detecting a circulating tumor cell in a blood sample from a subject. The method can include eDAR. In certain aspects, the subject can be a patient who has been diagnosed with cancer. In some aspects, the cancer can be Stage I, Stage II, Stage III, or Stage IV. In some aspects, circulating tumor cells (CTCs) can be detected in a blood sample from a patient previously diagnosed with cancer. In these cases, the patient can be further diagnosed with metastatic cancer.

In some aspects, the method can be used for diagnosing metastatic cancer in a subject that has previously been diagnosed with a solid tumor, the method comprising the steps of: (a) detecting the presence or absence of a CTC in an aliquot of a blood sample from the subject; (b) assigning a value to the aliquot based on the presence or absence of the CTC; and (c) directing the flow or collection of the aliquot based on the assigned value.

In some aspects, the absence of CTCs in the blood sample can be correlated with the subject not having metastatic cancer. The presence of at least one CTC in the blood sample can be correlated with the subject having metastatic cancer. In some aspects, the presence of at least a number of CTCs in the blood can be correlated with the subject having metastatic cancer. The method can further comprise a step of (d) diagnosing the subject as not having metastatic cancer if no CTCs are detected in the blood sample or diagnosing the subject as having metastatic cancer if at least one CTC is detected in the blood sample.

The disclosure also provides for a method for monitoring a subject diagnosed with cancer. The method can comprise detecting the presence or absence of a CTC in an aliquot of a blood sample from the subject using the eDAR method provided herein. In some aspects, the patient can be monitored for the progression of cancer to metastatic cancer at regular intervals, for example, at least once a year, at least twice a year, at least 3, 4, 5, 6, 7, 8, 9, 10, or more times a year, or at least about 3, 4, 5, 6, 7, 8, 9, 10, or more times a year. In some aspects, the subject can be monitored once a month, or at least 2, 3, 4, 5, 6, 7, 8, 9, 10, or more times a month. In some aspects, the subject can be monitored about once a month, or at least about 2, 3, 4, 5, 6, 7, 8, 9, 10, or more times a month. The absence of CTCs in the blood sample can be correlated with the subject not having metastatic cancer. The presence of at least one CTC in the blood sample can be correlated with the subject having metastatic cancer. The presence of at least a number of CTCs in the blood can be correlated with the subject having metastatic cancer.

In cases wherein a CTC is detected in a blood sample, the method can further comprise a step of subjecting one or more aliquots identified as containing a CTC to further analysis to identify one or more characteristics of the CTC cell or cells. For example, an aliquot or pool of aliquots containing a CTC can be contacted with one or more detection reagents specific for one or more cancer-specific surface antigens. Non-limiting examples of cancer-specific surface antigens that can be assayed for include, without limitation, BCR-ABL or PDGFR (targeted by drug Gleevec), ERBB2 (targeted by Herceptin), EFGR (targeted by Iressa, Tarceva), RAR-alpha (targeted by ATRA), Oestrogen receptor (targeted by Tamoxifen), aromatase (targeted by Letrazole), androgen receptor (targeted by Flutamide, Biclutamide), CD20 (targeted by Rituximab), VEGF-receptor (targeted by Avastin), and the like. The methods and devices provided herein can be used to diagnose diseases other than cancer. In some aspects, malaria can be diagnosed, the method comprising detecting an erythrocyte infected with *Plasmodium*. In another case, a method for diagnosing an HIV infection is provided, the method comprising detecting a lymphocyte or leucocyte infected with the HIV virus using an eDAR method and/or apparatus provided herein. In yet another case, a method for diagnosing a disease associated with a prion is provided, the method comprising detecting a prior in a biological fluid from a human or other animal.

In some aspects, the analyte is a rare cell and the rare cell is a bacterial cell. In some aspects, the bacterial cell is present in a whole blood sample. In other aspects, a device, method, system or apparatus is used to detect the presence of the rare bacterial cell in whole blood. In some aspects a device, method, system or apparatus is used to detect the presence of a rare bacterial cell in a whole blood sample in order to provide a diagnosis, prognosis, or other therapeutic parameter related to characterizing or managing a bacterial infection or sepsis.

Prognosis of Disease

The present disclosure provides methods for a prognosis for a disease or condition associated with the presence of an analyte in a fluid. In some aspects, the analyte can be a biological particle. In some aspects the fluid can be a biological fluid. In some aspects, the method comprises the steps of: (a) detecting the presence or absence of the analyte in an aliquot of a sample from a subject; (b) assigning a value to the aliquot based on the presence or absence of the analyte; (c) directing the flow or collection of the aliquot based on the assigned value; and (d) providing either a good prognosis if no analytes are detected in the sample or a poor prognosis if analytes are detected in the sample.

In some aspects, the aliquot can be assigned a value based on the quantity or the identity of the analytes in the aliquot. In some aspects, a good or poor prognosis can be provided based on the quantity of the analytes in the sample. For example, a good prognosis can be provided if the quantity of the analytes in the sample is less than a predetermined reference value and a poor prognosis is provided if the quantity of the analytes in the sample is equal to or greater than the reference value. In some aspects, a predetermined reference value can be associated with a likelihood of responding to a particular therapy or a likelihood of overall or disease free survival for a period of time, for example at least 6 month, or at least 1, 2, 3, 4, 5, 6, 7, 8, 9, 10, 15, 20, or more years.

In some aspects, a method provided herein can be used to provide a prognosis for any disease associated with a rare particle. In some aspects, a method for providing a prognosis for malaria is provided, the method can comprise determining the number of erythrocytes infected with *Plasmodium* in a blood sample from an individual using an eDAR method and/or apparatus provided herein. In some aspects, either a good prognosis if the total number of infected erythrocytes detected in the blood sample is less than a predetermined reference value or a poor prognosis if the total number of infected erythrocytes detected in the sample is equal to or greater than the reference value can be provided. In some aspects, a method for providing a prognosis for an HIV infection is provided, the method can comprise determining the number of lymphocytes or leucocytes infected with an HIV virus in a blood sample from an individual using an eDAR method and/or apparatus provided herein and providing either a good prognosis if the total number of infected cells detected in the blood sample is less than a predetermined reference value or a poor prognosis if the total number of infected cells detected in the sample is equal to or greater than the reference value. In some aspects, a method for providing a prognosis for a disease associated with a prion is provided, the method can comprise determining the number of prions in a biological fluid sample from a subject using an eDAR method and/or apparatus provided herein and providing either a good prognosis if the total number of prions detected in the sample is less than a predetermined reference value or a poor prognosis if the total number of prions detected in the sample is equal to or greater than the reference value.

In some aspects, the present disclosure provides a method for providing a prognosis for a subject diagnosed with a solid tumor. In some aspects, the method comprises the steps of (a) detecting the presence or absence of a CTC in an aliquot of a blood sample from the subject; (b) assigning a value to the aliquot based on the presence or absence of the CTC; (c) directing the flow or collection of the aliquot based on the assigned value; and (d) providing either a good prognosis if no CTCs are detected or a poor prognosis if a CTC is detected.

In some aspects, a method is provided for providing a prognosis for a subject diagnosed with metastatic cancer. In some aspects the method comprises the steps of (a) detecting the presence or absence of a CTC in an aliquot of a blood sample from the subject; (b) assigning a value to the aliquot based on the number CTCs detected in the aliquot; (c) directing the flow or collection of the aliquot based on the assigned value; and (d) providing either a good prognosis if the total number of CTCs detected in the blood sample is less than a predetermined reference value or a poor prognosis if the total number of CTCs detected in the sample is equal to or greater than the reference value.

In some aspects, a predetermined reference value can be associated with a likelihood of responding to a particular therapy or a likelihood of overall or disease free survival for a period of time, for example at least 6 month, or at least 1, 2, 3, 4, 5, 6, 7, 8, 9, 10, 15, 20, or more years.

Response of Disease to Treatment

The present disclosure provides methods for monitoring the progression of a disease or the response to a therapy. In some aspects, the method can comprise detecting an analyte in a fluid sample. In some aspects, the method comprises the steps of: (a) detecting the presence or absence of the analyte in a plurality of aliquots of a first biological sample taken from a subject at a first time; (b) assigning a value to the aliquots based on the presence, absence, quantity, or identity of the rare particle; (c) determining the total value of all the aliquots from the first sample; (d) detecting the presence or absence of the analyte in a plurality of aliquots of a second biological sample taken from the subject at a second time; (e) assigning a value to the aliquots based on the presence, absence, quantity, or identity of the analyte; (f) determining the total value of all the aliquots from the second sample; and (g) comparing the total value assigned to the first sample to the total value assigned to the second sample, wherein an increased value assigned to the second sample as compared to the first sample is correlated with a progression of the disease and/or a poor response to the therapy and/or a decreased value assigned to the second sample as compared to the first sample is correlated with a regression of the disease and/or a good response to the therapy. In some aspects, the aliquots can further be directed into a particular channel or chamber (channeled) based on the value assigned for collection, further enrichment, or further analysis.

In some aspects, methods of monitoring disease progression or response to therapy can be employed on a regular basis after diagnosis of the disease or initiation of the treatment regime. For example, samples can be collected from a subject at least once a year, at least twice a year, at least 3, 4, 5, 6, 7, 8, 9, 10, or more times a year, or at least about 3, 4, 5, 6, 7, 8, 9, 10, or more times a year. In some aspects, the subject can be monitored once a month, or at least 2, 3, 4, 5, 6, 7, 8, 9, 10, or more times a month. In some aspects, the subject can be monitored about once a month, or at least about 2, 3, 4, 5, 6, 7, 8, 9, 10, or more times a month.

In some aspects, wherein a progression of the disease or poor response to a therapy is found, the method can further comprise a step of assigning a therapy, increasing a dosage regime, changing a therapeutic regime, and the like. In some aspects, the disease or condition associated with a rare particle can be cancer, malaria, HIV/Aids, a prion-related disease, or the like.

Digital Processing Devices

In some embodiments, the platforms, systems, media, and methods described herein include a digital processing device, or use of the same. In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 28:
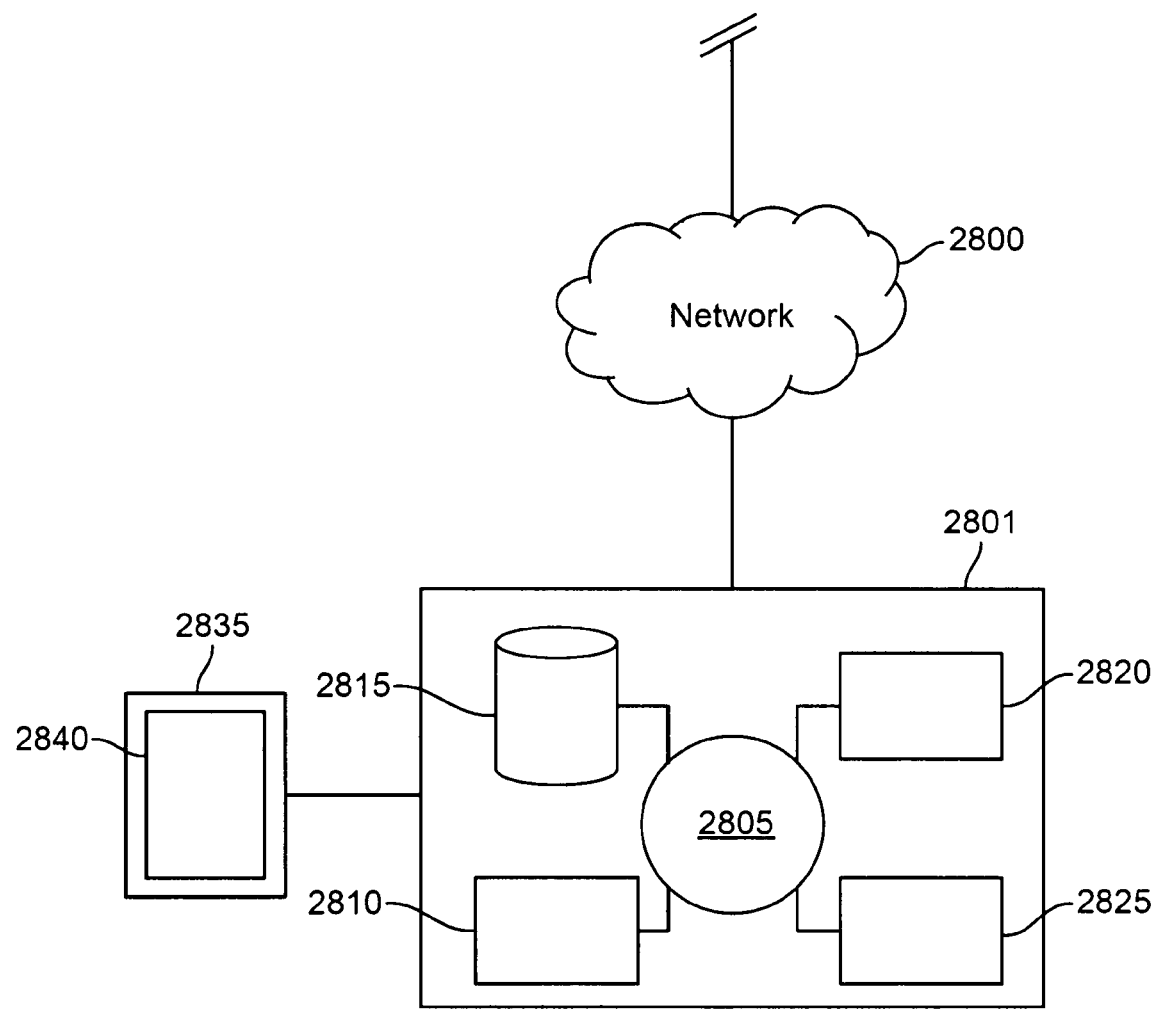
FIG. 28 shows, an exemplary digital processing device programmed or otherwise configured to operate a particle collection device.

Referring to FIG. 28, in a particular embodiment, an exemplary digital processing device 2801 is programmed or otherwise configured to operate a particle collection device. The device 2801 can regulate various aspects of the particle collection device of the present disclosure, such as, for example, performing processing steps. In this embodiment, the digital processing device 2801 includes a central processing unit (CPU, also "processor" and "computer processor" herein) 2805, which can be a single core or multi core processor, or a plurality of processors for parallel processing. The digital processing device 2801 also includes memory or memory location 2810 (e.g., random-access memory, read-only memory, flash memory), electronic storage unit 2815 (e.g., hard disk), communication interface 2820 (e.g., network adapter) for communicating with one or more other systems, and peripheral devices 2825, such as cache, other memory, data storage and/or electronic display adapters. The memory 2810, storage unit 2815, interface 2820 and peripheral devices 2825 are in communication with the CPU 2805 through a communication bus (solid lines), such as a motherboard. The storage unit 2815 can be a data storage unit (or data repository) for storing data. The digital processing device 2801 can be operatively coupled to a computer network ("network") 2830 with the aid of the communication interface 2820. The network 2830 can be the Internet, an internet and/or extranet, or an intranet and/or extranet that is in communication with the Internet. The network 2830 in some cases is a telecommunication and/or data network. The network 2830 can include one or more computer servers, which can enable distributed computing, such as cloud computing. The network 2830, in some cases with the aid of the device 2801, can implement a peer-to-peer network, which may enable devices coupled to the device 2801 to behave as a client or a server.

Continuing to refer to FIG. 28, the CPU 2805 can execute a sequence of machine-readable instructions, which can be embodied in a program or software. The instructions may be stored in a memory location, such as the memory 2810. The instructions can be directed to the CPU 2805, which can subsequently program or otherwise configure the CPU 2805 to implement methods of the present disclosure. Examples of operations performed by the CPU 2805 can include fetch, decode, execute, and write back. The CPU 2805 can be part of a circuit, such as an integrated circuit. One or more other components of the device 2801 can be included in the circuit. In some cases, the circuit is an application specific integrated circuit (ASIC) or a field programmable gate array (FPGA).

Continuing to refer to FIG. 28, the storage unit 2815 can store files, such as drivers, libraries and saved programs. The storage unit 2815 can store user data, e.g., user preferences and user programs. The digital processing device 2801 in some cases can include one or more additional data storage units that are external, such as located on a remote server that is in communication through an intranet or the Internet.

Continuing to refer to FIG. 28, the digital processing device 2801 can communicate with one or more remote computer systems through the network 2830. For instance, the device 2801 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 2801, such as, for example, on the memory 2810 or electronic storage unit 2815. The machine executable or machine readable code can be provided in the form of software. During use, the code can be executed by the processor 2805. In some cases, the code can be retrieved from the storage unit 2815 and stored on the memory 2810 for ready access by the processor 2805. In some situations, the electronic storage unit 1315 can be precluded, and machine-executable instructions are stored on memory 2810.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Programs

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Applications

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Applications

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Applications

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB.NET, or combinations thereof. Compilation is often performed, at least in part, to create an executable program. In some embodiments, a computer program includes one or more executable complied applications.

Web Browser Plug-Ins

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB.NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called microbrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 1.1.5.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice. The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

As used herein and unless otherwise indicated, the terms "a" and "an" are taken to mean "one," "at least one" or "one or more." Unless otherwise required by context, singular terms used herein shall include pluralities and plural terms shall include the singular.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to."

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

Words using the singular or plural number also include the plural and singular number, respectively. Additionally, the words "herein," "above," and "below" and words of similar import, when used in this application, shall refer to this application as a whole and not to any particular portions of the application.

EXAMPLES

The following examples are included to further describe some aspects of the present invention, and should not be used to limit the scope of the invention.

Example 1

Ensemble-Decision Aliquot Ranking Based on Microfluidic Components for Large-Capacity Trapping of Circulating Tumor Cells This example describes and validates a novel eDAR platform for isolating particles including cells according to an aspect of the present disclosure.

Two factors that determined the feature and performance of an eDAR platform are an efficient and active sorting scheme and a subsequent efficient purification (e.g., purification chamber) scheme. The present eDAR-platform optimizes these two components. In one example, the eDAR platform can include an integrated filtration area fabricated by standard lithography methods. The microfluidic chip can be composed of two layers on a silicon master and can be fabricated with one-step replica molding into polydimethylsiloxane (PDMS). The microfluidic chip can be finished with bonding to a glass substrate. The entire system can include an active sorting scheme. The analytical performance of the microfluidic chip and hydrodynamic switching mechanisms can be optimized for a particular recovery efficiency (e.g., 95%), a particular false positive rate (e.g., 0) and a particular throughput (e.g., 4.8 mL of whole blood per hour).

The Microfluidic Chip

The microfluidic chip used in this example had two functional areas integrated in the same design, the eDAR sorting area and the filtration unit based on slit structures. The main channel in the sorting unit, which introduced the blood into the sorting junction, had a height of 50 m and width of 150 µm; all the other 4 channels were 50 µm tall and 200 m wide. The slit-filters were 5 m tall and 5 m wide. The maximum number of slits tested was 20,000.

The silicon master was fabricated using two photolithography processes (FIGS. 5, 20 and 21). The features were designed using AutoCAD (Autodesk, San Rafael, Calif.), and written on a chrome mask (TRICR Corporation, SF, CA). Positive resist lithography and deep reactive ion etching (DRIE) were chosen for forming the first layer, the micro-filter feature. AZ 1512 was used as a positive photoresist, which was provided by Micromanufacturing Facility (MMF) at The University of Washington. DRIE process was optimized to achieve a depth in the range of 4.5-5 µm. The second layer of the eDAR feature was fabricated using the SU-8-3050 as a negative photoresist (MicroChem, Newton, Mass.), and the height of the feature was controlled to be 50 µm. After the master was silanized using tridecafluoro-1,1, 2,2-tetrahydrooctyl-1-trichlorosilane (Sigma-Aldrich, St. Louis, Mo.), uncured PDMS was poured onto the silicon wafer and baked for 2 hours at 70° C. The piece of PDMS with the desired micro-feature was peeled off the silicon master, and then bonded with a piece of cover glass using the standard process of plasma oxidation.

Biological and Clinical Samples

Three breast cancer cell lines, SKBr-3, MCF-7, and MDA-MB-231 cells (American Type Culture Collection (ATCC), Manassas, Va.) were used to characterize and optimize the eDAR system. SKBr-3 cells were cultured in McCoy's 5, MCF-7 was cultured in Eagle's Minimum Essential Medium (EMEM), and MDA-MB-231 was cultured in Dulbecco's Modified Eagle's Medium (DMEM) (ATCC, Manassas, Va.). All cell culture media also contained 2 mM L-glutamine, 10% fetal bovine serum (FBS) (ATCC, Manassas, Va.), and 50 µg/mL penicillin/streptomycin (ATCC, Manassas, Va.). Incubations were done at 37° C. with 5% $CO_2$ in a humidified environment. The MDA-MB-231-GFP cell line was provided by Prof. Gail Sonenshein at Tufts University and cultured in the DMEM medium with 10% FBS and 1 µg/mL puromycin (Life Technologies, Carlsbad, Calif.). Control blood from healthy donors was purchased from Plasma International Lab (Everett, Wash.); the first tube of the blood draw was discarded to prevent any possible contamination from skin cells. Whole blood samples were drawn from patients with metastatic pancreatic cancer based on a protocol approved by Fred Hutchinson Cancer Research Center's institutional review board. Patient samples were collected at the Seattle Cancer Care Alliance (SCCA) using Vacutainer tubes (BD, Franklin Lakes, N.J.) containing EDTA as an anti-coagulant, stored at 4° C., and analyzed within 4 hours.

Sample Preparation and eDAR Analysis

Isoton (Beckman Coulter Inc., Chino, Calif.) was used as the buffer for all the experiments unless otherwise specified. For a typical eDAR experiment, 1 mL of whole blood samples was labeled with anti-EpCAM conjugated with phycoerythrin (PE) (Lot No. 515776, Abnova, Walnut, Calif.) for 30 minutes at room temperature in dark. All the labeling parameters have been optimized. The labeled samples were diluted to 14 mL and then centrifuged to remove the free antibodies. The final volume was adjusted to be the same as the initial volume. The prepared sample was next injected to the microfluidic chip using a syringe pump. Traces from fiber-coupled avalanche photodiodes (APDs) (Excelitas Technologies, Waltham, Mass.) were collected by a PCI data acquisition card (PCI 6602, National Instruments, Austin, Tex.). The sorting process of eDAR was automatically controlled using a home-written LabVIEW (National Instruments, Austin, Tex.) script and a field-programmable-gate-array (FPGA) device built in house. The hydrodynamic switching, which collected the sorted aliquots, was controlled by a solenoid (INKA1226212H) purchased from the Lee Company (Westbrook, Conn.).

After all the positive aliquots were collected onto the filtration area, isoton was used to quickly wash the filtration area in less than 1 minute. If any cytoplasmic markers were used for the secondary labeling, 4% of paraformaldehyde (PFA) was loaded into the filtration area to fix the cells. Surfynol® 465 (Air product, Allentown, Pa.) was used to permeabilize the fixed cells. Anti-EpCAM-PE and anti-Cytokeratin-APC (Lot No. MAB5131, Abnova, Walnut, Calif.) and anti-CD45-fluorescein isothiocyanate (FITC) (Lot No. B116314, BioLegend San Diego, Calif.) were typically used as the antibodies for the secondary labeling. Hoechst (Life Technologies, Carlsbad, Calif.) was also used as the nuclear stain to verify the labeled target was actually nucleated cells.

The method of eDAR was as follows, the blood sample was injected into the microfluidic chip and divided into aliquots. A line-confocal detection scheme was then applied to rank the aliquots as "positive" or "negative," which was determined by the labeling scheme. For example, in many applications, blood was labeled with anti-EpCAM-PE so only an aliquot that had a fluorescent signal from the particular dye conjugated to that antibody was ranked as a positive event. An automatic feedback scheme was applied to generate a switch of the direction of blood flow, which permitted the positive aliquot to be collected quickly. Due to the very low concentration of CTCs, more than 99.999% of the aliquots were discarded because of the absence of the desired fluorescence signal. Those aliquots that gave the positive fluorescence signal were transferred to another area on the microfluidic chip to be further purified and then counted. A series of downstream analyses can be performed on the trapped cells.

Redesigned Hydrodynamic Sorting Scheme.

Previously, the eDAR had a mechanical valve to control the active sorting step, which was fast (about 2 milliseconds response time) and robust compared to other reported switching mechanisms, such as the electroosmotic flow or the sol-gel transformation. Although promising, some design factors of this mechanical valve scheme potentially constrained the potential application of eDAR. To form the mechanical valve on the microfluidic chip, 3 individual structural layers were required—the solenoid, its PDMS thread, and the microchannels on a 150 in PDMS film. This would make the microfluidic chip preparation complicated and time-consuming. Another shortcoming was the direct contact between the captured blood aliquots and the mechanical valve, which potentially increased the risk of the loss or damage of CTCs. In the present example, the solenoid was replaced with an off-chip model, which is normally closed but can be opened in 2 to 3 milliseconds when a 5V DC voltage is applied. Because this in-line solenoid was not a part of the microfluidic chip, the preparation of the microfluidic device was significantly simplified. The solenoids can be easily connected with any microchannels to test hydrodynamic sorting schemes. Eight different schemes were designed and tested (FIG. 3) to drive the fluidic switch. Because of the structure of this type of solenoid and the elastic nature of PDMS, the fluidic performance varied (Table 1), and each scheme was characterized for the best performance.

After characterization and optimization, the structure of the platform and the corresponding scheme of the hydrodynamic sorting were chosen for eDAR (FIG. 4). The labeled blood sample was injected into the top channel of the microfluidic chip using a syringe pump (FIG. 4A). Two side channels, where buffer flowed through, were used to control the active sorting step. There were two ports placed on the right-side channel, and both of them were connected to a pressurized buffer source. The normally closed solenoid was connected to the port near the sorting junction to control the hydrodynamic switch. There were two channels after the sorting junction. The one on the left was used to collect positive aliquots and deliver them to the filtration and collection area for further purification (e.g., purification chamber); the one on the right was the waste collection channel where all the negative aliquots flowed through.

When those aliquots were ranked as "negative" (FIG. 4B), there was no voltage applied on the solenoid so it was closed. An initial pressure drop was set between the No. 1 and 3 buffer sources so the blood could only flow into the channel that collected the waste, which is also shown in the bright field image in FIG. 4B. When a positive event was detected by the first detection window, a 5V DC voltage was immediately applied on the solenoid to open the buffer flow from the No. 2 buffer reservoir. This decreased the flow resistance of the buffer channel on the right side and generated a higher flow rate there. The blood flow was pushed from the right side to the left to collect the positive aliquot (FIG. 4C). After this aliquot was collected and confirmed by the second detection window, that solenoid was closed to switch the blood flow back to the waste collection channel (FIG. 4D). The time required for the switch-over and back was determined to be 2 to 3 milliseconds for each (FIG. 5). This process was stable enough for eDAR even after more than $10^5$ on-off cycles tested. The in-line solenoid was placed on the buffer line so blood could not come into contact with the solenoid, which eliminated the possibility of the blood-coagulation and cross-contamination. Moreover, in this scheme, there was a constant flow of buffer in the CTC collection channel during the eDAR process. This improved the efficiency of the subsequent purification (e.g., purification chamber) step and prevented the formation of aggregates of cells.

In some aspects of the present example, positive aliquots can be collected onto the filtration area and Isoton used to wash the filtration area in less than 1 minute. Cytoplasmic markers can be used for secondary labeling and can involve loading of 4% paraformaldehyde into the filtration area to fix the cells. Surfynol® 465 (Air product, Allentown, Pa.) can be used to permeabilize fixed cells. Anti-EpCAM-PE and anti-Cytokeratin-APC (Abnova, Walnut, Calif.) and anti-CD45-fluorescein isothiocyanate (FITC) (BioLegend San Diego, Calif.) can be used secondary labeling. Hoechst (Life Technologies, Carlsbad, Calif.) can be used as a nuclear stain to verify nucleated cells.

Design of the Purification (e.g., Purification Chamber) Mechanism

Yet another aspect of the example can include a new scheme of on-chip filtration based micro-slit structures that can be made of PDMS and may not require additional layers (FIG. 7A). FIG. 7A shows the basic structure of an example of these microslits, which was used to capture the CTCs without retaining any red blood cells (RBCs). The size of the slit was optimized to be 5 m tall and 5 µm wide (FIG. 7B), to avoid loss of any small CTCs. Many WBCs were not captured using this size of filter, which is smaller than the ones used in most of the CTC methods based on filtration. Because the micro-filter was made of PDMS and bonded with a piece of coverslip, the imaging quality was improved significantly (FIGS. 7C and 7D) compared to the polycarbonate filter, which is not fully transparent and can generate the scattering and aberration. Moreover, because the cells could only be trapped along the array of slits, they could be easily referenced and tracked; in many other methods, the cells are distributed randomly on the surface. This trapping along the slits made the imaging procedure faster and the results of enumeration more accurate. The slits also made it faster and more efficient to perform the secondary labeling on the trapped CTCs. FIG. 7E shows that two cancer cells labeled with anti-EpCAM-PE were trapped on the microslit. Cells were fixed, permeabilized, and labeled using anti-Cytokeratin-Alexa488, anti-Her2-Alexa647 and Hoechst. Fluorescence images showed the expression of these markers on these two cells clearly, and the bright field image also confirmed their morphology. Two cells were also labeled with anti-CD45-Alexa700 as a negative control marker, and no signal from the color channel corresponded to this tag.

Characterization and Analytical Performance of eDAR

The efficiency of the active sorting step was monitored in real time. FIG. 6 shows a small portion of the APD data from a pancreatic cancer patient sample. The "Decision APD trace" was from the first detection window that ranked the aliquots and controlled the sorting. The two peaks at 978 and 1298 milliseconds represented two CTCs labeled with anti-EpCAM-PE that triggered the aliquot sorting. The two peaks of the "Confirmation APD trace" show that two cancer cells flowed through the second detection window located on the collection channel, confirming that the two positive aliquots were actually sorted. It is worthwhile to point out that the background change from the second detector (FIG. 6A) also confirmed that only a small portion of blood was collected by eDAR, contributing to the high enrichment ratio of CTCs (up to a million fold for a typical clinical sample).

Because the labeled CTC had to flow from the first detection window to the second one, a time difference between the decision APD peak and its confirmation signal was observed. This time difference was defined as the transit time of the sorted CTCs, which can vary because the CTCs can have different linear flow rates due to the nature of laminar flow in the microchannel. FIG. 6B shows the distribution histogram of the transit time at flow rates of 40 and 80 µL/min. Generally, a higher volumetric flow rate of the blood resulted in a shortened transit time of the sorted CTCs (FIG. 6C). When the flow rate was 90 µL/min, the average transit time was lowered to 4 milliseconds, very close to the switching time of the sorting scheme (2 to 3 milliseconds), which implies that this is the limit for the throughput for this particular embodiment of a design for eDAR. In other embodiments, the present eDAR design may yield transit times less than 2 milliseconds.

If the transit time for a sorted CTC was shorter than the hydrodynamic switching time, the cell may not have been reliably sorted on this platform. The sorting efficiency was thus defined as the number of collected events versus the total number of events that triggered the sorting. FIG. 6D shows the values of sorting efficiency at the flow rate of 30 to 100 µL/min. When the flow rate was 30 µL/min, the sorting efficiency was almost 100% because the average transit time at that flow rate was around 10 milliseconds (FIG. 6D). This transit time was long enough for the active sorting step to collect the CTCs. The sorting efficiency decreased to 90% at the flow rate of 80 µL/min, and then dropped to 49% when the flow rate was 90 µL/min. FIG. 6D also shows the recovery efficiency of eDAR at different flow rates, which had a similar trend compared to the sorting efficiency. However, the recovery efficiency was defined as the number of spiked-in cells versus the number of recovered cells counted using multicolor fluorescence imaging on the microfluidic chip. This performance is a combination of many factors, including the antibody-labeling efficiency, the line-confocal detection efficiency and the sorting efficiency. This explains the difference between the recovery and sorting efficiency at the same flow rate. As a result, for this current generation of eDAR, the upper limit of the throughput was 80 µL/min (12.5 minutes for 1 mL of blood) with an 88% recovery ratio. Although this throughput is higher than most CTC technologies for the analysis of whole blood, it can be further improved by designing a wider blood inlet channel or moving the first detection beam farther up.

Three to 975 MCF-7 cells were spiked into 1 mL of healthy blood to analyze the recovery efficiency at the flow rate of 50 µL/min. To ensure the accuracy of the cell numbers at the low end, a capillary counting method was used to precisely spike in cultured cells when the concentration was lower than 100 cells/mL. The average recovery ratio was 95% with an $R^2$ value of 0.998 (FIG. 6E), which is a little higher than the first generation of eDAR (93%). Because the concentration of CTCs is usually very low, the enumeration results were affected by the Poisson distribution. In this case, the ability to analyze a larger volume of whole blood sample with an acceptable throughput and recovery ratio was very important. The same number of MCF-7 cells was spiked into 1, 5 and 10 mL of healthy blood, and then these three samples were analyzed at the flow rate of 50 µL/min. There was no significant change in their recovery ratio (FIG. 6F), which shows that the method is capable of running a large amount of whole blood with high efficiency and throughput.

Although EpCAM was used in most of the CTC studies to select tumor cells, increasingly more studies have reported that CTCs with a low EpCAM expression have more mesenchymal characteristics and are more aggressive. The latest eDAR platform is sufficiently flexible to use any labeling scheme to select rare cells to capture tumor cells using biomarkers other than EpCAM. Three schemes were designed to select different cultured breast cancer cell lines (FIG. 6G). EpCAM was used to select MCF-7 cells, Her-2 was used to select SKBr-3 cells, and EGFR was used to select MDA-MB-231 cells. All these three schemes isolated and trapped the targeted cells with a recovery ratio higher than 88%. Another unique and important feature of eDAR is the independence of where the marker is located. For example, in other technologies, such as the surface capture methods or immunomagnetic methods, only can capture the antigens on the cell surface. The present method was able to select cells with an intracellular marker, such as GFP (FIG. 6D). The recovery ratio of the MDA-MB-231-GFP cells spiked into whole human blood was 91% (FIG. 6G). Since fluorescent proteins are widely used in animal models to study the progression and mechanisms of metastasis, eDAR is an ideal tool to select CTCs in these models.

Example 2

Dual Capture eDAR

This example describes a "dual-capture" version of eDAR according to an aspect of the present disclosure. The dual-capture eDAR can separate two different subpopulations of CTCs from the same human blood sample on the same microfluidic device simultaneously. Those two subpopulations can be trapped separately on two different regions on the microfluidic chip, with a high recovery and purity, respectively.

FIG. 8 shows the general structure of the microfluidic device. Blood samples were pre-labeled with two kinds of antibodies conjugated with different fluorescent tags. For example, the blood sample was labeled with an epithelial marker, such as anti-EpCAM conjugated with PE, as well as a mesenchymal marker, such as anti-EGFR or anti-vimentin conjugated with another fluorophore having a different wavelength of emission compared to PE, such as FITC. The labeled blood sample was injected into the microfluidic chip, the CTCs with EpCAM expression could be detected using the line-confocal scheme with a peak in the yellow channel, and then an active sorting event was triggered to collect that aliquot into the collection channel #1. Similarly, if the aliquot was ranked as positive to the mesenchymal markers, it was sorted to the collection channel #2. The two subpopulations were then trapped and enriched on the microfluidic chip separately. The filtration area was built on the same design of microslits used in the second generation of eDAR.

The fluidic switching scheme is summarized as follows. When the aliquots were ranked as negative to any marker applied, then both of the solenoids in FIG. 8 were closed. If the pressure on the two side channels was balanced, the blood flowed to the bottom center channel, which was used to collect the waste. When the aliquots were ranked as positive to epithelial marker only, solenoid #2 opened immediately so the blood flow was pushed to the collection channel on the left (FIG. 9B). After the aliquot was collected, solenoid #2 closed again, so the blood flow switched back to the center. When the aliquots were ranked as positive to epithelial marker only, solenoid #1 opened immediately so the blood flow was pushed to the right side (FIG. 9C). The response time for the two types of eDAR sorting events was about 2 to 3 milliseconds.

FIG. 8 shows the general structure of the "dual-capture" eDAR. Labeled blood was introduced into the main channel on the top. Buffer was flowing in the two side channels to control the hydrodynamic switching of the blood flow using two solenoids. Two subpopulations of CTCs were separated and trapped on two different filtration areas on the same microfluidic chip.

FIG. 9 depicts bright field images of the three status of the blood flow. A) The blood flowed into the waste collection channel, because the aliquots were ranked as negative to either markers. B) The blood was switched to the collection channel #1, and the first subpopulation of CTCs transferred to there. C) The blood was switched to the collection channel #2, and the second subpopulation of CTCs transferred there.

Example 3

Multi-Stage Sorting and Dispersion

MCF-7 cell line was obtained from American Type Culture Collection (ATCC, Manassas, Va.). Cells were cultured at 37° C. and 5% $CO_2$ in EMEM media (ATCC). Media was supplemented with 5% v/v fetal bovine serum (FBS) and 1% v/v penicillin streptomycin (both from Sigma, St. Louis, Mo.).

Healthy, whole blood samples were obtained from PlasmaLab International (Everett, Wash.).

Antibodies were purchased from BioLegend, Inc. (San Diego, Calif.) apart from phycoerythrin (PE)-anti-EpCAM (Abcam, Cambridge, Mass.). Isoton II buffer, used as a sheath flow for eDAR, was purchased from Beckman Coulter (Brea, Calif.). Bovine serum albumin (BSA) and TWEEN 20 were purchased from Sigma (St. Louis, Mo.). Two solutions were prepared in isoton: one at 0.1% BSA w/w used for labeling and the second at 1% BSA/0.05% TWEEN20 w/w and used for pretreating materials. Glycerol was purchased from EMD (Billerica, Mass.) and a 25% w/w solution was prepared in Isoton to simulate the fluidic characteristics of blood for sorting experiments. This solution was mixed in a 30/70 ratio with green food dye (COV Extract Company, Rockford Ohio) for experiments where images of the sorting were needed.

Silicon masters were made using standard photolithographic techniques using SU-8 2050 (MicroChem, Westborough, Mass.) for spin coating. Chips were made from PDMS in a 1:10 ratio of precursor to polymer base, fully cured, and sealed to a glass substrate immediately following exposure to $O_2$ plasma for one minute. If not used immediately, chips were covered and stored until use, but not longer than one month.

To test different chip designs for their ability to stretch an aliquot, 10 µl PE-goat-anti-mouse antibody was added to 40 µl filtered isoton in a centrifugal filter tube (EMD Millipore, Billerica, Mass.) and spun at 14,000 RPM for 5 min to remove aggregates. This was added to 1 ml 25% glycerol solution w/w in isoton. Approximately 10 µm 1500 yellow fluorescent beads (Duke Scientific, Palo Alto, Calif.) were added. The sample was run on a multi-stage fluorescence activated sorting after first-stage eDAR sorting chip and sorting established. The APD trace was collected, using the beads to trigger sorting events, and sorted dye peaks were analyzed.

MCF7 cells were labeled with 30 µl PE-anti-EpCAM for 3 hours. After washing, cells were counted and approximately 100 cells were spiked into 0.5 ml blood. Blood was sorted on a chip. Upon establishing sorting, a fresh tube, pre-treated with 1% BSA 0.05% TWEEN20, was plugged into the collection outlet and run into a pre-treated 15 ml centrifuge tube. After sorting, collected cells were spun down at 450 RCF for 10 min, and supernatant removed. 15 µl PE-anti-CD45 (spun to remove aggregates) was added for 3 hours. The sample was washed with isoton+0.1% BSA and run on a new chip, only punched in the inlet and outlet for ease of use. The trace was collected and total PE labeled cells counted using MATLAB analysis. As a control, the above process was repeated without the addition of PE-anti-CD45 and the PE peaks were counted and confirmed to match with the number of PE peaks from the first sorting experiment.

MCF7 cells were labeled with 30 µl PE-anti-EpCAM (spun to remove aggregates) for 3 hours. After washing, cells were counted and a known quantity (~100 cells) were spiked in to 0.5 ml blood. Blood was sorted on a chip. Upon establishing sorting, a fresh tube, pre-treated with 1% BSA 0.05% TWEEN20 was plugged into the collection outlet and run into a pre-treated 96-well plate. Cells were collected into the wells of the 96-well plate, manually moving the tube into a new well when a volume of ~250 µl was reached. Upon completion of sorting, the well plate was spun down at 450 rcf for 10 min. Cells were imaged and counted on a Nikon TE 2000 U microscope with a 20×, 0.75 NA objective (Nikon, Tokyo, Japan).

Since eDAR sorts aliquots of whole blood instead of analyzing the cells single file, the running time for a sample is greatly reduced compared to other fluorescent sorting methods. However, inherent to this method is the fact that blood cells will be sorted with the labeled cell of interest. For previous iterations of eDAR, an on-chip filter was used to collect the cells, with slits 5 µm wide. This allowed all the red blood cells and most of the white blood cells to pass through, while retaining even the smallest CTCs. However, cells retained on the filter were time consuming to remove, and the need for improved purity arose if cells were going to be collected directly after sorting. To achieve this, we designed a new chip to include a second sorting junction after the first (see FIG. 18A). The sorted plug is stretched as it passes down the channel separating the two junctions (the dispersion region), and there is a second detection and sorting once the cell reaches the second junction. There are two detection spots, one just before each sorting junction as shown in FIG. 18A.

Figure 24A:
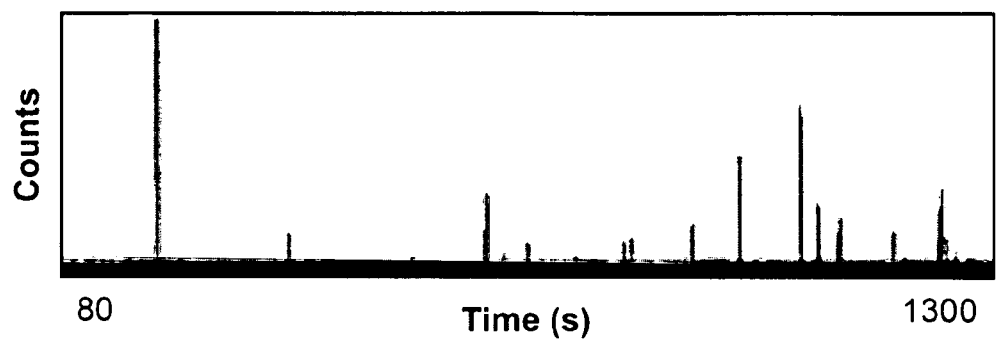
FIG. 24A shows the detection trace from a first sorting junction during a sort.
Figure 24B:
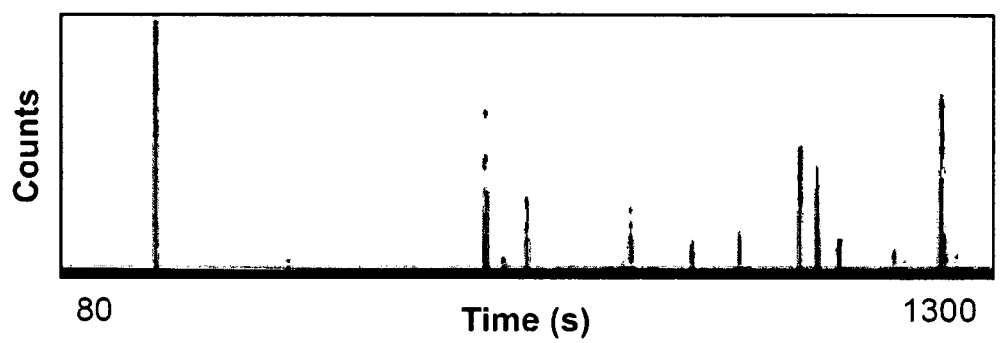
FIG. 24B shows the detection trace from a second sorting junction during a sort.
Figure 24C:
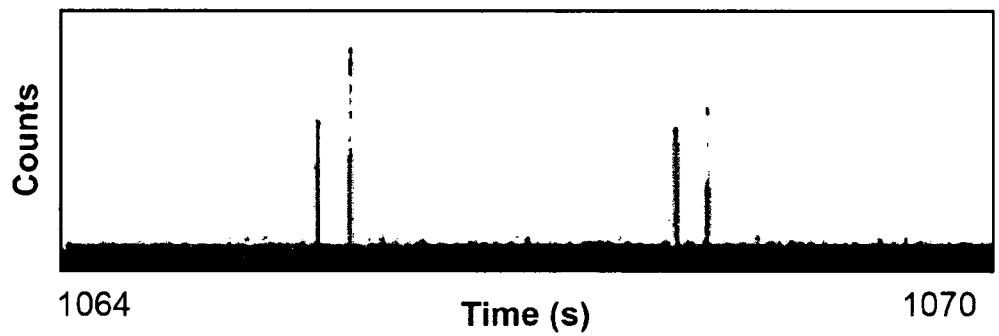
FIG. 24C shows a shorter section of the combined trace of the APD data from the first sorting junction and the second sorting junction.

FIG. 24A and FIG. 24B show the detection trace from the two junctions during a sort. Cells are detected in both junction, as seen on the plots. FIG. 24C shows a shorter section of the combined trace of the APD data from the first sorting junction and the second sorting junction, shown in green and blue respectively. There is a delay time between the sorts, during which the aliquot or fluid volume is stretched and diluted. This means that the concentration of blood cells is reduced and the average distance between cells increased, and the number of these cells sorted a second time is much lower, thus improving the purity, for example, as measured by the number of CTCs sorted per sample divided by the total nucleated cells collected.

To quantify this improvement, MCF7 cells were labeled with PE-anti-EpCAM, washed, counted, and spiked into 0.5 ml of healthy blood. Blood was flowed onto a sequential sorting chip at a rate of 30 µl/min and sorting established by adjusting flow pressures. Once stable sorting pressures were set, the collection outlet tubing was removed and pre-treated tubing (1% BSA and 0.05% tween20 in Isoton) inserted. The outlet from this tubing was placed in a pre-treated 15-ml centrifuge tube and the entire sorted volume, which contains the sorted MCF7 cells, blood cells sorted in each aliquot, and isoton buffer sheath flow, collected. For a sorting experiment with 0.5 ml of blood, this volume was approximately 1 ml. After sorting, the collected volume was centrifuged at 450 rcf for 10 min and supernatant carefully removed to ~300 µl. 15 µl of PE-anti-CD45 was added and cells were labeled for 3 hours, washed, and the supernatant removed down to 1 ml. This was run through a clean chip, only punched at the inlet and one outlet, and the APD trace collected and analyzed. As a control, the above process was conducted without the addition of the PE-anti-CD45 antibodies, and the number of PE peaks correlated with the number of PE peaks from the first sorting experiment, thus confirming that cells are not lost during the labeling process.

The number of peaks in the trace yields the total nucleated cells sorted, both the PE-labeled MCF7 cells from the initial sorting and the PE-labeled white blood cells labeled after sorting. To calculate the purity, the number of MCF7 cells sorted was divided by total nucleated cells. The number of MCF7 cells sorted was obtained from number of sorting events in the first sorting experiment. For 1-stage sorting, we calculated a purity of about 1%. For a 2-stage sort, where the two junctions are separated by a 3-cm channel, we achieve about 15% purity.

The data presented above for a 3-cm straight channel separating the two junctions shows about 15× increase in purity. This is driven by the stretching and diluting of the aliquot or fluid volume as it travels between the two sorting junctions. Since mixing is low in laminar flow in microchannels, longer channels are needed to achieve substantial mixing. Thus, the easiest way to improve the purity would be to lengthen the channel between the two junctions. A chip was designed and manufactured with a 5.5 cm channel separating the two junctions, and purities were measured as previously described. This design was found to have a purity of about 21%. Further lengthening should yield even greater purities.

While lengthening the channel between the junctions improves the stretching and the purity, the length of channel needed to drastically improve purity and approach single-cell isolation may be unrealistic. Thus, a more aggressive mixing or separation strategy is needed. There are three ways we employed to stretch the aliquot or fluid volume and improve the purity. One, we designed a "flow stretcher", which comprised a long channel connected by a series of smaller channels (FIG. 20), such that part of the aliquot would go down the first small channel and part would continue down the main channel, until the aliquot had been completely separated into many smaller aliquots or fluid volumes.

Figure 25A:
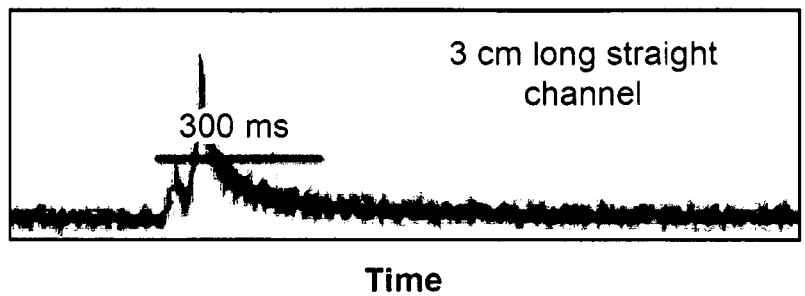
FIGS. 25A-25C show results of flow stretcher stretching tests.
Figure 25B:
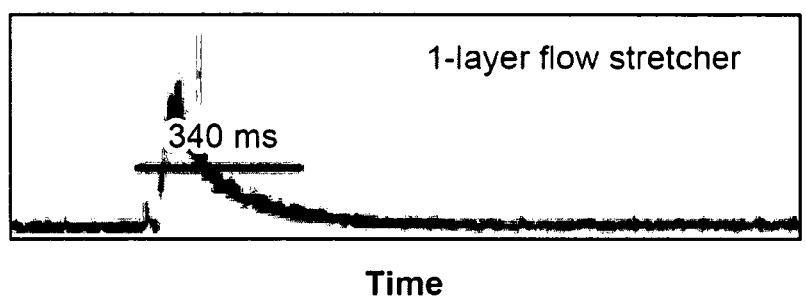
Figure 25C:
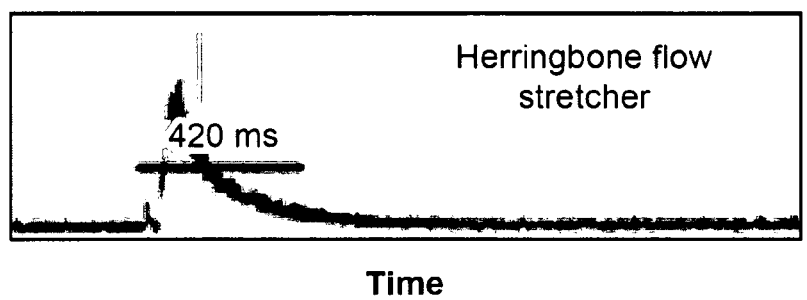

To test this, PE dye was flowed onto the chip in a glycerol solution containing fluorescent beads and sorting established. The sorted aliquot or fluid volume contained the yellow fluorescent bead and a plug of dye, and the improvement to the purity could be estimated from the stretching of the dye aliquot or fluid volume, as visualized by the APD trace, right before the second sorting junction. While this would not give the absolute purity, it was a useful method for comparing between device designs. The longer the aliquot or fluid volume was at the second junction, the more it had been stretched, resulting in fewer blood cells being sorted into the new aliquot or fluid volume. Results using sorted dye aliquots or fluid volume seemed promising (see FIG. 25A-C), but the small size of the side channels needed resulted in the potential for clogging and potential cell loss. FIG. 25 shows the results of the flow stretcher stretching tests, with a straight channel flow stretcher (FIG. 25A-B) and a flow stretcher where herringbone features (FIG. 25C) were used to spread the aliquot or fluid volume laterally across the channel.

The second strategy involved weirs, sections where the channel was briefly reduced in height to 5-30 µm tall, placed along the channel separating the junctions. It was hypothesized that the CTCs or some rare cells, being larger and/or less deformable, would be substantially slowed down at the weirs, and the other blood cells would continue. Another weir-like structure was tested, where a weir filter was employed laterally across the channel, with slits of 30-35 µm.

Figure 26A:
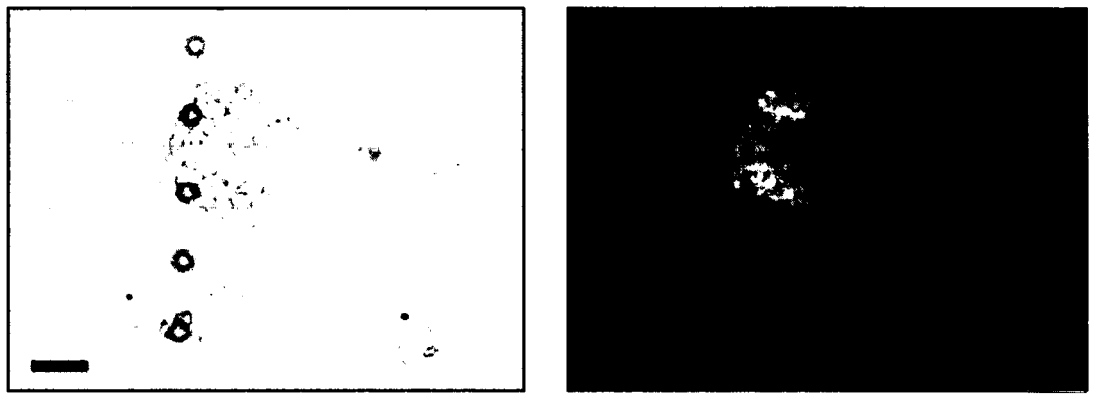
FIGS. 26A-26B show images of cells in filter stretchers.
Figure 26B:
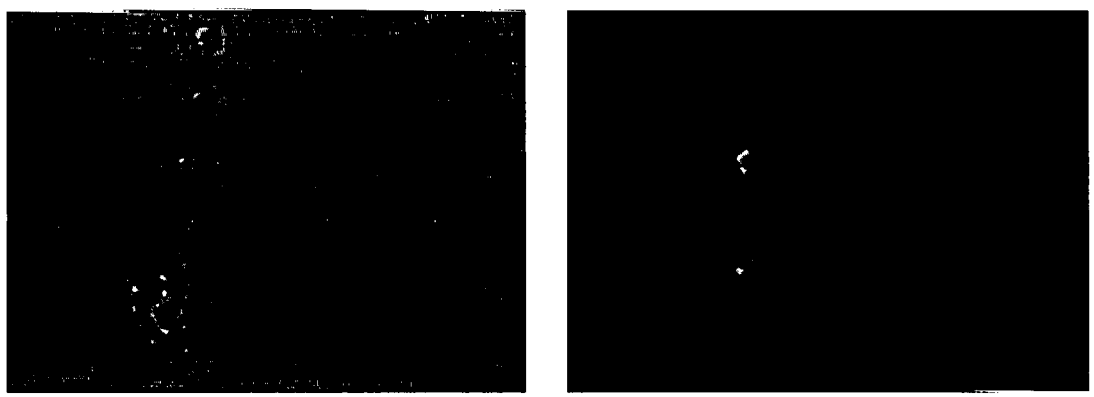

FIG. 26A shows images of cells at the first weir stretcher. The left image in FIG. 26A is a brightfield picture of a section the channel. The slits span the length of the channel, and are 35 µm wide. The right image in FIG. 26A is a fluorescent image of the PE labeled cells. FIG. 26B shows images of cells at the second weir stretcher. The left image in FIG. 26B is a brightfield picture of a section of the channel, in this case with 30 µm wide slits. The right image in FIG. 26B is a fluorescent image of the PE labeled cells.

Finally, we employed a chaotic mixing design using herringbone features at the beginning of the separation channel, to spread the aliquot or fluid volume out laterally before it traveled down the rest of the channel. This design was added to the 5.5 cm straight-channel design, with herringbones used along the first 0.7 cm of the channel. Herringbones are attractive as a mixing strategy for several reasons. First, they are simple to fabricate, requiring only one additionally layer of SU-8 microfabrication and not requiring any valves or complicated features. Second, they have been demonstrated to tunable to a wide variety of applications. Finally, they do not add constrictions where cells could be trapped.

We employed a herringbone design comprising three sections of herringbones (see FIG. 23A): three initial herringbones angled from the inner wall to the outer wall, since we have observed the cells in the aliquot or fluid volume traveling primarily down the inner wall; a section of 12 herringbones staggered with the center more towards the outer wall; and then 12 herringbones staggered the opposite direction. The herringbone height was 30 µm. The first section of straight herringbones were 80 µm wide and spaced 95 µm apart. The second section of herringbones were 70 µm wide and spaced 180 µm apart. The mixing section was 0.7 cm long, with a 4.8 cm straight channel immediately after. This design allows sufficient mixing, so that the cells, rather than traveling in a plug along the outer wall, are separated laterally across the channel. The long section of straight channel would then allow the cells to further separate longitudinally, as the cells near the center of the channel would travel faster than the cells on the outer edges because of the parabolic flow profile. This design yielded 30% purity when tested as previously described. This means that for each sorted CTC or rare cell in the first junction, there are approximately 2.5 white blood cells when it is sorted again in the second junction. Without the second sort, there are approximately 100 white blood cells sorted with each CTC. With an average of 90 MCF7 cells sorted, there were about 225 white blood cells collected after the second sort. Since the total sorted volume is about 1 ml, this corresponds to a white blood cell depletion rate of $2.2 \times 10^4$ or 4.3 log ($5 \times 10^6$ white blood cells/ml in whole blood versus 225 white blood cells/ml in the sorted volume). It is possible that more herringbones with an even longer channel could improve this further. The purity results obtained by the designs tested are summarized in Table 2.

TABLE 2

| Design | Purity (CTCs/total nucleated cells) |
| --- | --- |
| 1-stage eDAR | ~1% |
| 3 cm channel | ~15% |
| 5.5 cm channel | ~21% |
| 5.5 cm channel and herringbone | ~30% |

For this method to be clinically useful, cells needed to be collected in a way they could be easily enumerated, and spike-in recoveries, the traditional method of validating CTC or rare cell isolation techniques, needed to be performed. The eDAR platform has previously been validated with recoveries from different cells lines as well as clinical samples. This method introduces two new elements where cell loss could occur: the second sorting junction and the 96-well plate collection. Thus, recoveries were performed to verify that these elements do not generate cell loss.

Recoveries were conducted with pre-labeled MCF7 cells for simplicity. Previous tests of our in-blood cell labeling steps have been conducted, so for this report we decided to isolate only the features that are new to the system. The first of these is the new fluidic scheme: including two sorting junctions on a chip. Flow was balanced in a similar manner to previous chips, now with flow pressures adjusted for three positions: (1) solenoid one and two off with flow down the first waste channel (the first frame in both FIG. 27A and FIG. 27B), (2) solenoid one open and solenoid two closed with flow down the first collection channel (shown in FIG. 27A), and (3) solenoid one closed and solenoid two open to collect cells down the second collection (FIG. 27B). Sorting on the sequential chip was more stable due to the absence of the on-chip filter introducing potential clogs.

FIG. 27A shows three image frames depicting sorting in a first junction of a sequential sorting fluidics apparatus. Scale bars are 200 µm. The solution is 30% glycerol solution (25% w/w glycerol in Isoton) and 70% green food dye. The three frames show, from left to right: no solenoid open; solenoid opens and flows starts to move to the left; flow is fully down the collection channel. FIG. 27B shows three image frames depicting sorting in a second junction of a sequential sorting fluidics apparatus. Scale bars are 200 µm. The solution is 30% glycerol solution (25% w/w glycerol in Isoton) and 70% green food dye. The three frames show, from left to right: no solenoid open, solenoid opens and flows starts to move to the left, flow is fully down the collection channel.

To collect the PE-anti-EpCAM labeled MCF7 cells after they are sorted at the second junction, pre-treated tubing was inserted into the collection outlet after sorting was established and the outlet of the tubing was mounted above a pre-treated 96 well plate. Tubing and the 96-well plate for collection were pre-treated with a solution of 1% BSA+ 0.05% Tween20 in Isoton to prevent cell sticking. The output volume was collected in a well until it reached ~250 µl, then the tubing was manually moved to the next well. The total output for the sorting of 0.5 ml of blood was ~4 wells or ~1 ml. To enumerate the cells in the wells, the plate was spun down on a plate centrifuge at 450 rcf for 10 min to isolate all the cells to the bottom of the well. Cells could then be counted on a fluorescent microscope with a 20×, 0.75 NA objective. At this stage, if further labeling was required, the supernatant could be removed to a desired labeling volume and antibodies or fixing/permeabilization solutions added. To verify that this step would not introduce cell loss, we spun the cells an additional time, removed the supernatant, added 200 µl isoton buffer+0.1% BSA, spun the plate again and recounted the well. No cell loss was observed. Recoveries for all three designs (3 cm channel, 5.5 cm channel and 5.5 cm channel with herringbones) averaged ~91%, indicating that minimal cell loss is introduced with the new design.

Example 4

Multi-Stage Sorting and Dispersion with Particle Capture and Release

This example describes a "capture and release" version of the multi-stage sorting apparatus according to an aspect of the present disclosure and a method of performing particle capture and release according to an aspect of the present disclosure. Capture and release of particles or cells from a filter or barrier during or following sorting allows for a greater number of assays to be performed on the particles found. For example, CTCs can be captured with high purity, labeled with multiple fluorescently tagged antibodies, fluorescently imaged, then released into a vial and analyzed using techniques such as polymerase chain reaction and/or genetic sequencing.

Particle Capture

After particles, such as cells, are purified and concentrated by two-stage sorting and one or more dispersion operation using two sorting stages and at least one dispersion stage, the particles are collected using a filter element such as shown in FIG. 7A and FIG. 29A.

A predetermined number of SKBr-3 breast cancer cell line cells was added to 4 mL of whole blood (e.g., which, prior to addition of SKBR-3 cells contained a plurality of cells but no SKBr-3 cells or other CTCs) and labeled with an anti-EpCAM antibody conjugated with phycoerythrin. The whole blood spiked with SKBr-3 cells (e.g., the sample) was separated using two-stage sorting comprising a dispersion operation, as described herein, and introduced into a filtration area as in FIG. 29A for particle capture.

The cells were introduced into the filtration area via a flow path from the second sorting stage. It is contemplated that, in addition to the configuration shown in FIG. 29A, a flow path connecting the second sorting stage and the filtration area through which cells are introduced to the filtration area can be oriented parallel to, perpendicular to, or at an angle relative to a filter of the filtration area. After introduction of cells into the filtration area, cells were captured by being allowed to associate with (e.g., contact) the filter under positive fluid flow conditions.

FIG. 29A shows two separate flow paths (e.g., a second and a third flow path) connected to the filtration area upstream of the filter in addition to the flow path connecting the second sorting stage to the filtration area. It is contemplated that a filtration area may have 1, 2, 3, 4, 5, 6, 7, 8, 9, 10, or more than 10 flow paths connected to the filtration area upstream of the filter. During introduction of the cells into the filtration area through the flow path connecting the second sorting stage to the filtration area, the second and third flow paths were closed. It is contemplated that, at least one flow path in addition to that used to introduce cells to the filtration area can be open during cell capture.

After the cells were sorted and captured in the filter, a buffer comprising anti-Cytokeratin-APC (e.g., an additional fluid) was flowed into the filtration area via the second flow path, which comprised an injection port and was separate from the flow path connecting the second sorting stage to the filtration area. In some cases, an additional fluid comprising an antibody is introduced into the filtration via the same flow path as was used to introduce the cells into the filtration area.

Fluorescence imaging was performed to count the number of target cells captured in the filter. Briefly, cells captured in the filter were imaged and counted using a Nikon TE 2000 U microscope (e.g., a Nikon TE 2000 U microscope, a MiSelect R instrument (MiCareo Taiwan Co., Ltd., Taipei Taiwan), or the like) with a 20×, 0.75 NA objective (Nikon, Tokyo, Japan), a detector, and a source of electromagnetic radiation. A recovery ratio (e.g., recovery efficiency) was determined by comparing the number of target cells detected after capture (e.g., target cells imaged in a filtration area, such as is shown in FIGS. 29A, 29B, and 31) or collection to the known number of target cells added to the blood. The average recovery ratio showed no significant variation from the recovery ratios of the sorting stages, indicating that the cell capture filter was 100% successful at retaining the target cells exiting the sorting stages or essentially 100% successful at retaining the target cells exiting the sorting stages.

In some cases, target cells present in the blood sample prior to injection into the first sorting stage but not detected in the captured or collected cell populations are trapped in dead volume or by cellular adhesion prior to being injected into the first sorting stage. Loss of cells in these ways impacts the calculated recovery ratio; however, no quantifiable cell loss is observed after injection into the first sorting stage. Depending on the amount of dead volume and/or cellular adhesion prior to injection of cells into the first sorting stage, the recovery ratio was observed to be from 69% to 100%, from 75% to 100%, from 81% to 100%, from 94% to 100%, or 100%. If no cell loss occurred prior to injection into the first sorting stage, recovery ratio in a system having a first sorting stage, a dispersion stage, and a second sorting stage is 99.5% to 100%.

Particle Release

After the particles or cells (e.g., target particles or target cells) are captured, imaged in the filter element, and analyzed, different techniques can be used to release the cells (e.g., for collection and/or further processing, such as imaging on a separate chip, well plate, slide, or vial or sequencing or PCR analysis). To increase the cell release efficiency, multiple fluidic designs and sample treatment options exist.

Efficient release of cells from the filter element is achieved when the cells experience higher fluidic pressure forcing them away from the filter than the fluid pressure causing them to associate with the filter (e.g., causing them to contact the filter). One method of accomplishing this is to reverse the direction of fluid flow across the filter in order to push the cells away from the filter. Fluid flow direction was reversed by increasing fluid pressure downstream of the filter relative to fluid pressure upstream of the filter. Pressure increase downstream of the filter is accomplished by applying pressure to one or more flow path connected to the filtration area downstream of the filter, such as a fluid outlet or an inlet for additional fluid, as shown in FIG. 29A. In some cases, fluid flow direction is reversed by decreasing fluid pressure upstream of the filter relative to fluid pressure downstream of the filter by applying negative pressure (e.g., a vacuum) at a location upstream of the filter. It is contemplated that efficient release of cells from a filter is accomplished when fluid pressure is increased downstream of the filter and fluid pressure is decreased upstream of the filter. Before fluid flow direction is reversed, a structure or device configured to prevent or control backflow of fluid (e.g., a valve, such as shown in FIG. 30A) located upstream of the filter and downstream of an upstream sorting stage is closed so that fluid can't travel back up to the sorting stages, while a valve upstream of the filter is opened to allow the cells to travel through a flow path to a vial for collection.

Increasing pressure differential across one or more specific portions of the filter (e.g., local pressure increase) aids in releasing cells from the filter. Local pressure increase was accomplished by reducing the cross-sectional area of the filter that is permissive of fluid flow by blocking a portion of a filter (e.g., blocking a portion of the filter comprising one or more aperture). Apertures of the filter were blocked by adding polystyrene beads to the filtration area downstream of the filter via a flow path connected to the filtration area.

Initially an aperture of a filter element that does not have a target cell physically associated with the aperture (e.g., a target cell fully or partially blocking the upstream side of the aperture) has a larger cross section permissive of fluid flow than an aperture with an associated cell and will experience higher fluid flow rates than apertures of the filter that have one or more target cell associated with the upstream side of the aperture, as the one or more aperture-associated cells partially or completely block the fluid path of through the aperture. By introducing a material (e.g., a particle, such as a bead) capable of blocking one or more aperture of the filter to the downstream side of the filter during fluid flow reversal, the pressure pushing one or more target cells associated with the upstream side of apertures of the filter away from the filter is increased more specifically and to a greater degree than if the material were not introduced to the downstream side of the filter, improving the chance that the target cell(s) will be released from the filter. While polystyrene beads were used to block apertures of the filter and increase local pressure across the filter, it is contemplated that any means of blocking an aperture of the filter can be used, such as introduction of particles having other shapes downstream of the filter.

FIG. 29B illustrates the introduction of a plurality of beads to the downstream portion of the filter in order to increase local pressure in apertures of a filter for improved release of cells (e.g., target cells) from the upstream side of the filter. After fluid flow through the device is reversed, a solution (e.g., an additional fluid) comprising polystyrene beads is introduced to the filter. Flow through apertures of the filter partially or fully blocked by one or more cells on the upstream side of the filter is initially lower than flow through apertures of the filter not partially or fully blocked by one or more cell on the upstream side of the filter. The polystyrene beads preferentially associate with apertures on the downstream side of the filter that are not associated with a cell or have less cross-section area blocked by a cell on the upstream side of the filter, due to the lower resistance and higher flow rate. Fluid flow and pressure increase in apertures not partially or fully blocked by a bead on the downstream side of the filter (e.g., apertures associated with one or more cells on the upstream side of the filter) during reverse fluid flow, causing pressure against the cells to increase and aiding in the release of cells from the filter.

When reverse fluid flow through the filter is to be minimized (for example, in cases where small cells may travel back through the filter from the downstream side to the upstream side if fluid flow is reversed), fluidic pressure is equalized across the filter by application of positive pressure downstream of the filter, application of negative pressure upstream of the filter, or a combination thereof to release cells from the filter.

After cells are released from the filter of a filtration area, the cells are flushed from the upstream portion of filtration area (e.g., a portion of the filtration area upstream of the filter) into a flow path connecting the filtration area to a collection vial.

Example 5

Multi-Stage Sorting and Dispersion with High Particle Concentration

This example describes a "high concentration" version of a multi-stage sorting apparatus according to an aspect of the present disclosure. Methods and systems comprising a high concentration version of a multi-stage sorting apparatus and its use can be helpful in avoiding cell loss common in the steps of collecting, centrifuging, and/or filtering cells into a fluid volume appropriate for subjection to subsequent preparation steps and assays (e.g., through reduction in fluid volume).

Fluid Collection Volume Reduction

FIG. 30A shows an example of a valve in a flow path of a multi-stage sorting apparatus (e.g., a multi-stage eDAR system) which can be used for any method or in any system wherein a flow path can be closed off, including those involving the concentration of a rare particle in a fluid volume. In high concentration versions of a multi-stage sorting apparatus, a valve is located downstream of a second sorting stage of a multi-stage sorting apparatus. In some cases, the valve is integrated into a microfluidic chip comprising the multi-stage sorting apparatus (e.g., as shown in FIG. 30A), and, in some cases, the valve is external to the microfluidic chip (e.g., as shown in FIG. 30C). The valve is configured to remain closed except when a target cell travels to the valve in a fluid volume from the second sorting stage, which is upstream of the valve. The valve is a solenoid valve and is configured to open briefly and close again quickly to allow the fluid volume containing the target cell through the flow path. The opening of the valve is controlled with a signal from a computer in communication with an upstream detector configured to detect cells (e.g., target cells).

In many cases, the solenoid valve is configured to open and close in 2-3 milliseconds or less. Depending on the pressure and velocity of the fluid containing the target particle when it reaches the valve, the response time of this valve is fast enough to allow just a few nanoliters or less of fluid to pass through the flow path at which the valve is located (e.g., for collection of the target cell). In a case where the flow rate of the fluid in the flow path is 5 µL/min, the valve can open and close quickly enough that 0.17 nL to 0.25 nL passes through the valve for each event that the valve is opened. In a case where the flow rate of the fluid in the flow path is 1000 µL/min, the valve can open and close quickly enough that 34 nL to 50 nL passes through the valve for each event that the valve is opened. As a result, the valve can allow from 0.17 nL to 50 nL to pass through the flow path where the valve is located for each event that the valve is opened to let a target cell pass. A high concentration version of a multi-stage sorting apparatus is able to sort 16 SKBr-3 cells into a final fluid volume of 30 µL from an original volume of 2 mL of blood using a solenoid valve located at a point in a flow path downstream of the second sorting stage. After passing through the flow path where the valve is located, the concentrated volume is collected in a collection vial in fluidic communication with the flow path. For many applications and configurations of the system, fluid volume reduction is performed on a fluid volume as it is received from the second sorting stage.

FIG. 30B shows a schematic of a configuration of a high concentration system useful in concentrating a sorted target cell in a fluid volume as the fluid volume comprising the target cell is received from the second sorting stage. In this example, the flow path configuration shown in FIG. 30B is connected to a multi-stage sorting apparatus downstream of a microfluidic chip. A first flow path leading from the sorting stage branches into a second flow path, which comprises deformable tubing and is connected to a particle collection vial, and a third flow path, which comprises deformable tubing and is connected to a waste vial. A two-way solenoid pinch valve is positioned relative to the second and third flow paths so that the two-way pinch valve closes off (e.g., pinches shut) the second flow path and leaves open the third flow path in its default state but closes off the third flow path and leaves open the second flow path when activated.

A computer in communication with a detector located in the second sorting stage controls the activation of the two-way pinch valve. It is contemplated that the computer can be connected, alternatively or additionally, to a detector in a first sorting stage of the multi-stage sorting apparatus or a detector in a filtration area of the multi-stage sorting apparatus for controlling the two-way pinch valve. When a target particle (i.e., a target cell in this example) is detected by the detector, the computer activates the two-way pinch valve, and the state of the pinch valve switches to allow the fluid to flow through the second flow path to the collection vial and closes off fluid flow through the third flow path.

Collection of target cells can be improved by inclusion of an in-line two-way solenoid valve in the second flow path comprising flexible tubing, which connects the microfluidic chip to a collection vial. In its default state, the in-line two-way valve is configured to pinch off (or close) a portion of the second flow path at a downstream location of the second flow path by compressing the flexible tubing and to allow flow through a portion of the second flow path at an upstream location of the second flow path. When activated, the in-line two-way valve is configured to pinch off (or close) the portion of the second flow path at the upstream location of the second flow path and to allow flow through the portion of the second flow path at the downstream location. When a target cell is detected by a detector in the second sorting stage of the multi-stage sorting apparatus and/or in the microfluidic chip of the multi-stage sorting apparatus and the target cell(s) enters a portion of the second flow path between the upstream and downstream locations of the flow path the in-line two-way solenoid valve is activated to allow a small volume on the order of 1-30 nL that comprises the target cell to pass into the collection vial. The volume of fluid allowed to pass through the in-line two-way valve depends on the distance between the upstream and downstream locations of the second flow path and the diameter of the second flow path.

In another example, a valve is located in the flow path between the second sorting stage and an outlet of the multi-stage sorting apparatus downstream of the microfluidic chip, causing target particles to collect in the flow path between the second sorting stage and the microfluidic chip. After sorting is complete the flow path is interfaced with a collection vial (e.g., by connecting the collection vial to a port of the outlet or by physically moving the outlet to a vial. The valve is then opened and target particles are flushed out of the outlet of the flow path.

A known number of SKBr-3 cells were added to 2, 4 or 8 mL of blood and processed and separated as described herein using a two-stage sorting apparatus. The cells collected in the collection vial were counted and the number was compared to the number of cells added for each experiment. Cell recovery efficiency ranged from 50% to 100% with a median of 77% using this configuration for concentration of particles in a fluid volume. The final fluid volumes in which cells were collected following fluid volume reduction were between 20 uL to 150 uL.

Greater control of the particle movement and of the volume collected from the multi-stage sorting apparatus in these examples is accomplished by triggering valve activation (e.g., switching the valve state and which flow path is closed and which is open) independently from a detector of the multi-stage sorting apparatus. Independent activation of the two-way pinch valve (or any other valve in the multi-stage sorting apparatus) can be controlled in various ways, including using a signal from a timer, a pressure sensor, or a user-input device.

FIG. 30C shows a configuration of a system wherein a valve useful for concentrating and/or collecting a sorted target cell or a plurality of sorted target cells is external to the microfluidic chip comprising the multi-stage sorting apparatus. A solenoid valve can be used for this purpose. The external valve for concentrating one or more target cells is in fluidic communication with the flow path and is configured to open briefly and close again quickly to allow the fluid volume containing the target cell through the flow path. The opening of the external valve is controlled with a signal from a computer in communication with an upstream detector configured to detect cells (e.g., target cells). The external valve is configured to open briefly (e.g., 1, 2, 3, 4, 5, 6, 7, 8, 9, 10, 11, 12, 13, 14, 15, 16, 17, 18, 19, 20 milliseconds, less than 2 milliseconds, from 2 milliseconds to 20 milliseconds, or from 20 milliseconds to 50 milliseconds) as each cell is detected in the second sorting stage. When the valve is open for a time from 2 milliseconds to 20 milliseconds, 1 to 30 nanoliters (nL) of fluid passes through the valve, moving the cell(s) in the fluid down the fluid path.

As shown in FIG. 30C, the valve (e.g., the external collection valve) is connected to an outlet of the microfluidic sorting chip with tubing. After cells have been sorted in the second sorting stage, the sorted cells are present in the fluid volume between the second sorting stage and the valve (e.g., the cells are in the flow path of the chip and/or tubing (e.g., collection tubing) between second sorting stage and the valve). The tubing is disconnected from the valve and placed in fluid communication with a collection vial (e.g., manually or via mechanical displacement controlled by a computer). The cells present in the fluid volume between the second sorting stage and the valve are flushed out of the flow path and/or tubing and into the collection vial by applying fluid pressure upstream of one or both of the sorting stages.

Fluid Collection Volume Reduction with Additional Fluid Paths

Passive methods and devices for reducing the volume of fluid in which target particles are collected are used in certain embodiments of the methods and apparatuses described herein. As shown in FIG. 31, the concentration of target cells (e.g., target particles) in a fluid volume is increased after the fluid volume comprising the target cell(s) passes out of the second sorting stage of a multi-stage sorting apparatus by configuring the geometry of the flow path to which the fluid volume passes after leaving the second sorting stage to promote cross-flow filtration (i.e., tangential filtration). In this example, a portion of the flow path comprises a filter separating the fluid volume containing the target cell(s) from a filtrate region 3130 in fluid communication with a fluid outlet (e.g., a primary fluid outlet). In such cases, the flow path can be separated from the plurality of regions and fluid outlets by a filter 3110 having slits (or pores, steps, gaps, and/or apertures) 3120 with at least one dimension sized to prevent a target cell from crossing the filter while allowing fluid(s) and/or cells having a smaller dimension or greater degree of deformability to pass through the slits (or pores, steps, gaps, and/or apertures) 3120 of the filter.

As shown in FIG. 31, a filtrate region 3130 may have a larger volume than the volume of the flow path comprising the filter. As the fluid volume enters the portion of the flow path having these features, a portion of the fluid volume passes through the filter into the filtrate region 3130. The target cell(s) are prevented from passing through the slits of the filter (e.g., because the slits of the filter have one or more dimension sized to prevent cells from passing through any of the slits of the filter) and remain on the opposite side of the filter as filtrate region 3130 as they pass through the portion of the flow path comprising the filter. As shown in FIG. 31, the flow path can be in fluid communication with more than one filtrate region 3130, each of which can be in fluid communication with one or more fluid outlet.

While the volumetric differential between the portion of the flow path in which the target cell(s) are located and filtrate region 3130 is sufficient to cause a portion of the fluid volume to spread across the filter to the larger volume of the filtrate region 3130, additional passive means of concentrating the cell(s) in the fluid volume are useful in the practice of methods and apparatuses described herein.

For example, in one example the flow path is not straight and comprises a filter disposed on an outside wall of the flow path at the portion of the flow path that is not straight. As the fluid volume comprising the target cell(s) travels toward the portion of the flow path that is not straight, the momentum of the fluid volume exerts a force against the filter, and a portion of the fluid volume passes through the apertures of the filter to a portion of the flow path located on the opposite side of the filter as the cell(s) (e.g., a filtrate region). The apertures of the filter are sized to disallow cells from passing through the filter, and the cell(s) of the fluid volume are blocked from passing through the filter. In this example, the fluid volume is reduced by allowing the inertia of the fluid volume to cause a portion of the fluid volume to pass through the filter while not allowing the cells to do the same.

It is contemplated that cells contacting the filter as a result of passing through a section of the flow path with this structure and geometry applies forces to the cells which may impact cellular phenotype or viability. This is most often true if the portion of the flow path that is not straight comprises an angle or bend in the flow path of 90 degrees or greater from its original direction. When the effect on cell phenotype or viability as a result of lateral displacement or inertial forces is a particular concern, the angle or bend in the flow path is made to comprise an angle or bend of less than 90 degrees from its original direction. In any event, the angle of a bend in a flow path for fluid volume reduction after sorting is based on considerations of the velocity of the fluid volume (and cell(s) contained in the fluid volume) as well as the size, deformability, and morphology of the cell(s).

The filter used in these examples of passive fluid volume reduction comprises apertures of similar shape and size; however, it is also contemplated that a continuous filter comprising apertures of various shapes or sizes or a plurality of filters comprising apertures of different shapes or sizes are useful in separating cells of different sizes or identities. In one example, the apertures of a filter in a portion of a flow path comprising a spiral-shaped bend are smaller in cross-sectional area at an upstream portion of the filter than the apertures of the filter at a downstream portion of the filter. When a fluid volume comprising a heterogeneous mixture of cells is passed through the flow path, smaller cells will pass through the upstream portion of the filter while larger cells will pass through the downstream of the filter, leaving only the largest cells, which are not able to pass through any of the apertures of the filter on the original side of the filter. In this case, the flow path is connected to a plurality of outlet channels at different points along the length of the flow path so that cells of different sizes that have passed through the filter at different points along the length of the flow path can be collected separately by different channels of the plurality of outlet channels.

What is claimed is:

1. A method for collecting a particle in a fluid sample, the method comprising:
   detecting a first presence of the particle in a first aliquot of the sample, wherein the aliquot comprises a plurality of particles including the particle, and wherein particles of the plurality of particles occupy a three-dimensional space and are distributed within the three-dimensional space;
   upon detecting the presence of the particle in the first aliquot, directing the flow of the first aliquot to a first volume to form a first isolated sample;
   dispersing the first isolated sample, wherein dispersing the first isolated sample is imparted by parabolic flow of the first collected sample through a flow path or by herringbone mixing of the first collected sample in a herringbone mixer, to form a dispersed sample including the particle downstream of the flow path or the herringbone mixer, and wherein dispersing the first isolated sample results in an overall lengthening of the first isolated sample containing the particle; and
   subjecting the dispersed sample to a separation procedure.

2. The method of claim 1, wherein the separation procedure is an active separation procedure or a passive separation procedure.

3. The method of claim 1, wherein detecting the first presence of the particle comprises:
   interrogating the particle in the first aliquot with a source of a first electromagnetic radiation; and
   detecting a first interaction of the first electromagnetic radiation with the particle in the first aliquot.

4. The method of claim 1, wherein detecting the first presence of the particle in the first aliquot is performed during continuous flow of the fluid sample.

5. The method of claim 1, wherein the particle is a rare particle.

6. The method of claim 5, wherein the rare particle is a cell.

7. The method of claim 1, wherein the dispersing the first isolated sample comprises weir mixing of the first isolated sample.

8. The method of claim 1, wherein dispersing the first isolated sample is imparted by flow of the first isolated sample through a plurality of flow paths including the flow path.

9. The method of claim 1, wherein the plurality of particles includes a cell, wherein dispersing the first isolated sample comprises altering a velocity of the cell.

10. The method of claim 9, wherein dispersing the first isolated sample is imparted by flowing the first isolated sample through a barrier comprising a filter structure or a constriction of the channel.

11. The method of claim 10, wherein the barrier alters the velocity of a cell based on a physical attribute of the cell selected from the group consisting of: cell volume, cell shape, and cell deformability.

12. The method of claim 1, wherein the separation procedure comprises:
   interrogating the particle with a source of second electromagnetic radiation; and
   detecting a second interaction of the second electromagnetic radiation with the particle.

13. The method of claim 1, wherein the separation procedure comprises a procedure selected from the group consisting of fluorescence activated aliquot sorting, ensemble decision aliquot ranking (eDAR), flow cytometry, fluorescence activated cell sorting (FACS), magnetic-activated cell sorting (MACS).

14. The method of claim 1, wherein detecting the second presence of the particle is performed during continuous flow of the fluid sample.

15. The method of claim 1, further comprising collecting the particle in a structure selected from the group consisting of: a vial, a well plate and a filtration volume.

16. The method of claim 1, wherein dispersing the first isolated sample comprises passing the first isolated sample through one or more barrier, one or more weir stretcher, one or more microslit, or one or more microfilter.

17. The method of claim 1, further comprising passing the dispersed sample through a passive fluidic structure to purify the particle.

\* \* \* \* \*